(12) United States Patent
Kurian et al.

(10) Patent No.: US 12,209,283 B2
(45) Date of Patent: Jan. 28, 2025

(54) GENOME-WIDE CLASSIFIERS FOR DETECTION OF SUBACUTE TRANSPLANT REJECTION AND OTHER TRANSPLANT CONDITIONS

(71) Applicants: THE SCRIPPS RESEARCH INSTITUTE, La Jolla, CA (US); NORTHWESTERN UNIVERSITY, Evanston, IL (US)

(72) Inventors: Sunil M. Kurian, San Diego, CA (US); Michael M. Abecassis, Chicago, IL (US); John J. Friedewald, Chicago, IL (US)

(73) Assignees: THE SCRIPPS RESEARCH INSTITUTE, La Jolla, CA (US); NORTHWESTERN UNIVERSITY, Evanston, IL (US)

( * ) Notice: Subject to any disclaimer, the term of this patent is extended or adjusted under 35 U.S.C. 154(b) by 285 days.

(21) Appl. No.: 17/053,834

(22) PCT Filed: May 10, 2019

(86) PCT No.: PCT/US2019/031850
§ 371 (c)(1),
(2) Date: Nov. 9, 2020

(87) PCT Pub. No.: WO2019/217910
PCT Pub. Date: Nov. 14, 2019

(65) Prior Publication Data
US 2021/0230697 A1 Jul. 29, 2021

Related U.S. Application Data

(60) Provisional application No. 62/669,518, filed on May 10, 2018.

(51) Int. Cl.
| | | |
|---|---|---|
| *C12Q 1/6883* | (2018.01) | |
| *C12Q 1/6881* | (2018.01) | |
| *G16B 25/10* | (2019.01) | |
| *G16B 50/20* | (2019.01) | |

(52) U.S. Cl.
CPC ......... *C12Q 1/6883* (2013.01); *C12Q 1/6881* (2013.01); *G16B 25/10* (2019.02); *G16B 50/20* (2019.02); *C12Q 2600/112* (2013.01); *C12Q 2600/118* (2013.01); *C12Q 2600/142* (2013.01); *C12Q 2600/158* (2013.01)

(58) Field of Classification Search
None
See application file for complete search history.

(56) References Cited

U.S. PATENT DOCUMENTS

2016/0348174 A1* 12/2016 Sarwal .................... A61P 13/12
2017/0137885 A1* 5/2017 Salomon ................ G16H 50/20

FOREIGN PATENT DOCUMENTS

WO 2015/035367 A1 3/2015
WO 2015/179777 A2 11/2015

OTHER PUBLICATIONS

Li (American Journal of Transplantation 2012 12:2710-2718).*
Flechner (American Journal of Transplantation 2004 4:1475-1489).*
Kurian (American Journal of Transplantation 2014 14:1164-1172).*
First (Journal of Transplantation Technologies & Research 2017 7:3 Pub Nov. 10, 2017).*
Elena Crespo, et al., Molecular and Functional Noninvasive Immune Monitoring in the ESCAPE Study for Prediction of Subclinical Renal Allograft Rejection, Tranlantation (Jun. 2017) vol. 101, No. 6, p. 1400-1409.
M.R. First, et al., Clinical utility of peripheral blood gene expression profiling of kidney transplant recipients to assess the need for surveillance biopsies in subjects with stable renal function, Journal of Transplantation Technologies & Research (2017) vol. 7, Issue 3, 177.
John J. Friedewald, et al., Development and clinical validity of a novel blood-based molecular biomarker for subclinical acute rejection following kidney transplant, American Journal ofTransplant. (2019) 19:98-109.
Extended European Search Report issued May 9, 2023, in corresponding European Application No. EP 23154191.3.

* cited by examiner

*Primary Examiner* — Amanda Haney
(74) *Attorney, Agent, or Firm* — Duane Morris LLP; Thomas J. Kowalski

(57) ABSTRACT

This disclosure provides methods of detecting sub-acute rejection and other categories of rejection in kidney transplant recipients using unique sets of gene expression markers.

20 Claims, 13 Drawing Sheets

Figure 7

| Thresh | Overall | Sens. (subAR Acc.) | Spec. (TX Acc.) | PPV | NPV |
|---|---|---|---|---|---|
| 0.575 | 0.70 | 0.02 | 1.00 | 1.00 | 0.70 |
| 0.55 | 0.70 | 0.02 | 1.00 | 1.00 | 0.70 |
| 0.525 | 0.71 | 0.07 | 0.99 | 0.75 | 0.71 |
| 0.5 | 0.71 | 0.14 | 0.96 | 0.60 | 0.72 |
| 0.475 | 0.72 | 0.19 | 0.95 | 0.62 | 0.73 |
| 0.45 | 0.70 | 0.29 | 0.89 | 0.52 | 0.74 |
| 0.425 | 0.72 | 0.40 | 0.86 | 0.57 | 0.77 |
| 0.4 | 0.70 | 0.43 | 0.82 | 0.51 | 0.77 |
| 0.375 | 0.70 | 0.48 | 0.80 | 0.51 | 0.78 |
| 0.35 | 0.70 | 0.55 | 0.77 | 0.51 | 0.80 |
| 0.325 | 0.69 | 0.55 | 0.75 | 0.49 | 0.79 |
| 0.3 | 0.68 | 0.60 | 0.72 | 0.48 | 0.80 |
| 0.275 | 0.67 | 0.60 | 0.71 | 0.47 | 0.80 |
| 0.25 | 0.64 | 0.60 | 0.66 | 0.43 | 0.79 |
| 0.225 | 0.59 | 0.64 | 0.57 | 0.40 | 0.79 |
| 0.2 | 0.57 | 0.71 | 0.50 | 0.38 | 0.80 |
| 0.175 | 0.53 | 0.76 | 0.43 | 0.37 | 0.80 |

| N=138 | subAR = Positive | TX = positive | | Model | 5 |
|---|---|---|---|---|---|
| AUC | 0.66 | 0.66 | | Exp Thresh | 0.01 |
| Sens. @ Thresh | 0.48 | 0.80 | | FDR | |
| Spec. @ Thresh | 0.80 | 0.48 | | # of Probes | 61 |
| PPV @ Thresh | 0.51 | 0.78 | | Bootstrap AUC | 0.84 |
| NPV @ Thresh | 0.78 | 0.51 | | Thresh | 0.375 |

| Thresh | Overall | Sens. (subAR Acc.) | Spec. (TX Acc.) | PPV | NPV |
|---|---|---|---|---|---|
| 0.575 | 0.73 | 0.03 | 1.00 | 1.00 | 0.73 |
| 0.55 | 0.73 | 0.03 | 1.00 | 1.00 | 0.73 |
| 0.525 | 0.74 | 0.08 | 0.99 | 0.75 | 0.74 |
| 0.5 | 0.73 | 0.14 | 0.96 | 0.56 | 0.74 |
| 0.475 | 0.74 | 0.19 | 0.95 | 0.58 | 0.75 |
| 0.45 | 0.71 | 0.28 | 0.88 | 0.48 | 0.76 |
| 0.425 | 0.73 | 0.39 | 0.86 | 0.52 | 0.78 |
| 0.4 | 0.71 | 0.42 | 0.82 | 0.47 | 0.78 |
| 0.375 | 0.71 | 0.47 | 0.80 | 0.47 | 0.80 |
| 0.35 | 0.70 | 0.53 | 0.76 | 0.46 | 0.81 |
| 0.325 | 0.68 | 0.53 | 0.74 | 0.44 | 0.80 |
| 0.3 | 0.67 | 0.56 | 0.71 | 0.43 | 0.80 |
| 0.275 | 0.66 | 0.56 | 0.70 | 0.42 | 0.80 |
| 0.25 | 0.62 | 0.56 | 0.65 | 0.38 | 0.79 |
| 0.225 | 0.57 | 0.61 | 0.56 | 0.35 | 0.79 |
| 0.2 | 0.54 | 0.69 | 0.48 | 0.34 | 0.80 |
| 0.175 | 0.50 | 0.72 | 0.42 | 0.33 | 0.80 |

| N=129 | subAR = Positive | TX = positive | | Model | 5 |
|---|---|---|---|---|---|
| AUC | 0.63 | 0.63 | | Exp Thresh | 0.01 |
| Sens. @ Thresh | 0.47 | 0.80 | | FDR | |
| Spec. @ Thresh | 0.80 | 0.47 | | # of Probes | 61 |
| PPV @ Thresh | 0.47 | 0.80 | | Bootstrap AUC | 0.84 |
| NPV @ Thresh | 0.80 | 0.47 | | Thresh | 0.375 |

| Threshold = 0.375 | Resolved (N=11) | Unresolved (N=12) | p-value* | Adjusted p-value** |
|---|---|---|---|---|
| Probability scores | | | | |
| Baseline (biopsy) | 0.355±0.190 | 0.486±0.129 | 0.073 | N/A |
| IM2 (4 weeks) | 0.160±0.168 | 0.386±0.200 | 0.014 | 0.045 |
| IM 4 (8 weeks) | 0.269±0.186 | 0.450±0.127 | 0.015 | 0.023 |
| Change in probability scores (slope) | | | | |
| Baseline to IM2 | -0.209±0.229 | -0.108±0.202 | 0.31 | 0.045 |
| Baseline to IM4 | -0.087±0.248 | -0.035±0.202 | 0.59 | 0.023 |

\* Based on the two-sample t-test
\*\* Adjusted for GEP predicted probability scores at baseline using analysis of covariance

GENOME-WIDE CLASSIFIERS FOR DETECTION OF SUBACUTE TRANSPLANT REJECTION AND OTHER TRANSPLANT CONDITIONS

CROSS-REFERENCE STATEMENT

This application claims the benefit of U.S. Provisional Patent Application No. 62/669,518, filed on May 10, 2018, which is incorporated by reference herein in its entirety.

STATEMENT OF GOVERNMENT LICENSE RIGHTS

This invention was made with government support under grant numbers AI063603, AI18493 and AI084146 awarded by the National Institutes of Health. The government has certain rights in the invention.

BACKGROUND

Kidney transplantation offers a significant improvement in life expectancy and quality of life for patients with end-stage renal disease. Despite improvements in tissue-typing/matching technology, graft losses due to allograft dysfunction or other uncertain etiologies have greatly hampered the therapeutic potential of kidney transplantation. Furthermore, repeated transplant monitoring (often involving painful biopsies) remains a common approach for managing/predicting changes in graft function over time.

SUMMARY

Following kidney transplantation, clinically undetected (and therefore untreated) sub-clinical acute rejection (subAR) occurs in 20-25% of patients in the first 12 months, is associated with de novo donor-specific antibody (dnDSA) formation, worse 24-month transplant outcomes, interstitial fibrosis and tubular atrophy (IFTA), chronic rejection, and graft loss. Serum creatinine and immunosuppression levels, used almost exclusively to monitor kidney transplant recipients, are both insensitive and non-specific. Surveillance biopsies can be used to monitor patients with stable renal function, but they are invasive, are associated with sampling error and there is a lack of consensus around both histologic interpretation (especially for 'borderline changes') and the effectiveness of treatment. Moreover, the vast majority (75-80%) of surveillance biopsies show normal histology (i.e. the absence of subAR) and therefore expose patients to unnecessary biopsy risks. Accordingly there is need for minimally-invasive methods for monitoring kidney transplant function and immunological status.

In some aspects, the present disclosure provides for A method of distinguishing a non-transplant excellent kidney from a transplant excellent kidney in a kidney transplant recipient on an immunosuppressant treatment regimen, the method comprising: (a) providing mRNA derived from a blood sample from the kidney transplant recipient on the immunosuppressant treatment regimen or cDNA complements of mRNA derived from a blood sample from the kidney transplant recipient on the immunosuppressant treatment regimen, wherein the kidney transplant recipient has a stable creatinine level; (b) performing a microarray assay or sequencing assay on the mRNA derived from the blood sample from the kidney transplant recipient on the immunosuppressant treatment regimen or the cDNA complements of mRNA derived from the blood sample from the kidney transplant recipient on the immunosuppressant treatment regimen in order to determine gene expression levels in the blood sample; and (c) detecting a non-transplant excellent kidney or a transplant excellent kidney by applying a trained algorithm to at least a subset of the gene expression levels determined in (b), wherein the trained algorithm distinguishes a transplant excellent kidney from a non-transplant excellent kidney, wherein a non-transplant excellent kidney includes a kidney with acute rejection, sub-acute Rejection (subAR), acute dysfunction with no rejection, and kidney injury. In some embodiments, the trained algorithm performs a binary classification between a transplant excellent kidney and a non-transplant excellent kidney. In some embodiments, the trained algorithm performs a binary classification between a transplant excellent kidney and a non-transplant excellent kidney. In some embodiments, the gene expression levels comprise levels of at least 5 genes selected from Table 3 or 4. In some embodiments, the gene expression levels comprise levels of at least 10 genes, at least 20 genes, at least 40 genes, at least 50 genes, at least 60 genes, at least 70 genes, at least 80 genes, at least 90 genes or all of the genes in Table 3 or 4. In some embodiments, the method has a positive predictive value (PPV) of greater than 40%, 65%, greater than 70%, greater than 75%, greater than 80%, greater than 85%, greater than 90%, or greater than 95%. In some embodiments, the method has a negative predictive value (NPV) of greater than 65%, greater than 70%, greater than 75%, greater than 80%, greater than 85%, greater than 90%, or greater than 95%. In some embodiments, the method comprises detecting a transplant excellent condition in the kidney transplant recipient and the method further comprises administering a treatment to kidney transplant recipient based on the detected transplant excellent condition. In some embodiments, the treatment comprises administering a new immunosuppressant to the kidney transplant recipient, continuing the immunosuppressant treatment regimen of the kidney transplant recipient, or adjusting the immunosuppressant treatment regimen of the kidney transplant recipient, either by increasing the immunosuppressant dosage or decreasing the immunosuppressant dosage. In some embodiments, the treatment further comprises periodically obtaining blood samples from the kidney transplant recipient and monitoring the blood samples for markers of a non-transplant excellent condition. In some embodiments, the monitoring the blood samples comprises detecting expression levels of at least five genes from the genes listed in Table 3 or Table 4. In some embodiments, the treatment comprises abstaining from performing a protocol biopsy of the kidney transplant of the kidney transplant recipient after the transplant excellent condition is detected in a blood sample from the kidney transplant recipient at least one time, at least two consecutive times, or at least three consecutive times. In some embodiments, the method comprises monitoring gene expression products in a blood sample obtained from a kidney transplant recipient on different days, wherein the markers are mRNA expression products of at least 5 genes, at least 10 genes, at least 20 genes, at least 30 genes, at least 50 genes, at least 100 genes or all of the genes from Tables 3 or 4. In some embodiments, the treatment further comprises periodically obtaining blood samples from the kidney transplant recipient and monitoring the blood samples in order to detect subAR in the kidney transplant recipient. In some embodiments, the monitoring the blood samples in order to detect subAR in the kidney transplant recipient comprises detecting mRNA expression products of at least 5 genes, at least 10 genes, at least 20 genes, at least 30 genes, at least 50 genes, or all of the genes in Tables 5, 6, or 8. In some embodiments, the method detects a non-transplant excellent condition in the kidney transplant recipient and the method further comprises administering a treatment to the kidney transplant recipient based on the detected non-transplant excellent condition. In some embodiments, the treatment comprises performing a biopsy on the kidney transplant recipient in order to further identify the detected non-transplant excellent condition. In some embodiments, the method further comprises monitoring blood samples from the kidney transplant recipient in order to detect a non-transplant excellent condition. In some embodiments, the non-transplant condition is monitored by detecting mRNA expression levels of at least 5 genes, at least 10 genes from Tables 3 or 4 in blood samples obtained from the kidney transplant recipient on at least two or at least three different days and further comprising applying a trained algorithm to the detected expression levels in order to distinguish a transplant excellent condition from a non-transplant excellent condition. In some embodiments, the treatment further comprises monitoring the blood samples in order to detect subAR in the kidney transplant recipient. In some embodiments, the monitoring the blood samples in order to detect subAR in the kidney transplant recipient comprises detecting mRNA expression products of at least 5 genes, at least 10 genes, at least 20 genes, at least 30 genes, at least 50 genes, or all of the genes in Table 5, 6, or 8 and applying a trained algorithm to the detected mRNA expression products. In some embodiments, the method further comprises administering an immunosuppressant drug to the kidney transplant recipient to treat the detected subAR or the detected non-transplant excellent condition. In some embodiments, the method further comprises administering an increased or decreased dose of the immunosuppressant drug to the kidney transplant recipient in order to treat or prevent the detected non-transplant excellent condition or detected subAR or administering a new immunosuppressant drug to the kidney transplant recipient in order to treat or prevent the detected non-transplant excellent condition or the detected subAR. In some embodiments, the immunosuppressant drug or the new immunosuppressant drug is a calcineurin inhibitor. In some embodiments, the immunosuppressant drug or the new immunosuppressant drug is an mTOR inhibitor. In some embodiments, the immunosuppressant drug or new immunosuppressant drug is selected from the group consisting of: azathioprine, leflunomide, mycophenolic acid, mycophenolate mofetil, prednisolone, hydrocortisone, basiliximab, alemtuzumab, daclizumab, belatacept, orthoclone, anti-thymocyte globulin, anti-lymphocyte globulin, an anti-proliferative drug, and an anti-T cell antibody. In some embodiments, the method further comprises detecting a serum creatinine level or an eGFR in a blood sample from the kidney transplant recipient. In some embodiments, the method further comprises using a serum creatinine level or an eGFR to further confirm the detected subAR, the detected non-transplant excellent condition, or the detected transplant excellent condition.

In some aspects, the present disclosure provides for a method of detecting sub-acute rejection (subAR) in a kidney transplant recipient with a stable creatinine level that is on an immunosuppressant drug regimen, the method comprising: (a) providing mRNA derived from a blood sample from the kidney transplant recipient with the stable creatinine level or cDNA complements of mRNA derived from a blood sample from the kidney transplant recipient with the stable creatinine level; (b) performing a microarray assay or sequencing assay on the mRNA derived from the blood sample from the kidney transplant recipient with the stable creatinine level or the cDNA complements of mRNA derived from the blood sample from the kidney transplant recipient with the stable creatinine level in order to determine gene expression levels, wherein the gene expression levels comprise levels of (i) at least 5 genes from Table 5, 6, or 8; or (ii) at least 10 genes, at least 20 genes, at least 30 genes, at least 40 genes, at least 50 genes, or all of the genes in Table 5, 6, or 8; and (c) detecting subAR or detecting an absence of subAR by applying a trained algorithm to the gene expression levels determined in (b), wherein the trained algorithm distinguishes at least a transplant excellent kidney from a subAR kidney, with a negative predictive value (NPV) of at least 60% or a positive predictive value (PPV) of at least 30%, or both. In some embodiments, the gene expression levels comprise the levels of at least five of the genes in Tables 5, 6, or 8. In some embodiments, the trained algorithm distinguishes a subAR kidney from a transplant excellent kidney with an NPV of greater than 78%. In some embodiments, the trained algorithm distinguishes a subAR kidney from a transplant excellent kidney with a PPV of greater than 47%. In some embodiments, the kidney transplant recipient has a serum creatinine level of less than 2.3 mg/dL. In some embodiments, the method further comprises administering an adjusted dose, an increased dose or a decreased dose of the immunosuppressant drug to the kidney transplant recipient in order to treat or prevent the detected subAR or administering a new immunosuppressant drug to the kidney transplant recipient in order to treat or prevent the detected subAR. In some embodiments, the immunosuppressant drug or the new immunosuppressant drug is a calcineurin inhibitor. In some embodiments, the immunosuppressant drug or the new immunosuppressant drug is an mTOR inhibitor. In some embodiments, the immunosuppressant drug or new immunosuppressant drug is selected from the group consisting of: azathioprine, leflunomide, mycophenolic acid, mycophenolate mofetil, prednisolone, hydrocortisone, basiliximab, alemtuzumab, daclizumab, belatacept, orthoclone, anti-thymocyte globulin, anti-lymphocyte globulin, an anti-proliferative drug, and an anti-T cell antibody. In some embodiments, the treatment further comprises monitoring the blood samples in order to detect subAR or a transplant excellent condition in the kidney transplant recipient at two or more time points. In some embodiments, the monitoring the blood samples in order to detect subAR or a transplant excellent condition in the kidney transplant recipient comprises detecting mRNA expression products of at least 5 genes, at least 10 genes, at least 20 genes, at least 30 genes, at least 50 genes, or all of the genes in Table 5, 6, or 8. In some embodiments, the treatment comprises abstaining from performing a protocol biopsy of the kidney transplant of the kidney transplant recipient after the transplant excellent condition is detected in a blood sample from the kidney transplant recipient at least one time, at least two consecutive times, or at least three consecutive times. In some embodiments, the method comprises monitoring gene expression products in a blood sample obtained from a kidney transplant recipient on different days, wherein the markers are mRNA expression products of at least 5 genes, at least 10 genes, at least 20 genes, at least 30 genes, at least 50 genes, at least 100 genes or all of the genes from Tables 5, 6, or 8. In some embodiments, the treatment further comprises periodically obtaining blood samples from the kidney transplant recipient and monitoring the blood samples in order to detect subAR or a transplant excellent condition in the kidney transplant recipient. In some embodiments, the method further comprises repeating the method at least one time, at least two times, at least three times, or at least four times in order to monitor a detected transplant excellent condition, a detected non-transplant excellent condition, or a detected sub-acute rejection, or any combination thereof in the kidney transplant recipient.

In some aspects, the present disclosure provides for a method of treating a kidney transplant recipient, comprising: (a) administering an initial immunosuppressant drug regimen to the kidney transplant recipient; (b) providing mRNA derived from a blood sample from the kidney transplant recipient or cDNA complements of mRNA derived from a blood sample from the kidney transplant recipient, wherein the blood sample was obtained while the kidney transplant recipient was following the initial immunosuppressant drug regimen; (c) performing a microarray assay or sequencing assay on at least a subset of the mRNA from the kidney transplant recipient or the DNA complements of the mRNA from the kidney transplant recipient with a stable creatinine level in order to determine gene expression levels, wherein the gene expression levels comprise levels of (i) at least 5 genes from Tables 5, 6, or 8; or (ii) at least 10 genes, at least 20 genes, at least 30 genes, at least 40 genes, at least 50 genes, or all of the genes in Table 5, 6, or 8; (d) identifying a transplant excellent kidney in the kidney transplant recipient by applying a trained algorithm to the gene expression levels (i) or (ii) determined in (c), wherein the trained algorithm distinguishes a transplant excellent kidney from a subAR kidney, with a negative predictive value (NPV) of at least 60% or a positive predictive value (PPV) of at least 30%, or both; and (e) maintaining the administration of the initial immunosuppressant drug regimen to the kidney recipient identified with a transplant excellent kidney for at least one month or adjusting the initial immunosuppressant drug regimen administered to the kidney transplant recipient identified with a transplant excellent kidney. In some embodiments, the administration of the initial immunosuppressant drug regimen is maintained for at least 3 months, at least 5 months, at least 6 months, at least 8 months or at least 1 year following identification of the transplant excellent kidney in (d). In some embodiments, the initial immunosuppressant drug regimen is administered after acute rejection or subAR is detected or suspected in the kidney transplant recipient. In some embodiments, the adjusting of the initial immunosuppressant drug regiment comprises decreasing a dosage of the initial immunosuppressant drug regimen after a transplant excellent condition is identified in (d). In some embodiments, the initial immunosuppressant drug regiment comprises treating the kidney transplant recipient with a new immunosuppressant drug after the transplant excellent condition is identified in (d). In some embodiments, the initial immunosuppressant drug or the new immunosuppressant drug is selected from the group consisting of: a calcineurin inhibitor, an mTOR inhibitor, azathioprine, leflunomide, mycophenolic acid, mycophenolate mofetil, prednisolone, hydrocortisone, basiliximab, alemtuzumab, daclizumab, belatacept, orthoclone, anti-thymocyte globulin, anti-lymphocyte globulin, an anti-proliferative drug, and an anti-T cell antibody, or a combination thereof. In some embodiments, the method further comprises abstaining from performing a biopsy on the kidney transplant recipient after the transplant excellent condition is identified in (d). In some embodiments, the method further comprises abstaining from performing a biopsy on the kidney transplant recipient after the transplant excellent condition is identified in (d) after the method is performed at least two consecutive times, at least three consecutive times, at least four consecutive times, or at least five consecutive times. In some embodiments, the method further comprises repeating (a), (b) and (c) at least one time, at least two times, at least three times, or at least four times over a period of days, weeks, or months. In some embodiments, a subAR condition is detected using the trained algorithm in (d) after the method is performed at least two consecutive times, at least three consecutive times, at least four consecutive times, or at least five consecutive times. In some embodiments, the method further comprises performing a biopsy on the kidney transplant recipient after a subAR condition is detected at least two consecutive times, at least three consecutive times, at least four consecutive times, or at least five consecutive times. In some embodiments, the method further comprises increasing or changing the immunosuppressant drug regimen after a subAR condition is detected at least two consecutive times, at least three consecutive times, at least four consecutive times, or at least five consecutive times after the first transplant excellent condition is detected.

In some aspects, the present disclosure provides for a method of performing a kidney biopsy on a kidney transplant recipient with a stable creatinine level, the method comprising: (a) providing mRNA derived from a blood sample from the kidney transplant recipient or cDNA complements of mRNA derived from a blood sample from the kidney transplant recipient, wherein the blood sample was obtained while the kidney transplant recipient was on an immunosuppressant drug regimen; (b) performing a microarray assay or sequencing assay on at least a subset of the mRNA from the kidney transplant recipient with a stable creatinine level or the DNA complements of the mRNA from the kidney transplant recipient with a stable creatinine level in order to determine gene expression levels, wherein the gene expression levels comprise levels of (i) at least 5 genes from Table 5, 6, or 8; or (ii) at least 10 genes, at least 20 genes, at least 30 genes, at least 40 genes, at least 50 genes, or all of the genes in Tables 5, 6, or 8; (c) detecting sub-acute rejection (subAR) by applying a trained algorithm to the gene expression levels determined in (b), wherein the trained algorithm distinguishes a transplant excellent kidney from a subAR kidney, with a negative predictive value (NPV) of at least 60% or a positive predictive value (PPV) of at least 30%, or both; and (d) performing a kidney biopsy on the kidney transplant recipient with the detected subAR in order to confirm that the kidney transplant recipient has subAR. In some embodiments, the method further comprises treating the subAR detected by the kidney biopsy. In some embodiments, the treating the detected subAR comprises administering an increased or decreased dose of the immunosuppressant drug to the kidney transplant recipient in order to treat the detected subAR or administering a new immunosuppressant drug to the kidney transplant recipient in order to treat the detected subAR. In some embodiments, the immunosuppressant drug or the new immunosuppressant drug is a calcineurin inhibitor. In some embodiments, the immunosuppressant drug or the new immunosuppressant drug is an mTOR inhibitor. In some embodiments, the immunosuppressant drug or new immunosuppressant drug is selected from the group consisting of: azathioprine, leflunomide, mycophenolic acid, mycophenolate mofetil, prednisolone, hydrocortisone, basiliximab, alemtuzumab, daclizumab, belatacept, orthoclone, anti-thymocyte globulin, anti-lymphocyte globulin, an anti-proliferative drug, and an anti-T cell antibody. In some embodiments, the method further comprises contacting the gene expression products with probes, wherein the probes are specific for the at least five genes from Tables 5, 6, or 8.

In some aspects, the present disclosure provides for a method of performing a kidney biopsy on a kidney transplant recipient with a stable creatinine level, the method comprising: (a) providing mRNA derived from a blood sample from the kidney transplant recipient or cDNA complements of mRNA derived from a blood sample from the kidney transplant recipient, wherein the blood sample was obtained while the kidney transplant recipient was on an immunosuppressant drug regimen; (b) performing a microarray assay or sequencing assay on at least a subset of the mRNA from the kidney transplant recipient with a stable creatinine level or the DNA complements of the mRNA from the kidney transplant recipient with a stable creatinine level in order to determine gene expression levels, wherein the gene expression levels comprise levels of (i) at least 5 genes from Table 3 or 4; or (ii) at least 10 genes, at least 20 genes, at least 30 genes, at least 40 genes, at least 50 genes, or all of the genes in Tables 3 or 4; (c) distinguishing a transplant excellent condition from a non-transplant excellent condition by applying a trained algorithm to the gene expression levels determined in (b), wherein the trained algorithm distinguishes a transplant excellent kidney from a non-transplant excellent condition, with a negative predictive value (NPV) of at least 60% or a positive predictive value (PPV) of at least 30%, or both; and (d) performing a kidney biopsy on the kidney transplant recipient with the detected non-transplant excellent condition in order to confirm that the kidney transplant recipient has the non-transplant excellent condition. In some embodiments, the method further comprises treating the non-transplant excellent condition detected by the kidney biopsy. In some embodiments, the treating the detected non-transplant excellent condition comprises administering an increased or decreased dose of the immunosuppressant drug to the kidney transplant recipient in order to treat the detected non-transplant excellent condition or administering a new immunosuppressant drug to the kidney transplant recipient in order to treat the detected non-transplant excellent condition. In some embodiments, the method further comprises for each of the at least five genes assigning the expression level of the gene in the kidney transplant recipient a value or other designation providing an indication whether the kidney transplant recipient has or is at risk of developing subAR, has or is at risk of having acute rejection (AR), has a well-functioning normal transplant (TX), or has or is at risk of having a non-transplant excellent condition, in any combination. In some embodiments, the method is repeated at different times on the kidney transplant recipient, such as in weekly, monthly, two-month, or three-month intervals following introduction of the transplant into the kidney transplant recipient. In some embodiments, the kidney transplant recipient is receiving a drug, and a change in the combined value or designation over time provides an indication of the effectiveness of the drug. In some embodiments, the kidney transplant recipient has undergone a kidney transplant within 1 month, 3 months, 1 year, 2 years, 3 years or 5 years of performing (a). In some embodiments, the sample from the kidney transplant recipient in (a) is a blood sample and comprises whole blood, peripheral blood, serum, plasma, PBLs, PBMCs, T cells, CD4 T cells CD8 T cells, or macrophages. In some embodiments, the method further comprises changing the treatment regime of the kidney transplant recipient responsive to the detecting step. In some embodiments, the kidney transplant recipient has received a drug before performing the methods, and the changing the treatment regime comprises administering an additional drug, administering a higher dose of the same drug, administering a lower dose of the same drug or stopping administering the same drug. In some embodiments, the method further comprises performing an additional procedure to detect subAR or risk thereof if the detecting in (c) provides an indication the kidney transplant recipient has or is at risk of subAR. In some embodiments, the additional procedure is a kidney biopsy. In some embodiments, (c) is performed by a computer. In some embodiments, the kidney transplant recipient is human. In some embodiments, for each of the at least five genes, (c) comprises comparing the expression level of the gene in the kidney transplant recipient to one or more reference expression levels of the gene associated with subAR, or lack of transplant rejection (TX). In some embodiments, the trained algorithm is applied to expression levels of fewer than 50 genes, fewer than 80 genes, fewer than 100 genes, fewer than 150 genes, fewer than 200 genes, fewer than 300 genes, fewer than 500 genes, or fewer than 1000 genes. In some embodiments, the expression levels of up to 100 or up to 1000 genes are determined. In some embodiments, the expression levels are determined at the mRNA level or at the protein level. In some embodiments, the expression levels are determined by quantitative PCR, hybridization to an array or sequencing.

In some aspects, the present disclosure provides for a method of treating a kidney transplant recipient on an immunosuppressant drug regimen comprising: (a) obtaining nucleic acids of interest, wherein the nucleic acids of interest comprise mRNA derived from a blood sample from the transplant recipient or cDNA complements of mRNA derived from a blood sample from the transplant recipient wherein the transplant recipient has stable serum creatinine; (b) performing a microarray assay or Next Generation sequencing assay on the nucleic acids of interest obtained in (a) to detect expression levels of at least five genes selected from Table 3, 4, 5, 6, or 8; (c) detecting subclinical acute rejection based on the expression levels detected in (b); and (d) administering a new immunosuppressant drug or a higher dose of the immunosuppressive drug to the transplant recipient in order to treat the subclinical acute rejection detected in (c). In some embodiments, the method further comprising contacting the nucleic acids of interest with probes, wherein the probes are specific for the at least five genes selected from Table 3, 4, 5, 6, or 8. In some embodiments, the method comprises terminating administration of the new immunosuppressive drug after repeating (a)-(c). In some embodiments, the method further comprises performing a microarray assay on the nucleic acids of interest obtained in (a).

In some aspects, the present disclosure provides for an automated, computer-implemented method of improved sample classification, comprising: (a) providing sample gene expression data derived from a blood sample from a kidney transplant recipient with a stable creatinine value; (b) providing at least a two-way classifier set, wherein the two-way classifier set is capable of distinguishing between a transplant excellent kidney and a kidney with sub-acute clinical rejection, wherein the classifier set comprises (i) at least 5 genes from Tables 5, 6, or 8; or (ii) at least 10 genes, at least 20 genes, at least 30 genes, at least 40 genes, at least 50 genes, or all of the genes in Table 5, 6, or 8; (c) applying the at least a two-way classifier set to the sample data using a classification rule or probability likelihood equation; and (d) using the classification rule or probability likelihood equation to output a classification for the sample wherein the classification classifies the sample as having a probability of having sub-clinical acute rejection with a with a negative predictive value (NPV) of at least 60% or a positive predictive value (PPV) of at least 30%, or both. In some embodiments, the classification is accomplished by DLDA, Nearest Centroid, Random Forest, or a Prediction Analysis of Microarrays. In some embodiments, the at least a two-way classifier set is obtained by ranking probe sets by p-value as to ability to distinguish between a transplant excellent kidney and a kidney with sub-acute clinical rejection. In some embodiments, the method comprises outputting a classification for the sample comprises transmission to an end user via a computer network. In some embodiments, the end user is a patient from which the blood sample was derived, a physician, or a caregiver of the patient from which the sample was derived. In some embodiments, the computer network is the Internet, an internet or extranet, or an intranet and/or extranet that is in communication with the Internet. In some embodiments, transmission to an end user comprises transmission to a web-based application on a local computer or a mobile application provided to a mobile digital processing device.

In some aspects, the present disclosure provides for an automated, computer-implemented method of improved sample classification, comprising: (a) providing sample gene expression data derived from a blood sample from a kidney transplant recipient with a stable creatinine value; (b) providing at least a two-way classifier set, wherein the two-way classifier set is capable of distinguishing between a transplant excellent kidney and a non-transplant excellent kidney, wherein the classifier set comprises (i) at least 5 genes from Table 3 or 4; or (ii) at least 10 genes, at least 20 genes, at least 30 genes, at least 40 genes, at least 50 genes, or all of the genes in Table 3 or 4; (c) applying the at least a two-way classifier set to the sample data using a classification rule or probability likelihood equation; and (d) using the classification rule or probability likelihood equation to output a classification for the sample, wherein the classification distinguishes a transplant excellent kidney from a non-transplant excellent kidney, wherein a non-transplant excellent kidney includes a kidney with acute rejection, sub-acute Rejection (subAR), acute dysfunction with no rejection, and kidney injury. In some embodiments, the classification is accomplished by DLDA, Nearest Centroid, Random Forest, or a Prediction Analysis of Microarrays. In some embodiments, the at least a two-way classifier set is obtained by ranking probe sets by p-value as to ability to distinguish between a transplant excellent kidney and a non-transplant excellent kidney. In some embodiments, outputting a classification for the sample comprises transmission to an end user via a computer network. In some embodiments, the end user is a patient from which the blood sample was derived, a physician, or a caregiver of the patient from which the sample was derived. In some embodiments, the computer network is the Internet, an internet and/or extranet, or an intranet and/or extranet that is in communication with the Internet. In some embodiments, transmission to an end user comprises transmission to a web-based application on a local computer or a mobile application provided to a mobile digital processing device.

In some aspects, the present disclosure provides for non-transitory computer-readable storage media encoded with a computer program including instructions executable by at least one processor to create an improved sample classification application comprising: (a) a software module for receiving sample data derived from a blood sample from a kidney transplant recipient with a stable creatinine value; (b) at least a two-way classifier stored on the media, wherein the two-way classifier set is capable of distinguishing between a transplant excellent kidney and a kidney with sub-acute clinical rejection, wherein the classifier set comprises (i) at least 5 genes from Table 5, 6, or 8; or (ii) at least 10 genes, at least 20 genes, at least 30 genes, at least 40 genes, at least 50 genes, or all of the genes in Table 5, 6, or 8; (c) a software module for applying the at least a two-way classifier set to the sample data using a classification rule or probability likelihood equation; and (d) a software module for using the classification rule or probability likelihood equation to output a classification for the sample wherein the classification classifies the sample as having a probability of having sub-clinical acute rejection with a negative predictive value (NPV) of at least 60% or a positive predictive value (PPV) of at least 30%, or both. In some embodiments, the at least a two-way classifier set is obtained by ranking probe sets by p-value as to ability to distinguish between a transplant excellent kidney and a kidney with sub-acute clinical rejection.

In some aspects, the present disclosure provides for a non-transitory computer-readable storage media encoded with a computer program including instructions executable by at least one processor to create an improved sample classification application comprising: (a) a software module for receiving sample data derived from a blood sample from a kidney transplant recipient with a stable creatinine value; (b) at least a two-way classifier stored on the media, wherein the two-way classifier set is capable of distinguishing between a transplant excellent kidney and a non-transplant excellent kidney, wherein the classifier set comprises (i) at least 5 genes from Table 3 or 4; or (ii) at least 10 genes, at least 20 genes, at least 30 genes, at least 40 genes, at least 50 genes, or all of the genes in Table 3 or 4; (c) a software module for applying the at least a two-way classifier set to the sample data using a classification rule or probability likelihood equation; and (d) a software module for using the classification rule or probability likelihood equation to output a classification for the sample wherein the classification distinguishes a transplant excellent kidney from a non-transplant excellent kidney, wherein a non-transplant excellent kidney includes a kidney with acute rejection, sub-acute Rejection (subAR), acute dysfunction with no rejection, and kidney injury. In some embodiments, the at least a two-way classifier set is obtained by ranking probe sets by p-value as to ability to distinguish between a transplant excellent kidney and a kidney with sub-acute clinical rejection.

In one aspect, the present disclosure provides a method of detecting a non-transplant excellent kidney in a human patient who has received a kidney transplant, the method comprising: (a) obtaining a blood sample, wherein the blood sample comprises mRNA from the kidney transplant recipient or DNA complements of mRNA from a kidney transplant recipient with a stable creatinine level; (b) performing a microarray assay or sequencing assay on a subset of the mRNA from the kidney transplant recipient with a stable creatinine level or the DNA complements of the mRNA from the kidney transplant recipient with a stable creatinine level in order to determine gene expression levels; and (c) detecting indicators of renal graft distress by applying a trained algorithm to the gene expression levels determined in (b), wherein the trained algorithm distinguishes a transplant excellent kidney from a non-transplant excellent kidney, wherein a non-transplant excellent kidney includes a kidney with acute rejection, subAR, acute dysfunction with no rejection, and kidney injury. In some embodiments, the trained algorithm performs a binary classification between a transplant excellent kidney and a non-transplant excellent kidney. In some embodiments, the gene expression levels comprise the levels of at least 5, at least 10, at least 20, at least 30, at least 40, or at least 52 genes selected from the group consisting of Table 1. In some embodiments, the gene expression levels comprise the levels of all the genes in Table 1. In some embodiments, the gene expression levels comprise the levels of at least at least 5, at least 10, at least 20, at least 30, at least 40, or 52 genes contacted by probes selected from the group consisting of Table 1. In some embodiments, the gene expression levels comprise the levels of all the genes contacted by probes selected from the group consisting of Table 1. In some embodiments, the gene expression levels comprise the levels of 5 or more genes selected from the group consisting of Table 2. In some embodiments, the gene expression levels comprise the levels of 5 or more genes contacted by probes selected from the group consisting of Table 2. In some embodiments, the gene expression levels comprise the levels of at least 5, at least 10, at least 20, at least 30, at least 40, or at least 52 genes selected from the group consisting of Table 3. In some embodiments, the gene expression levels comprise the levels of all the genes in Table 3. In some embodiments, the gene expression levels comprise the levels of at least at least 5, at least 10, at least 20, at least 30, at least 40, or 52 genes contacted by probes selected from the group consisting of Table 3. In some embodiments, the gene expression levels comprise the levels of all the genes contacted by probes selected from the group consisting of Table 3. In some embodiments, the gene expression levels comprise the levels of 5 or more genes selected from the group consisting of Table 4. In some embodiments, the gene expression levels comprise the levels of 5 or more genes contacted by probes selected from the group consisting of Table 4. In some embodiments, the gene expression levels comprise the levels of at least 5, at least 10, at least 20, at least 30, at least 40, or at least 52 genes contacted by probes selected from the group consisting of Table 4. In some embodiments, the gene expression levels comprise the levels of all the genes contacted by probes selected from the group consisting of Table 4.

In one aspect, the present disclosure provides a method of detecting subAR in a kidney transplant recipient, the method comprising: (a) obtaining a blood sample, wherein the blood sample comprises mRNA from the kidney transplant recipient or DNA complements of mRNA from a kidney transplant recipient with a stable creatinine level; (b) performing a microarray assay or sequencing assay on a subset of the mRNA from the kidney transplant recipient with a stable creatinine level or the DNA complements of the mRNA from the kidney transplant recipient with a stable creatinine level in order to determine gene expression levels, wherein the gene expression levels comprise the levels of (i) at least 5, at least 10, at least 15, at least 19, at least 20, at least 25, at least 30, at least 35, at least 40, or at least 50 genes selected from the group consisting of Table 5, (ii) 5, at least 10, at least 15, at least 19, at least 20, at least 25, at least 30, at least 35, at least 40, or at least 50 genes contacted by probes selected from the group consisting of Table 5, (iii) 5 or more genes selected from the group consisting of Table 6, (iv) five or more genes contacted by probes selected from the group consisting of Table 6, or (v) all of the genes in Table 8; and (c) detecting subAR by applying a trained algorithm to the gene expression levels determined in (b), wherein the trained algorithm distinguishes at least a transplant excellent kidney from a subAR kidney, wherein the kidney transplant recipient has a normal or stable creatinine level. In some embodiments, the gene expression levels comprise the levels of 5, at least 10, at least 15, at least 19, at least 20, at least 25, at least 30, at least 35, at least 40, or at least 50 genes selected from the group consisting of Table 5. In some embodiments, the gene expression levels comprise the levels of 5, at least 10, at least 15, at least 19, at least 20, at least 25, at least 30, at least 35, at least 40, or at least 50 genes contacted by probes selected from the group consisting of Table 5. In some embodiments, the gene expression levels comprise the levels of five or more genes selected from the group consisting of Table 6. In some embodiments, the gene expression levels comprise the levels of five or more genes contacted by probes selected from the group consisting of Table 6. In some embodiments, the gene expression levels comprise the levels of all the genes in Table 8. In some embodiments, the trained algorithm distinguishes a subAR kidney from a transplant excellent kidney with an NPV of greater than 78%. In some embodiments, the trained algorithm distinguishes a subAR kidney from a transplant excellent kidney with a PPV of greater than 47%. In some embodiments, the kidney transplant recipient has a normal or stable creatinine level. In some embodiments, the kidney transplant recipient has a serum creatinine level of less than less than 2.3 mg/dL. In some embodiments, the kidney transplant recipient is on an immunosuppressant drug, and the method further comprises administering an increased dose of the immunosuppressant drug to the kidney transplant recipient in order to treat or prevent the subAR detected in (c) or administering a new immunosuppressant drug to the human subject in order to treat or prevent the subAR prognosed, diagnosed or monitored in the transplanted kidney of the human subject in (c). In some embodiments, the immunosuppressant drug or the new immunosuppressant drug is a calcineurin inhibitor. In some embodiments, the immunosuppressant drug or the new immunosuppressant drug is an mTOR inhibitor. In some embodiments, the immunosuppressant drug or new immunosuppressant drug is selected from the group consisting of azathioprine, leflunomide, mycophenolic acid, mycophenolate mofetil, prednisolone, hydrocortisone, basiliximab, alemtuzumab, daclizumab, belatacept, orthoclone, anti-thymocyte globulin, anti-lymphocyte globulin, an anti-proliferative drug, and an anti-T cell antibody.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7 is a chart showing external validation of the subAR gene expression profile classifier biomarker on 138 (left) and 129 (subset of 138—right) NU paired sample (peripheral blood and surveillance biopsy) samples cohorts.

DETAILED DESCRIPTION

I. Overview

The present disclosure provides unique sets of gene expression markers that can be used to detect certain kidney transplant conditions without the need for a biopsy. Particularly, the present disclosure provides unique sets of gene expression markers that can be used to detect non-normal transplant status and/or immune rejection with higher sensitivity in comparison to traditional laboratory methods (e.g. serum creatinine, eGFR). In some cases, the methods enable detection of subclinical acute rejection ("subAR"), an immune rejection condition characterized by relatively stable or normal creatinine levels in the blood. In some cases, the methods enable detection of non-transplant excellent states ("non-TX") of a kidney allograft, which is a category that encompasses various conditions (acute rejection, sub-acute rejection/subAR, acute dysfunction with no rejection, and kidney injury) requiring follow-up by medical practitioners, enabling prioritization of patients that require additional diagnostic or treatment procedures.

Use of some of the sets of gene expression markers provided herein may aid in the detection of "non-normal" or "abnormal" transplant status or immune activation with reduced false negative rates. This is because the designation of "abnormal" as used in some of the tests provided herein encompasses a wide range of adverse transplant conditions including acute rejection (AR), acute dysfunction without rejection (ADNR), subAR and kidney injury. Because the unique sets of gene expression markers provided herein are suitable for detection of conditions from blood samples, they are particularly useful for the evaluation of transplant status in a minimally-invasive manner (e.g. without surgical excision of tissue) and are amenable to serial monitoring. The present methods are also superior to traditional blood tests such as urine protein or serum creatinine levels as such tests often require a relatively advanced stage of disease capable of significantly impairing kidney function before registering as positive.

Figure 1:
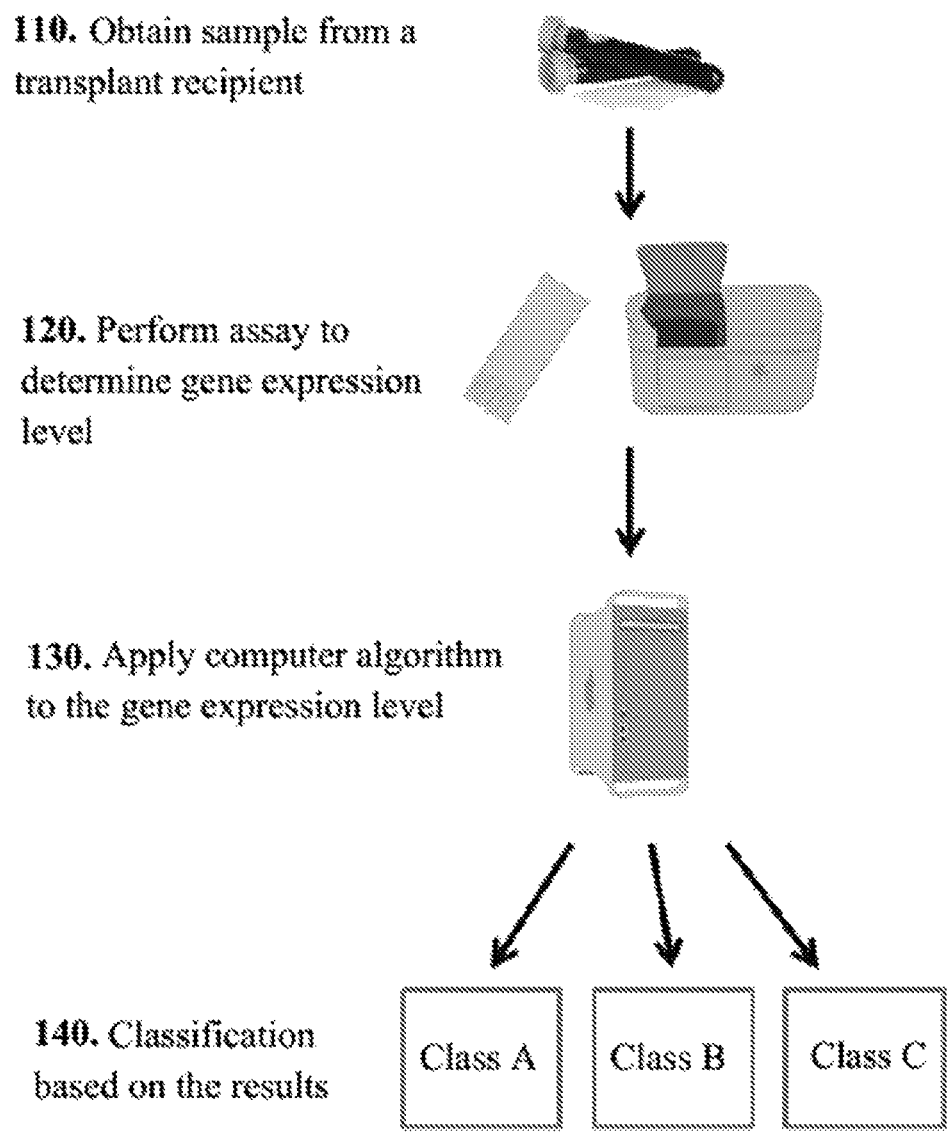
FIG. 1 is a flowchart giving a schematic overview of how diagnostic methods according to the disclosure can be used to classify samples from transplant recipients.
Figure 6:
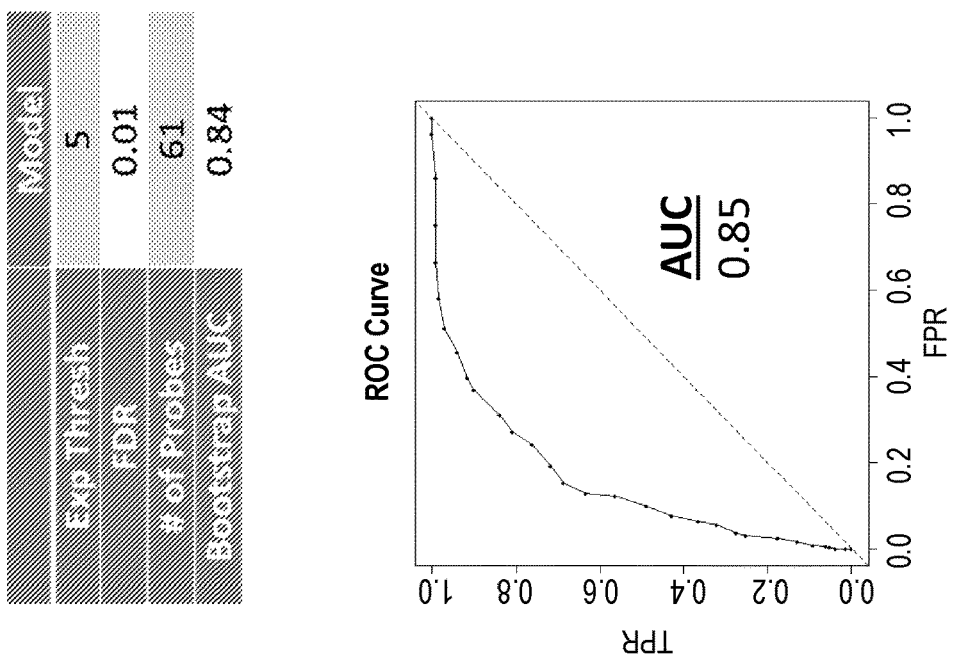
FIG. 6 is an ROC curve and accompanying table illustrating the refinement process for the subAR classifier biomarker based on the 530 CTOT-08 paired peripheral blood and surveillance biopsy samples cohort from the CTOT "discovery" cohort.
Figure 10:
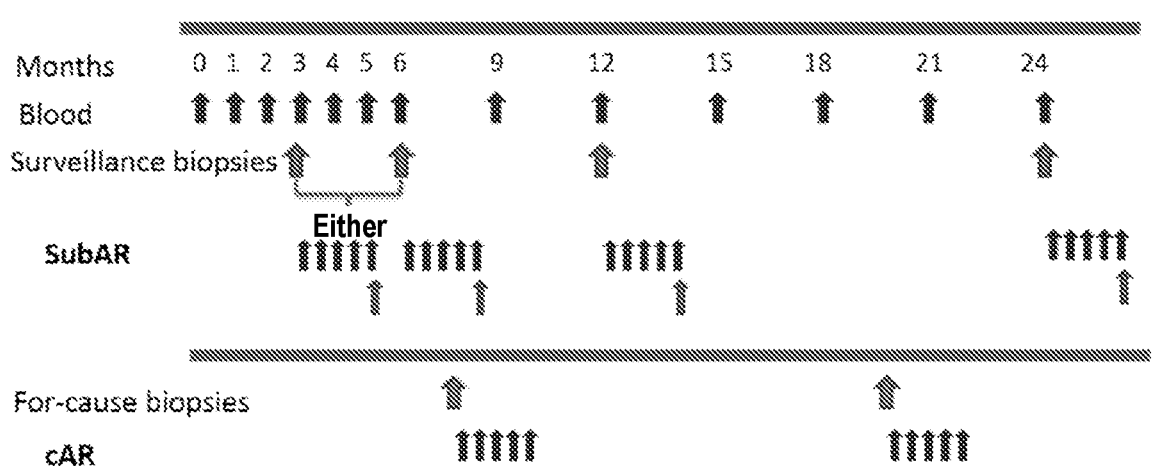
FIG. 10 is a diagram showing the CTOT-08 study design described in Example 5. Subjects had serial blood sampling (red arrows) coupled with periodic surveillance kidney biopsies (upper blue arrows). If subjects were diagnosed with subclinical acute rejection (subAR), they had more frequent blood sampling (lower red arrows) and a follow up biopsy 8 weeks later (skinny blue arrows). If subjects presented with renal dysfunction, they underwent "for cause" biopsies. Episodes of clinical acute rejection also had more frequent blood sampling for 8 weeks, but no follow up biopsy. All patients were scheduled for a biopsy at 24 months post-transplant as part of the clinical composite endpoint (CCE).
Figure 11:
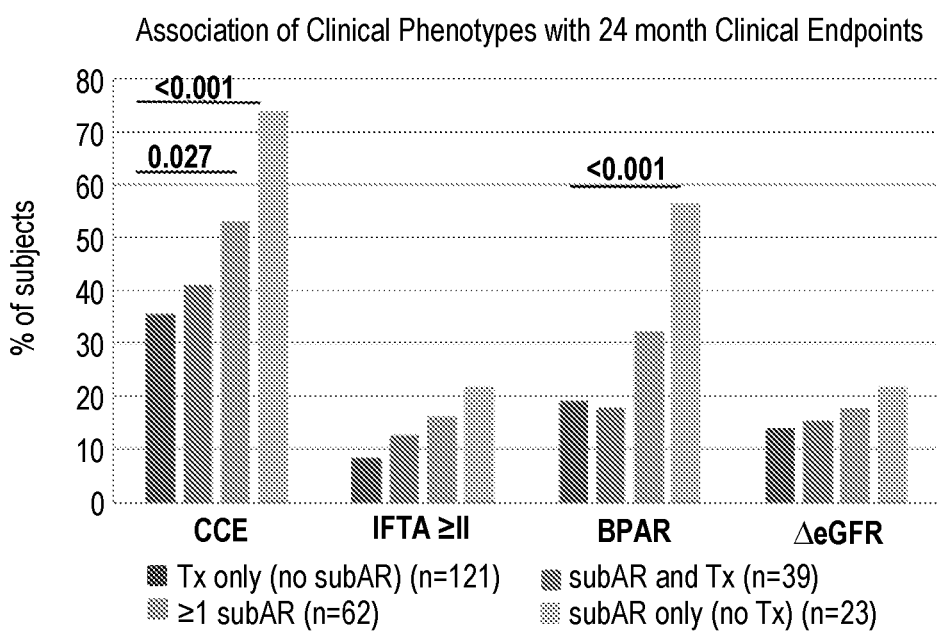
FIG. 11 is a chart depicting association of clinical phenotype with 24 month clinical composite endpoints. Shown are the percentage of subjects who reached an endpoint (either the composite endpoint—CCE) or each individual component of the CCE (Grade 2 IFTA on 24-month biopsy, any episode of biopsy proven acute rejection (BPAR), or drop in GFR >10 ml/min/1.73 m2 between months 4 and 24). Subjects are divided by their clinical phenotypes (those with only TX on biopsies (blue bars/first bars in each group), those with either subAR or TX (orange bars/second bars in each group), subjects that had at least one episode of subAR (grey bars, third bars in each group), and then subjects that only had subAR (yellow bars, fourth bars in each group) on surveillance biopsies.
Figure 12:
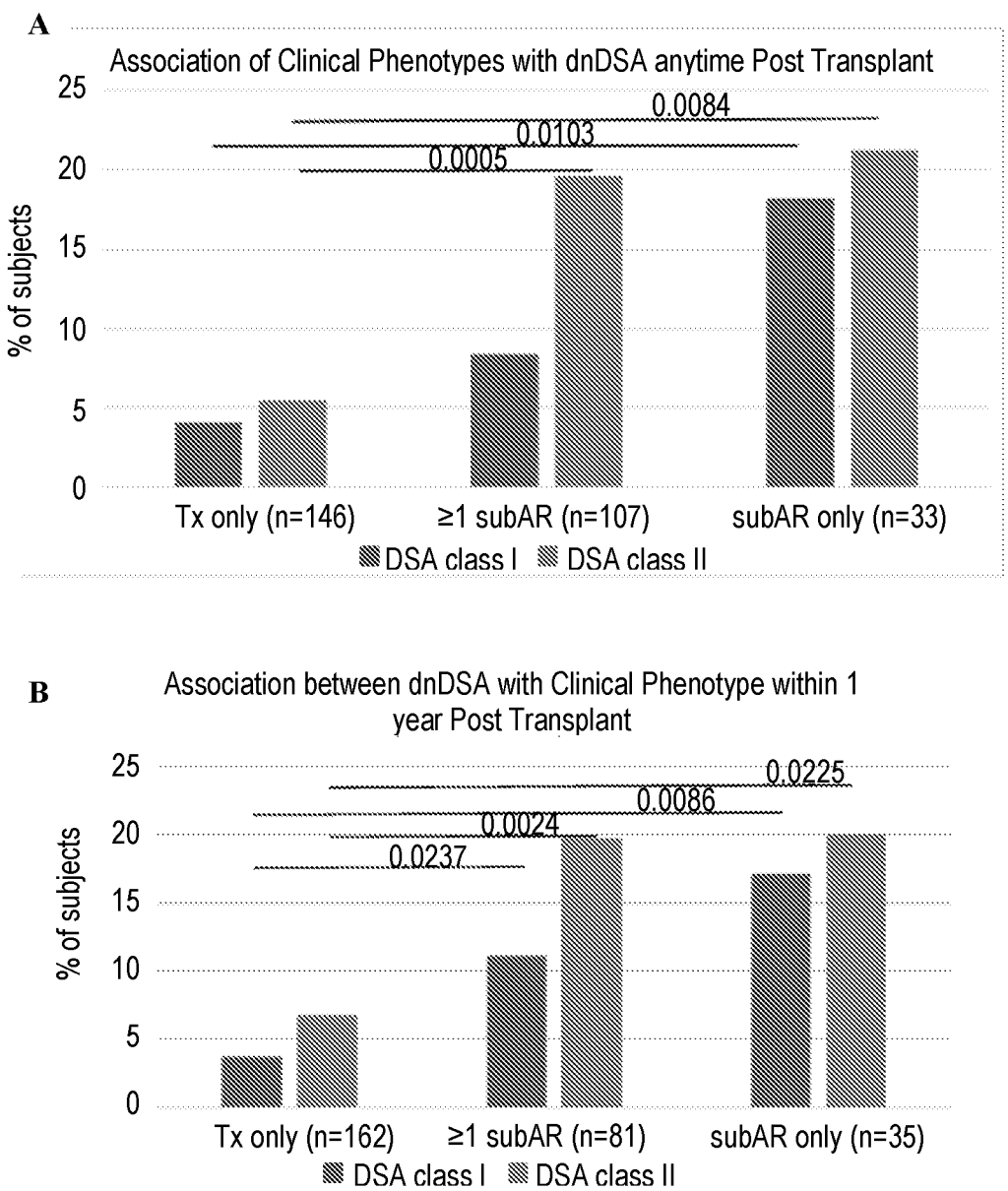
FIG. 12 depicts the association of clinical phenotypes with dnDSA (de novo donor-specific antibody) anytime post-transplant. Panel A (top) shows the percentage of subjects that developed de novo donor specific antibodies (dnDSA) at any time during the study, either Class I (blue bars) or Class II (orange bars), based on their clinical phenotypic group in the 24-month trial (subjects that had TX only on biopsies, at least one episode of subAR on biopsy, or only subAR on surveillance biopsy). Panel B (bottom) shows a similar depiction to Panel 1 with the association between dnDSA and clinical phenotypes but limited to biopsy results obtained in the first year post transplant.
Figure 13:
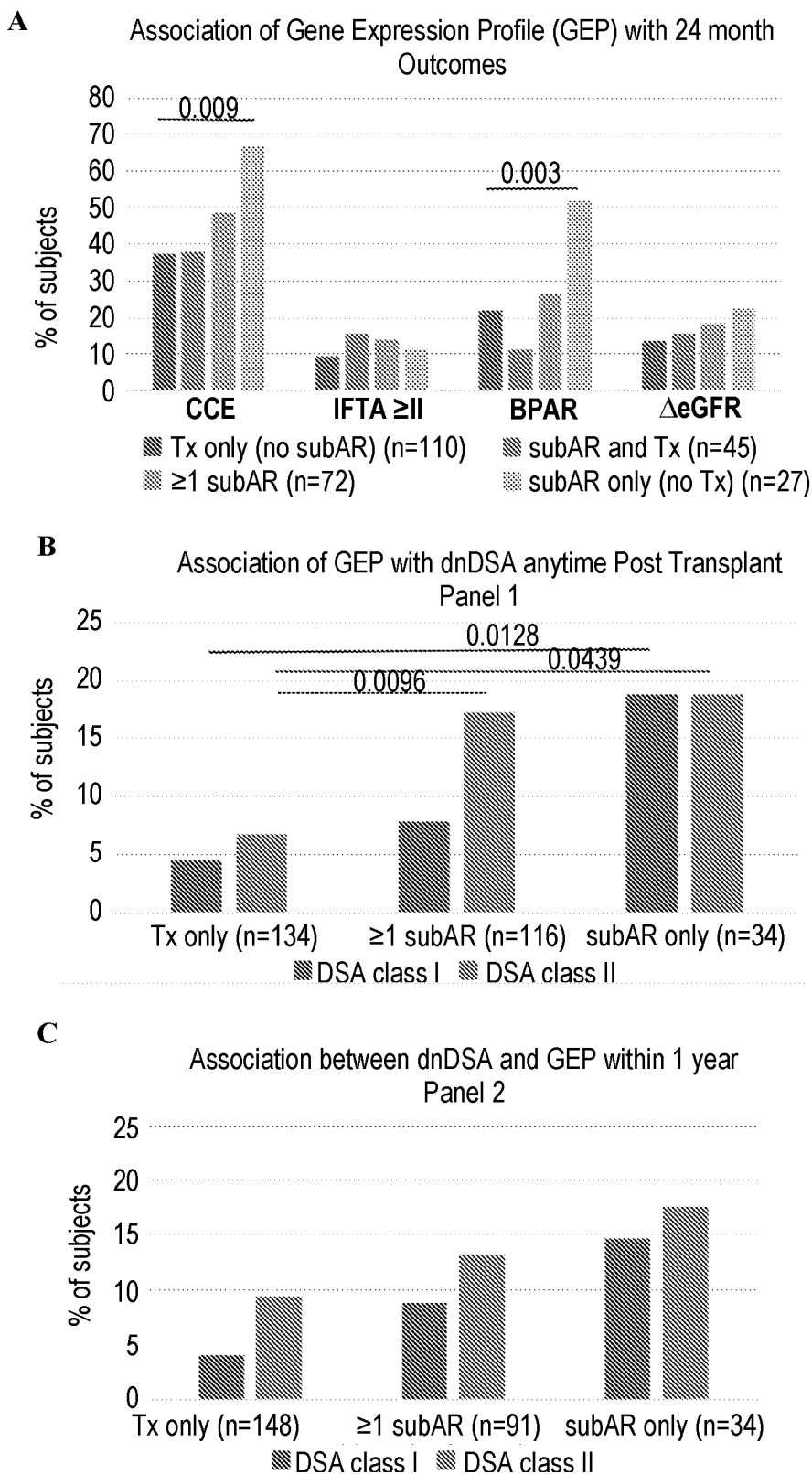
FIG. 13 depicts the association of the subAR gene expression profile (GEP) developed in Example 5 with 24-month outcomes and dnDSA. Panel A (top) shows the association of the subAR GEP with 24 month outcomes. Shown are the percentage of subjects who reached an endpoint (either the composite endpoint—CCE) or each individual component of the CCE (Grade 2 IFTA on 24-month biopsy, any episode of biopsy proven acute rejection (BPAR), or drop in GFR >10 ml/min/1.73 m2 between months 4 and 24). Subjects are divided by their Gene Expression Profile (GEP) tests results. Those that had only TX on GEP (blue bars/first bar in each group), those with either subAR or TX (orange bars/second bar in each group), subjects that had at least test with subAR (grey bars/third bar in each group), and then subjects that only had subAR tests (yellow bars/fourth bar in each group). Panel B (middle) shows the association between the subAR gene expression profile (GEP) test and the development of de novo donor specific antibodies (dnDSA) anytime post-transplant. This includes GEP tests done any time in the 24-month study period. Shown are the percentage of subjects that developed dnDSA, both Class I (blue bars/first bar in each group) and Class II (orange bars/second bar in each group) grouped based on their GEP tests. The subject groups are those with only TX blood tests, at least one subAR blood test, or only subAR blood tests. All blood tests were paired with surveillance biopsies. Panel C (bottom) shows a similar analysis to Panel B (association between GEP test and the development of de novo donor specific antibodies dnDSA), except that it is limited to the first year post transplant.

An overview of certain methods according to the disclosure is provided in FIG. 1. In some instances, a method comprises obtaining a sample from a transplant recipient with normal or stable renal function in a minimally invasive manner (110), such as via a blood draw. The sample may comprise gene expression products (e.g., mRNA isolated from whole blood) associated with the status of the transplant (e.g., subAR, non-Transplant excellent, Transplant excellent, no subAR). In some instances, the method may involve reverse-transcribing RNA within the sample to obtain cDNA that can be analyzed using the methods described herein. The method may also comprise assaying the level of the gene expression products (or the corresponding DNA) using methods such as microarray or sequencing technology (120). The method may then comprise applying an algorithm to the assayed gene expression levels (130) in order to detect subAR or non-TX vs TX. The algorithm may involve the levels of particular sets of genes, such as at least 52 genes selected from the group consisting of Tables 1, 2, 3, 4, 5, 6 and/or 8 below, or at least 5 genes contacted by probes selected from the group consisting of Tables 1, 2, 3, 4, 5, 6 and/or 8. If the transplant recipient is designated as either subAR or non-TX, further testing may be performed in order to ascertain the transplant status, such as assessing serum creatinine level, assessing eGFR, urine protein levels, and/or performing a kidney biopsy. Upon further testing of the recipient designated as non-TX, the immunosuppression regimen may be adjusted upward or downward, or new immunosuppressants or other drugs may be administered to treat the transplant status. If the transplant recipient is designated as subAR, the subject's immunosuppression regimen may be adjusted, or additional immunosuppressants may be administered to treat or prevent the immune rejection occurring in the transplanted organ; alternatively, a biomarker-prompted biopsy may be obtained and the test repeated if needed after necessary intervention. Alternatively, a biomarker-prompted abstention from biopsy may occur for a period of time (e.g. 1 week, 1 month, 2 months, 3 months). The design of a study to identify blood gene expression markers for identifying diagnostic conditions observable by biopsy described herein is illustrated in FIG. 10, which depicts the study design for the CTOT-08 study, and Table 7, which illustrates subject characteristics. Subjects in the study underwent serial blood sampling (dark gray arrows) coupled with periodic kidney biopsies ("surveillance biopsies") (light gray arrows). Subjects diagnosed with subclinical acute rejection ("subAR") had more frequent blood sampling (lower dark gray arrows), and a follow-up biopsy 8 weeks later (skinny light gray arrows). Subjects presenting with renal dysfunction underwent "for-cause" biopsies (lowest light gray arrows). Episodes of clinical acute rejection ("cAR") also had more frequent blood sampling for 8 weeks, but no follow-up biopsy. All patients were scheduled for a biopsy at 24 months post-transplant as part of the clinical composite endpoint (CCE). Clinical endpoints used to inform the utility of biomarker panels described herein are illustrated in FIG. 11, which depicts the association of clinical phenotype with 24 month clinical composite endpoints. The chart illustrates the percentage of subjects who reached an endpoint (either the clinical composite endpoint—CCE) or each individual component of the CCE (Grade 2 IFTA on 24-month biopsy ["IFTA≥II" ]; any episode of biopsy proven acute rejection ["BPAR" ]; or drop in GFR >10 ml/min/1.73 m2 between months 4 and 24 ["AeGFR" ]). Subjects are divided by their clinical phenotypes (those with only TX on biopsies (blue bars/first bars in each group), those with either subAR or TX (orange bars/second bars in each group), subjects that had at least one episode of subAR (grey bars, third bars in each group), and then subjects that only had subAR (yellow bars, fourth bars in each group) on surveillance biopsies. FIG. 12A-B depicts the association of clinical phenotypes with de novo donor-specific antibody ("dnDSA") anytime post-transplant. FIG. 12A (top panel) shows the percentage of subjects that developed de novo donor specific antibodies (dnDSA) at any time during the study, either Class I (left-hand bars of each group/dark gray) or Class II (right-hand bars of each group/light gray), based on their clinical phenotypic group in the 24-month trial (subjects that had TX only on biopsies, at least one episode of subAR on biopsy, or only subAR on surveillance biopsy). FIG. 12B (bottom panel) shows a similar depiction to FIG. 12A with the association between dnDSA and clinical phenotypes but limited to biopsy results obtained in the first year post transplant. FIG. 13A-C depicts the association of the subclinical acute rejection ("subAR") gene expression profile (GEP) developed herein with 24-month outcomes and dnDSA. FIG. 13A (top panel) shows the association of the subAR GEP with 24 month outcomes. Shown are the percentage of subjects who reached an endpoint (either the composite endpoint—CCE) or each individual component of the CCE (Grade 2 IFTA on 24-month biopsy ["IFTA≥II" ]; any episode of biopsy proven acute rejection ["BPAR" ]; or drop in GFR >10 ml/min/1.73 m2 between months 4 and 24 ["AeGFR" ]). Subjects are divided by their Gene Expression Profile (GEP) tests results. Those that had only TX on GEP (blue bars/first bar in each group), those with either subAR or TX (orange bars/second bar in each group), subjects that had at least test with subAR (grey bars/third bar in each group), and then subjects that only had subAR tests (yellow bars/fourth bar in each group). FIG. 13B (middle panel) shows the association between the subAR gene expression profile (GEP) test and the development of de novo donor specific antibodies (dnDSA) anytime post-transplant. This includes GEP tests done any time in the 24-month study period. Shown are the percentage of subjects that developed dnDSA, both Class I (blue bars/first bar in each group) and Class II (orange bars/second bar in each group) grouped based on their GEP tests. The subject groups are those with only TX blood tests, at least one subAR blood test, or only subAR blood tests. All blood tests were paired with surveillance biopsies. FIG. 13C (bottom panel) shows a similar analysis to Panel B (association between GEP test and the development of de novo donor specific antibodies dnDSA), except that it is limited to the first year post transplant. FIG. 6 depicts the receiver operating characteristic (ROC) curve illustrating the process for identifying subAR classifier biomarkers. The 530 CTOT-08 paired peripheral blood and surveillance biopsy samples cohort from the CTOT "discovery" cohort were used.

II. Definitions

Unless defined otherwise, all technical and scientific terms used herein have the same meaning as commonly understood by those of ordinary skill in the art to which this invention pertains. In addition, the following definitions are provided to assist the reader in the practice of the invention.

The term "or" as used herein and throughout the disclosure is intended as an inclusive "or", meaning "and/or".

Transplantation is the transfer of tissues, cells or an organ from a donor into a recipient. If the donor and recipient as the same person, the graft is referred to as an autograft and as is usually the case between different individuals of the same species an allograft. Transfer of tissue between species is referred to as a xenograft.

A biopsy is a specimen obtained from a living patient for diagnostic or prognostic evaluation. Kidney biopsies can be obtained with a needle.

An average value can refer to any of a mean, median or mode.

As used herein, the term TX or "transplant excellent" is used to signify a condition wherein the patient does not exhibit symptoms or test results of organ dysfunction or rejection; in the TX condition the transplant is considered a normal functioning transplant. A TX patient has normal histology on a surveillance biopsy (e.g. no evidence of rejection—Banff i=0 and t=0, g=0, ptc=0; ci=0 or 1 and ct=0 or 1) and stable renal function (e.g. serum creatinine <2.3 mg/dl and <20% increase in creatinine compared to a minimum of 2-3 prior values over a mean period and range of 132 and 75-187 days). In contrast, Non-TX encompasses conditions as acute rejection, subclinical acute rejection, acute dysfunction with no rejection, and kidney injury. In some embodiments, non-TX encompasses conditions of renal graft distress.

As used herein, the term "subclinical acute rejection" (also "subAR") refers to histologically defined acute rejection—particularly, histologically defined acute cellular rejection—characterized by tubule-interstitial mononuclear infiltration identified from a biopsy specimen (e.g. histology on a surveillance biopsy consistent with acute rejection such as ≥Banff borderline cellular rejection and/or antibody mediated rejection), but without concurrent functional deterioration (e.g. serum creatinine <2.3 mg/dl and <20% increase in creatinine compared to a minimum of 2-3 prior values over a mean period and range of 132 and 75-187 days). Some instances of subAR may represent the beginning or conclusion of an alloimmune infiltrate diagnosed fortuitously by protocol sampling, and some episodes of clinical rejection may actually represent subAR with an alternative cause of functional decline, such as concurrent calcineurin inhibitor (CNI) nephrotoxicity. A subAR subject may have normal and stable organ function. SubAR is distinguished from acute rejection, as acute rejection is characterized by acute renal impairment. The differences between subAR and acute rejection (which may appear histologically indistinguishable on a limited sample) can be explained by real quantitative differences of renal cortex affected, qualitative differences (such as increased perforin, granzyme, c-Bet expression or macrophage markers), or by an increased ability of the allograft to withstand immune injury ('accommodation'). SubAR is often diagnosed only on biopsies taken as per protocol at a fixed time after transplantation, rather than driven by clinical indication. Its diagnosis cannot rely on traditional kidney function measurements like serum creatinine and glomerular filtration rates.

Acute rejection (AR) or clinical acute rejection may occur when transplanted tissue is rejected by the recipient's immune system, which damages or destroys the transplanted tissue unless immunosuppression is achieved. T-cells, B-cells and other immune cells as well as possibly antibodies of the recipient may cause the graft cells to lyse or produce cytokines that recruit other inflammatory cells, eventually causing necrosis of allograft tissue. In some instances, AR may be diagnosed by a biopsy of the transplanted organ. In the case of kidney transplant recipients, AR may be associated with an increase in serum creatinine levels. AR more frequently occurs in the first three to 12 months after transplantation but there is a continued risk and incidence of AR for the first five years post-transplant and whenever a patient's immunosuppression becomes inadequate for any reason for the life of the transplant.

A gene expression level is associated with a particular phenotype e.g., presence of subAR or AR if the gene is differentially expressed in a patient having the phenotype relative to a patient lacking the phenotype to a statistically significant extent. Unless otherwise apparent from the context a gene expression level can be measured at the mRNA and/or protein level.

A probe or polynucleotide probe is a nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." A probe can include natural (e.g., A, G, C, U, or T) or modified bases (e.g., 7-deazaguanosine, inosine.). A probe can be an oligonucleotide and may be a single-stranded DNA or RNA. Polynucleotide probes can be synthesized or produced from naturally occurring polynucleotides. In addition, the bases in a probe can be joined by a linkage other than a phosphodiester bond, so long as it does not interfere with hybridization. Thus, probes can include, for example, peptide nucleic acids in which the constituent bases are joined by peptide bonds rather than phosphodiester linkages. Some probes can have leading and/or trailing sequences of non-complementarity flanking a region of complementarity.

A perfectly matched probe has a sequence perfectly complementary to a particular target sequence. The probe is typically perfectly complementary to a portion (subsequence) of a target sequence.

Statistical significance means p<0.05 or <0.01 or even <0.001 level.

As used herein "obtaining a sample" includes obtaining a sample directly or indirectly. In some embodiments, the sample is taken from the subject by the same party (e.g. a testing laboratory) that subsequently acquires biomarker data from the sample. In some embodiments, the sample is received (e.g. by a testing laboratory) from another entity that collected it from the subject (e.g. a physician, nurse, phlebotomist, or medical caregiver). In some embodiments, the sample is taken from the subject by a medical professional under direction of a separate entity (e.g. a testing laboratory) and subsequently provided to said entity (e.g. the testing laboratory). In some embodiments, the sample is taken by the subject or the subject's caregiver at home and subsequently provided to the party that acquires biomarker data from the sample (e.g. a testing laboratory).

III. Patient Populations

Preferred subjects for application of methods according to the disclosure are transplant recipients. A transplant recipient may be a recipient of a solid organ or a fragment of a solid organ such as a kidney. Preferably, the transplant recipient is a kidney transplant or allograft recipient. In some instances, the transplant recipient may be a recipient of a tissue or cell. In some particular examples, the transplanted kidney may be a kidney differentiated in vitro from pluripotent stem cell(s) (e.g., induced pluripotent stem cells or embryonic stem cells).

The methods are particularly useful on human subjects who have undergone a kidney transplant although can also be used on subjects who have undergone other types of transplant (e.g., heart, liver, lungs, stem cell) or on non-humans who have undergone kidney or other transplant.

The donor organ, tissue, or cells may be derived from a subject who has certain similarities or compatibilities with the recipient subject. For example, the donor organ, tissue, or cells may be derived from a donor subject who is age-matched, ethnicity-matched, gender-matched, blood-type compatible, or HLA-type compatible with the recipient subject. In some circumstances, the donor organ, tissue, or cells may be derived from a donor subject that has one or more mismatches in age, ethnicity, gender, blood-type, or HLA markers with the transplant recipient due to organ availability. The organ may be derived from a living or deceased donor.

The term subject or patient can include human or non-human animals. Thus, the methods and described herein are applicable to both human and veterinary disease and animal models. Preferred subjects are "patients," i.e., living humans that are receiving medical care for a disease or condition. This includes persons with no defined illness who are being investigated for signs of pathology. The term subject or patient can include transplant recipients or donors or healthy subjects. The methods can be particularly useful for human subjects who have undergone a kidney transplant although they can also be used for subjects who have gone other types of transplant (e.g., heart, liver, lung, stem cell, etc.). The subjects may be mammals or non-mammals. Preferably the subject is a human, but in some cases the subject is a non-human mammal, such as a non-human primate (e.g., ape, monkey, chimpanzee), cat, dog, rabbit, goat, horse, cow, pig, rodent, mouse, SCID mouse, rat, guinea pig, or sheep. The subject may be male or female; the subject may be and, in some cases, the subject may be an infant, child, adolescent, teenager or adult. In some cases, the methods provided herein are used on a subject who has not yet received a transplant, such as a subject who is awaiting a tissue or organ transplant. In other cases, the subject is a transplant donor. In some cases, the subject has not received a transplant and is not expected to receive such transplant. In some cases, the subject may be a subject who is suffering from diseases requiring monitoring of certain organs for potential failure or dysfunction. In some cases, the subject may be a healthy subject.

In various embodiments, the subjects suitable for methods of the invention are patients who have undergone an organ transplant within 6 hours, 12 hours, 1 day, 2 days, 3 days, 4 days, 5 days, 10 days, 15 days, 20 days, 25 days, 1 month, 2 months, 3 months, 4 months, 5 months, 7 months, 9 months, 11 months, 1 year, 2 years, 4 years, 5 years, 10 years, 15 years, 20 years or longer of prior to receiving a classification obtained by the methods disclosed herein, such as detection of subAR.

Often, the subject is a patient or other individual undergoing a treatment regimen, or being evaluated for a treatment regimen (e.g., immunosuppressive therapy). However, in some instances, the subject is not undergoing a treatment regimen. A feature of the graft tolerant phenotype detected or identified by the subject methods is that it is a phenotype which occurs without immunosuppressive therapy, e.g., it is present in a subject that is not receiving immunosuppressive therapy.

The methods of the disclosure are suitable for detecting non-TX or subAR conditions in transplant patients, and are particularly useful for detecting non-TX or subAR without relying on a histologic analysis or obtaining a biopsy.

In some instances, a normal serum creatinine level and/or a normal estimated glomerular filtration rate (eGFR) may indicate or correlate with healthy transplant (TX) or sub-clinical rejection (subAR). For example, typical reference ranges for serum creatinine are 0.5 to 1.0 mg/dL for women and 0.7 to 1.2 mg/dL for men, though typical kidney transplant patients have serum creatinine concentrations in the 0.8 to 1.5 mg/dL range for women and 1.0 to 1.9 mg/dL range for men. This may be due to the fact that most kidney transplant patients have a single kidney. In some instances, the trend of serum creatinine levels over time can be used to evaluate the recipient's organ function. This is why it may be important to consider both "normal" serum creatinine levels and "stable" serum creatinine levels in making clinical judgments, interpreting testing results, deciding to do a biopsy or making therapy change decisions including changing immunosuppressive drugs. For example, the transplant recipient may show signs of a transplant dysfunction or rejection as indicated by an elevated serum creatinine level and/or a decreased eGFR. In some instances, a transplant subject with a particular transplant condition (e.g., subAR, non-TX, TX, etc.) may have an increase of a serum creatinine level of at least 0.1 mg/dL, 0.2 mg/dL, 0.3 mg/dL, 0.4 mg/dL, 0.5 mg/dL, 0.6 mg/dL, 0.7 mg/dL 0.8 mg/dL, 0.9 mg/dL, 1.0 mg/dL, 1.1 mg/dL, 1.2 mg/dL, 1.3 mg/dL, 1.4 mg/dL, 1.5 mg/dL, 1.6 mg/dL, 1.7 mg/dL, 1.8 mg/dL, 1.9 mg/dL, 2.0 mg/dL, 2.1 mg/dL, 2.2 mg/dL, 2.3 mg/dL, 2.4 mg/dL, 2.5 mg/dL, 2.6 mg/dL, 2.7 mg/dL, 2.8 mg/dL, 2.9 mg/dL, 3.0 mg/dL, 3.1 mg/dL, 3.2 mg/dL, 3.3 mg/dL, 3.4 mg/dL, 3.5 mg/dL, 3.6 mg/dL, 3.7 mg/dL, 3.8 mg/dL, 3.9 mg/dL, or 4.0 mg/dL. In some instances, a transplant subject with a certain transplant condition (e.g., subAR, non-TX, TX, etc.) may have an increase of a serum creatinine level of at least 10%, 20%, 30%, 40%, 50%, 60%, 70%, 80%, 90%, or 100% from baseline. In some instances, a transplant subject with a certain transplant condition (e.g., subAR, non-TX, TX, etc.) may have an increase of a serum creatinine level of at least 1-fold, 2-fold, 3-fold, 4-fold, 5-fold, 6-fold, 7-fold, 8-fold, 9-fold, or 10-fold from baseline. In some cases, the increase in serum creatinine (e.g., any increase in the concentration of serum creatinine described herein) may occur over about 0.25 days, 0.5 days, 0.75 days, 1 day, 1.25 days, 1.5 days, 1.75 days, 2.0 days, 3.0 days, 4.0 days, 5.0 days, 6.0 days, 7.0 days, 8.0 days, 9.0 days, 10.0 days, 15 days, 30 days, 1 month, 2 months, 3 months, 4 months, 5 months, or 6 months, or more. In some instances, a transplant subject with a particular transplant condition (e.g., subAR, non-TX, TX, etc.) may have a decrease of a eGFR of at least 10%, 20%, 30%, 40%, 50%, 50%, 70%, 80%, 90%, or 100% from baseline. In some cases, the decrease in eGFR may occur over 0.25 days, 0.5 days, 0.75 days, 1 day, 1.25 days, 1.5 days, 1.75 days, 2.0 days, 3.0 days, 4.0 days, 5.0 days, 6.0 days, 7.0 days, 8.0 days, 9.0 days, 10.0 days, 15 days, 30 days, 1 month, 2 months, 3 months, 4 months, 5 months, or 6 months, or more. In some instances, diagnosing, predicting, or monitoring the status or outcome of a transplant or condition comprises determining transplant recipient-specific baselines and/or thresholds.

As such, the methods of the invention can be used in patients who have normal and stable creatinine levels to diagnose or prognose hidden subAR without depending on invasive biopsies. In some cases, the serum creatinine levels of the transplant recipient are stable over at least 10 days, 20 days, 30 days, 40 days, 50 days, 60 days, 90 days, 100 days, 200 days, 300 days, 400 days or longer. In some cases, the transplant recipient has a serum creatinine level of less than 0.2 mg/dL, less than 0.3 mg/dL, less than 0.4 mg/dL, less than 0.5 mg/dL, less than 0.6 mg/dL, less than 0.7 mg/dL less than 0.8 mg/dL, less than 0.9 mg/dL, less than 1.0 mg/dL, less than 1.1 mg/dL, less than 1.2 mg/dL, less than 1.3 mg/dL, 1.4 mg/dL, less than 1.5 mg/dL, less than 1.6 mg/dL, less than 1.7 mg/dL, less than 1.8 mg/dL, less than 1.9 mg/dL, less than 2.0 mg/dL, less than 2.1 mg/dL, less than 2.2 mg/dL, less than 2.3 mg/dL, less than 2.4 mg/dL, less than 2.5 mg/dL, less than 2.6 mg/dL, less than 2.7 mg/dL, less than 2.8 mg/dL, less than 2.9 mg/dL, or less than 3.0 mg/dL.

IV. Samples

The methods of the disclosure involve the classification of subjects into one of multiple categories (e.g. TX, non-TX, subAR, AR) based on testing biomolecules from samples derived from the subject. The preferred sample type for analysis is a blood sample, which refers to whole blood or fractions thereof, such as plasma, lymphocytes, peripheral blood lymphocytes (PBLs), peripheral blood mononuclear cells (PBMCs), serum, T cells, B Cells, CD3 cells, CD8 cells, CD4 cells, or other immune cells. Other samples that can be analyzed include urine, feces, saliva, and tissue from a kidney biopsy. Samples not requiring biopsy to obtain, particularly peripheral blood, are preferred. However, a sample may be any material containing tissues, cells, nucleic acids, genes, gene fragments, expression products, polypeptides, exosomes, gene expression products, or gene expression product fragments of a subject to be tested. In some cases, the sample is from a single patient. In some cases, the method comprises analyzing multiple samples at once, e.g., via massively parallel sequencing.

The sample may be obtained by a minimally-invasive method such as a blood draw. The sample may be obtained by venipuncture. In other instances, the sample is obtained by an invasive procedure including but not limited to: biopsy, alveolar or pulmonary lavage, or needle aspiration. The method of biopsy may include surgical biopsy, incisional biopsy, excisional biopsy, punch biopsy, shave biopsy, or skin biopsy. The sample may be formalin fixed sections. The method of needle aspiration may further include fine needle aspiration, core needle biopsy, vacuum assisted biopsy, or large core biopsy. In some embodiments, multiple samples may be obtained by the methods herein to ensure a sufficient amount of biological material. In some instances, the sample is not obtained by biopsy. In some instances, the sample is not a kidney biopsy.

In some cases the methods involve obtaining or analyzing a biopsy sample (e.g., kidney biopsy). In cases where biopsies are obtained, the biopsies may be processed included by placing the samples in a vessel (e.g., tube, vial, microfuge tube, etc.) and storing them at a specific location such as a biorepository. The samples may also be processed by treatment with a specific agent, such as an agent that prevents nucleic acid degradation or deterioration, particularly an agent that protects RNA (e.g., RNALater) or DNA. In some cases, biopsies subjected to histologic analysis including staining (e.g., hematoxylin and eosin (H&E) stain) probing (e.g., a probe attached to a dye, a probe attached to a fluorescent label). In some cases, the staining (e.g., H&E) may be analyzed by a blinded physician such as a blinded pathologist, or at least two blinded pathologists, using criteria such as BANFF criteria. In some cases, a histologic diagnosis is reconciled with laboratory data and clinical courses by one or more clinicians (e.g., at least two clinicians) prior to biomarker analyses.

V. Biomolecule Expression Profiles

The methods, kits, and systems disclosed herein may comprise specifically detecting, profiling, or quantitating biomolecules (e.g., nucleic acids, DNA, RNA, polypeptides, etc.) that are within the biological samples to determine an expression profile. In some instances, genomic expression products, including RNA, or polypeptides, may be isolated from the biological samples. In some cases, nucleic acids, DNA, RNA, polypeptides may be isolated from a cell-free source. In some cases, nucleic acids, DNA, RNA, polypeptides may be isolated from cells derived from the transplant recipient. In some cases, the molecules detected are derived from molecules endogenously present in the sample via an enzymatic process (e.g. cDNA derived from reverse transcription of RNA from the biological sample followed by amplification).

Expression profiles are preferably measured at the nucleic acid level, meaning that levels of mRNA or nucleic acid derived therefrom (e.g., cDNA or cRNA) are measured. An expression profile refers to the expression levels of a plurality of genes in a sample. A nucleic acid derived from mRNA means a nucleic acid synthesized using mRNA as a template. Methods of isolation and amplification of mRNA are described in, e.g. Chapter 3 of Laboratory Techniques in Biochemistry and Molecular Biology: Hybridization With Nucleic Acid Probes, Part I. Theory and Nucleic Acid Preparation, (P. Tijssen, ed.) Elsevier, N.Y. (1993). If mRNA or a nucleic acid therefrom is amplified, the amplification is performed under conditions that approximately preserve the relative proportions of mRNA in the original samples, such that the levels of the amplified nucleic acids can be used to establish phenotypic associations representative of the mRNAs.

In some embodiments, expression levels are determined using a probe array. A number of distinct array formats are available. Some arrays, such as an Affymetrix HG-U133 PM microarray or other Affymetrix GeneChip® array, have different probes occupying discrete known areas of a contiguous support. Exemplary microarrays include but are not limited to the Affymetrix Human Genome U133 Plus 2.0 GeneChip or the HT HG-U133+PM Array Plate.

An array contains one or more probes either perfectly complementary to a particular target mRNA or sufficiently complementarity to the target mRNA to distinguish it from other mRNAs in the sample, and the presence of such a target mRNA can be determined from the hybridization signal of such probes, optionally by comparison with mismatch or other control probes included in the array. Typically, the target bears a fluorescent label, in which case hybridization intensity can be determined by, for example, a scanning confocal microscope in photon counting mode. Appropriate scanning devices are described by e.g., U.S. Pat. Nos. 5,578,832, and 5,631,734. The intensity of labeling of probes hybridizing to a particular mRNA or its amplification product provides a raw measure of expression level.

In other methods, expression levels are determined by so-called "real time amplification" methods also known as quantitative PCR or Taqman. The basis for this method of monitoring the formation of amplification product formed during a PCR reaction with a template using oligonucleotide probes/oligos specific for a region of the template to be detected. In some embodiments, qPCR or Taqman are used immediately following a reverse-transcriptase reaction performed on isolated cellular mRNA; this variety serves to quantitate the levels of individual mRNAs during qPCR.

Taqman uses a dual-labeled fluorogenic oligonucleotide probe. The dual labeled fluorogenic probe used in such assays is typically a short (ca. 20-25 bases) polynucleotide that is labeled with two different fluorescent dyes. The 5' terminus of the probe is typically attached to a reporter dye and the 3' terminus is attached to a quenching dye Regardless of labelling or not, the qPCR probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified. mRNA levels can also be measured without amplification by hybridization to a probe, for example, using a branched nucleic acid probe, such as a QuantiGene® Reagent System from Panomics.

qPCR can also be performed without a dual-labeled fluorogenic probe by using a fluorescent dye (e.g. SYBR Green) specific for dsDNA that reflects the accumulation of dsDNA amplified specific upstream and downstream oligonucleotide primers. The increase in fluorescence during the amplification reaction is followed on a continuous basis and can be used to quantify the amount of mRNA being amplified.

For qPCR or Taqman, the levels of particular genes may be expressed relative to one or more internal control gene measured from the same sample using the same detection methodology. Internal control genes may include so-called "housekeeping" genes (e.g. ACTB, B2M, UBC, GAPD and HPRT1). In some embodiments, the one or more internal control gene is TTC5, C2orf44, or Chr3.

In some embodiments, for qPCR or Taqman detection, a "pre-amplification" step is performed on cDNA transcribed from cellular RNA prior to the quantitatively monitored PCR reaction. This serves to increase signal in conditions where the natural level of the RNA/cDNA to be detected is very low. Suitable methods for pre-amplification include but are not limited LM-PCR, PCR with random oligonucleotide primers (e.g. random hexamer PCR), PCR with poly-A specific primers, and any combination thereof.

In other methods, expression levels are determined by sequencing, such as by RNA sequencing or by DNA sequencing (e.g., of cDNA generated from reverse-transcribing RNA (e.g., mRNA) from a sample). Sequencing may be performed by any available method or technique. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, single molecule nanopore sequencing, sequencing by ligation, sequencing by hybridization, sequencing by nanopore current restriction, Maxim-Gilbert sequencing, primer walking, or a combination thereof. Sequencing by synthesis may comprise reversible terminator sequencing, processive single molecule sequencing, sequential nucleotide flow sequencing, or a combination thereof. Sequential nucleotide flow sequencing may comprise pyrosequencing, pH-mediated sequencing, semiconductor sequencing or a combination thereof. Conducting one or more sequencing reactions may comprise whole genome sequencing or exome sequencing.

Sequencing reactions may comprise one or more capture probes or libraries of capture probes. At least one of the one or more capture probe libraries may comprise one or more capture probes to 1, 2, 3, 4, 5, 6, 7, 8, 9, 10, 11, 12, 13, 14, 15, 20, 30, 40, 50, 60, 70, 80, 90, 100, 110, 120, 130, 140, 150, 160, 170, 180, 190, 200, 210, 220, 230, 240, 250 or more genomic regions. The libraries of capture probes may be at least partially complementary. The libraries of capture probes may be fully complementary. The libraries of capture probes may be at least about 5%, 10%, 15%, 20%, %, 25%, 30%, 35%, 40%, 45%, 50%, 55%, 60%, 70%, 80%, 90%, 95%. 97% or more complementary.

Measuring gene expression levels may comprise reverse transcribing RNA (e.g., mRNA) within a sample in order to produce cDNA. The cDNA may then be measured using any of the methods described herein (e.g., qPCR, microarray, sequencing, etc.).

Alternatively, or additionally, expression levels of genes can be determined at the protein level, meaning that levels of proteins encoded by the genes discussed above are measured. Several methods and devices are well known for determining levels of proteins including immunoassays such as sandwich, competitive, or non-competitive assay formats, to generate a signal that is related to the presence or amount of a protein analyte of interest. Immunoassays such as, but not limited to, lateral flow, enzyme-linked immunoassays (ELISA), radioimmunoassays (RIAs), and competitive binding assays may be utilized. Numerous formats for antibody arrays have been described proposed employing antibodies. Such arrays typically include different antibodies having specificity for different proteins intended to be detected. For example, usually at least one hundred different antibodies are used to detect one hundred different protein targets, each antibody being specific for one target. Other ligands having specificity for a particular protein target can also be used, such as synthetic antibodies. Other compounds with a desired binding specificity can be selected from random libraries of peptides or small molecules. A "protein array", a device that utilizes multiple discrete zones of immobilized antibodies on membranes to detect multiple target antigens in an array, may be utilized. Microtiter plates or automation can be used to facilitate detection of large numbers of different proteins. Protein levels can also be determined by mass spectrometry as described in the examples.

VI. Biomolecule Signatures

The selection of genes or expression products (e.g. mRNA, RNA, DNA, protein) utilized to classify samples from subjects according to the invention into one or more diagnostic categories depends on the particular application (e.g. distinguishing a TX vs non-TX organ, or distinguishing a TX vs a subAR organ). In general, the genes are selected from one of the tables indicated below as appropriate for the application. In some methods, expression levels of at least 2, 3, 4, 5, 10, 20, 25, 50, 100, 110, 120, 130, 140, 150, 160, 170, 180, 190, 200, 210, 220, 230, 240, or 250 (e.g. 100-250) genes shown in Tables 1, 2, 3, 4, 5, 6 and/or 8 are determined. In some methods, expression levels of at most 25, 50, 100, 110, 120, 130, 140, 150, 160, 170, 180, 190, 200, 210, 220, 230, 240, or 250 genes shown in Tables 1, 2, 3, 4, 5, 6 and/or 8 are determined. In some methods, expression levels of about 5, 10, 15, 20, 25, 50, 100, 110, 120, 130, 140, 150, 160, 170, 180, 190, 200, 210, 220, 230, 240, or 250 (e.g. 100-250) genes shown in Tables 1, 2, 3, 4, 5, 6 and/or 8 are determined. The methods may use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, or 210 of the genes or genes contacted by probes provided Table 1. The methods may use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, or all of the genes or genes contacted by probes provided Table 2. The methods may use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, or 120 of the genes or genes contacted by probes provided Table 3. The methods may use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, or all of the genes or genes contacted by probes provided Table 4. The methods may use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55, 60, or all of the genes or genes contacted by probes provided Table 5. The methods may use gene expression products corresponding to at least about 1, 2, 3, 4, 5, 6, 7, 8, 9, 10, 11, 12, 13, 14, 15, 16, 17, 18, 19, 20, 25, 30, 35, 40, or all of the genes or genes contacted by probes provided Table 6. The methods may use gene expression products corresponding to at least about 1, 2, 3, 4, 5, 6, 7, 8, 9, 10, 11, 12, 13, 14, 15, 16, 17, 18, 19, 20, 25, 30, 35, 40, 45, 50, 55 or all of the genes or genes contacted by probes provided Table 8. The methods may use gene expression products corresponding to at most about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, or 210 of the genes or genes contacted by probes provided Table 1. The methods may use gene expression products corresponding to at most about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, or all of the genes or genes contacted by probes provided Table 2. The methods may use gene expression products corresponding to at most about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, or 120 of the genes or genes contacted by probes provided Table 3. The methods may use gene expression products corresponding to at most about 5, 6, 7, 8, 9, 10, 11, 12, 13, 14, 15, 16, 17, 18, 19, 20, 25, 30, 35, 40, 45, 50, 55, 60, 65, or all of the genes or genes contacted by probes provided Table 4. The methods may use gene expression products corresponding to at most about 5, 6, 7, 8, 9, 10, 11, 12, 13, 14, 15, 16, 17, 18, 19, 20, 25, 30, 35, 40, 45, 50, 55, 60, or all of the genes or genes contacted by probes provided Table 5. The methods may use gene expression products corresponding to at most about 5, 6, 7, 8, 9, 10, 11, 12, 13, 14, 15, 16, 17, 18, 19, 20, 25, 30, 35, 40, or all of the genes or genes contacted by probes provided Table 6. The methods may use gene expression products corresponding to at most about 5, 6, 7, 8, 9, 10, 11, 12, 13, 14, 15, 16, 17, 18, 19, 20, 25, 30, 35, 40, 45, 50, 55 or all of the genes or genes contacted by probes provided Table 8.

In some methods, genes are selected such that genes from several different pathways are represented. The genes within a pathway tend to be expressed in a coordinated expression whereas genes from different pathways tend to be expressed more independently. Thus, changes in expression based on the aggregate changes of genes from different pathways can have greater statistical significance than aggregate changes of genes within a pathway. In some cases, expression levels of the top 5, top 10, top 15, top 20, top 25, top 30, top 35, top 40, top 45, top 50, top 55, top 60, top 65, top 70, top 75, top 80, top 85, top 90, top 95, top 100, top 150, or top 200 genes shown in 1, 2, 3, 4, 5, or 7 are determined.

Regardless of the format adopted, the present methods can be practiced by detection of expression levels of a relatively small number of genes or proteins compared with whole genome level expression analysis. In some methods, the total number of genes whose expression levels are determined is less than 5000, 1000, 500, 200, 100, 50, 25, 10, 5 or 3. In some methods, the total number of genes whose expression level is determined is 100-1500, 100-250, 500-1500 or 750-1250. In some methods, the total number of proteins whose expression levels are determined is less than 5000, 1000, 500, 200, 100, 50, 25, 10, 5 or 3. In some methods, the total number of proteins whose expression level is determined is 100-1500, 100-250, 500-1500 or 750-1250. Correspondingly, when an array form is used for detection of expression levels, the array includes probes or probes sets for less than 5000, 1000, 500, 200, 100, 50, 25, 10, 5 or 3 genes. Thus, for example, an Affymetrix GeneChip® expression monitoring array contains a set of about 20-50 oligonucleotide probes (half match and half-mismatch) for monitoring each gene of interest. Such an array design would include less than 5000, 1000, 500, 200, 100, 50, 25, 10, 5 or 3 such probes sets for detecting less than 5000, 1000, 500, 200, 100, 50, 25, 10, 5 or 3 genes. By further example, an alternative array including one cDNA for each gene whose expression level is to be detected would contain less than 5000, 1000, 500, 200, 100, 50, 25, 10, 5 or 3 such cDNAs for analyzing less than 5000, 1000, 500, 200, 100, 50, 25, 10, 5 or 3 genes. By further example, an array containing a different antibody for each protein to be detected would containing less than 5000, 1000, 500, 200, 100, 50, 25, 10, 5 or 3 different antibodies for analyzing less than 5000, 1000, 500, 200, 100, 50, 25, 10, 5 or 3 gene products.

TABLE 1

Example Gene Signatures for TX versus non-TX Detection

| # | Probeset ID | Gene Symbol | Gene Title | Array Name |
|---|---|---|---|---|
| 1 | 1552411_PM_at | DEFB106A/// DEFB106B | defensin, beta 106A/// defensin, beta 106B | HT_HG-U133_Plus_PM |
| 2 | 1554241_PM_at | COCH | cochlin | HT_HG-U133_Plus_PM |
| 3 | 1555057_PM_at | NDUFS4 | NADH dehydrogenase (ubiquinone) Fe—S protein 4, 18 kDa (NADH-coenzyme Q reductase) | HT_HG-U133_Plus_PM |
| 4 | 1555730_PM_a_at | CFL1 | cofilin 1 (non-muscle) | HT_HG-U133_Plus_PM |
| 5 | 1555812_PM_a_at | ARHGDIB | Rho GDP dissociation inhibitor (GDI) beta | HT_HG-U133_Plus_PM |
| 6 | 1555843_PM_at | HNRNPM | heterogeneous nuclear ribonucleoprotein M | HT_HG-U133_Plus_PM |
| 7 | 1555884_PM_at | PSMD6 | proteasome 26S subunit, non-ATPase 6 | HT_HG-U133_Plus_PM |
| 8 | 1555978_PM_s_at | MYL12A | myosin light chain 12A | HT_HG-U133_Plus_PM |
| 9 | 1556015_PM_a_at | MESP2 | mesoderm posterior bHLH transcription factor 2 | HT_HG-U133_Plus_PM |
| 10 | 1556033_PM_at | LINC01138 | long intergenic non-protein coding RNA 1138 | HT_HG-U133_Plus_PM |
| 11 | 1556165_PM_at | LOC100505727 | uncharacterized LOC100505727 | HT_HG-U133_Plus_PM |
| 12 | 1556186_PM_s_at | EMC1 | ER membrane protein complex subunit 1 | HT_HG-U133_Plus_PM |
| 13 | 1556551_PM_s_at | SLC39A6 | solute carrier family 39 (zinc transporter), member 6 | HT_HG-U133_Plus_PM |
| 14 | 1556755_PM_s_at | LOC105375650 | uncharacterized LOC105375650 | HT_HG-U133_Plus_PM |
| 15 | 1556812_PM_a_at | — | gb: AF086041.1/ DB_XREF = gi: 3483386/ TID = Hs2.42975.1/ CNT = 4/FEA = mRNA/ TIER = ConsEnd/STK = 2/ UG = Hs.42975/ UG_TITLE = *Homo sapiens* full length insert cDNA clone YX53E08/ DEF = *Homo sapiens* full length insert cDNA clone YX53E08. | HT_HG-U133_Plus_PM |
| 16 | 1556999_PM_at | LOC100271832 | uncharacterized LOC100271832 | HT_HG-U133_Plus_PM |
| 17 | 1557112_PM_a_at | VPS53 | vacuolar protein sorting 53 homolog (*S. cerevisiae*) | HT_HG-U133_Plus_PM |
| 18 | 1557265_PM_at | — | gb: BE242353/ DB_XREF = gi: 9094081/ DB_XREF = TCAAPIT2047/ CLONE = TCAAP2047/ TID = Hs2.255157.1/ CNT = 9/FEA = mRNA/ TIER = ConsEnd/STK = 1/ UG = Hs.255157/ UG_TITLE = *Homo sapiens* cDNA FLJ31889 fis, clone NT2RP7003091. | HT_HG-U133_Plus_PM |
| 19 | 1557276_PM_at | LINC01016 | long intergenic non-protein coding RNA 1016 | HT_HG-U133_Plus_PM |
| 20 | 1557615_PM_a_at | ARHGAP19-SLIT1 | ARHGAP19-SLIT1 readthrough (NMD candidate) | HT_HG-U133_Plus_PM |
| 21 | 1557744_PM_at | — | gb: AI978831/ DB_XREF = gi: 5803861/ DB_XREF = wr60c07.x1/ CLONE = IMAGE: 2492076/ TID = Hs2.375849.1/ CNT = 3/FEA = mRNA/ TIER = ConsEnd/STK = 1/ UG = Hs.375849/ UG_TITLE = *Homo sapiens* cDNA FLJ25841 fis, clone TST08665. | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| 22 | 1558469_PM_at | LPP | LIM domain containing preferred translocation partner in lipoma | HT_HG-U133_Plus_PM |
| 23 | 1559051_PM_s_at | MB21D1 | Mab-21 domain containing 1 | HT_HG-U133_Plus_PM |
| 24 | 1560263_PM_at | — | gb: BC016780.1/ DB_XREF = gi: 23271116/ TID = Hs2.396207.1/ CNT = 4/FEA = mRNA/ TIER = ConsEnd/STK = 0/ UG = Hs.396207/ UG_TITLE = *Homo sapiens*, clone IMAGE: 4106389, mRNA/ DEF = *Homo sapiens*, clone IMAGE: 4106389, mRNA. | HT_HG-U133_Plus_PM |
| 25 | 1560631_PM_at | CALCOCO2 | calcium binding and coiled-coil domain 2 | HT_HG-U133_Plus_PM |
| 26 | 1560724_PM_at | — | gb: N93148/ DB_XREF = gi: 1265457/ DB_XREF = zb30b02.s1/ CLONE = IMAGE: 305067/ TID = Hs2.189084.1/ CNT = 3/FEA = mRNA/ TIER = ConsEnd/STK = 0/ UG = Hs.189084/ UG_TITLE = *Homo sapiens* cDNA FLJ33564 fis, clone BRAMY2010135. | HT_HG-U133_Plus_PM |
| 27 | 1561236_PM_at | — | gb: BC035177.1/ DB_XREF = gi: 23273365/ TID = Hs2.385559.1/ CNT = 2/FEA = mRNA/ TIER = ConsEnd/STK = 1/ UG = Hs.385559/ UG_TITLE = *Homo sapiens*, clone IMAGE: 5266063, mRNA/ DEF = *Homo sapiens*, clone IMAGE: 5266063, mRNA. | HT_HG-U133_Plus_PM |
| 28 | 1561286_PM_a_at | DIP2A | disco-interacting protein 2 homolog A | HT_HG-U133_Plus_PM |
| 29 | 1562267_PM_s_at | ZNF709 | zinc finger protein 709 | HT_HG-U133_Plus_PM |
| 30 | 1562505_PM_at | — | gb: BC035700.1/ DB_XREF = gi: 23272849/ TID = Hs2.337138.1/ CNT = 2/FEA = mRNA/ TIER = ConsEnd/STK = 0/ UG = Hs.337138/ UG_TITLE = *Homo sapiens*, clone IMAGE: 5550275, mRNA/ DEF = *Homo sapiens*, clone IMAGE: 5550275, mRNA. | HT_HG-U133_Plus_PM |
| 31 | 1563502_PM_at | ZDHHC2 | zinc finger, DHHC-type containing 2 | HT_HG-U133_Plus_PM |
| 32 | 1564362_PM_x_at | ZNF843 | zinc finger protein 843 | HT_HG-U133_Plus_PM |
| 33 | 1566084_PM_at | — | gb: AK090649.1/ DB_XREF = gi: 21748852/ TID = Hs2.33074.1/ CNT = 3/FEA = mRNA/ TIER = ConsEnd/STK = 0/ UG = Hs.33074/ UG_TITLE = *Homo sapiens* cDNA FLJ40968 fis, clone | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| 34 | 1566145_PM_s_at | LOC101928669/// LOC101930100/// LOC644450 | UTERU2012615./ DEF = Homo sapiens cDNA FLJ33330 fis, clone BRACE2000441. uncharacterized LOC101928669/// uncharacterized LOC101930100/// uncharacterized LOC644450 | HT_HG-U133_Plus_PM |
| 35 | 1566671_PM_a_at | LOC105372824/// PDXK | uncharacterized protein C21orf124///pyridoxal (pyridoxine, vitamin B6) kinase | HT_HG-U133_Plus_PM |
| 36 | 1568720_PM_at | ZNF506 | zinc finger protein 506 | HT_HG-U133_Plus_PM |
| 37 | 1569496_PM_s_at | LOC100130872 | uncharacterized LOC100130872 | HT_HG-U133_Plus_PM |
| 38 | 1569521_PM_s_at | ERAP1/// LOC101929747 | endoplasmic reticulum aminopeptidase 1/// uncharacterized LOC101929747 | HT_HG-U133_Plus_PM |
| 39 | 1569527_PM_at | — | gb: BC017275.1/ DB_XREF = gi: 23398506/ TID = Hs2.385730.1/ CNT = 3/FEA = mRNA/ TIER = ConsEnd/STK = 0/ UG = Hs.385730/ UG_TITLE = Homo sapiens, clone IMAGE: 4842907, mRNA/ DEF = Homo sapiens, clone IMAGE: 4842907, mRNA. | HT_HG-U133_Plus_PM |
| 40 | 1569536_PM_at | FLVCR2 | feline leukemia virus subgroup C cellular receptor family, member 2 | HT_HG-U133_Plus_PM |
| 41 | 1570388_PM_a_at | LOC101929800/// LOC440896 | uncharacterized LOC101929800/// uncharacterized LOC440896 | HT_HG-U133_Plus_PM |
| 42 | 200041_PM_s_at | ATP6V1G2-DDX39B/// DDX39B | ATP6V1G2-DDX39B readthrough (NMD candidate)///DEAD (Asp-Glu-Ala-Asp) box polypeptide 39B | HT_HG-U133_Plus_PM |
| 43 | 200805_PM_at | LMAN2 | lectin, mannose-binding 2 | HT_HG-U133_Plus_PM |
| 44 | 200928_PM_s_at | RAB14 | RAB14, member RAS oncogene family | HT_HG-U133_Plus_PM |
| 45 | 201127_PM_s_at | ACLY | ATP citrate lyase | HT_HG-U133_Plus_PM |
| 46 | 201222_PM_s_at | RAD23B | RAD23 homolog B, nucleotide excision repair protein | HT_HG-U133_Plus_PM |
| 47 | 201251_PM_at | PKM | pyruvate kinase, muscle | HT_HG-U133_Plus_PM |
| 48 | 201739_PM_at | SGK1 | serum/glucocorticoid regulated kinase 1 | HT_HG-U133_Plus_PM |
| 49 | 202015_PM_x_at | — | gb: NM_006838.1/ DB_XREF = gi: 5803091/ GEN = MNPEP/ FEA = FLmRNA/ CNT = 160/ TID = Hs.78935.0/ TIER = FL/STK = 0/ UG = Hs.78935/ LL = 10988/DEF = Homo sapiens methionine aminopeptidase; eIF-2-associated p67 (MNPEP), mRNA./ | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| | | | PROD = methionine aminopeptidase; eIF-2-associated p67/ FL = gb: NM_006838.1 gb: U29607.1 | |
| 50 | 202953_PM_at | C1QB | complement component 1, q subcomponent, B chain | HT_HG-U133_Plus_PM |
| 51 | 203744_PM_at | HMGB3 | high mobility group box 3 | HT_HG-U133_Plus_PM |
| 52 | 203768_PM_s_at | STS | steroid sulfatase (microsomal), isozyme S | HT_HG-U133_Plus_PM |
| 53 | 204218_PM_at | ANAPC15 | anaphase promoting complex subunit 15 | HT_HG-U133_Plus_PM |
| 54 | 204701_PM_s_at | STOML1 | stomatin (EPB72)-like 1 | HT_HG-U133_Plus_PM |
| 55 | 204787_PM_at | VSIG4 | V-set and immunoglobulin domain containing 4 | HT_HG-U133_Plus_PM |
| 56 | 205743_PM_at | STAC | SH3 and cysteine rich domain | HT_HG-U133_Plus_PM |
| 57 | 205905_PM_s_at | MICA/// MICB | MHC class I polypeptide-related sequence A/// MHC class I polypeptide-related sequence B | HT_HG-U133_Plus_PM |
| 58 | 206123_PM_at | LLGL1 | lethal giant larvae homolog 1 (*Drosophila*) | HT_HG-U133_Plus_PM |
| 59 | 206663_PM_at | SP4 | Sp4 transcription factor | HT_HG-U133_Plus_PM |
| 60 | 206759_PM_at | FCER2 | Fc fragment of IgE, low affinity II, receptor for (CD23) | HT_HG-U133_Plus_PM |
| 61 | 207346_PM_at | STX2 | syntaxin 2 | HT_HG-U133_Plus_PM |
| 62 | 207688_PM_s_at | — | gb: NM_005538.1/ DB_XREF = gi: 5031794/ GEN = INHBC/ FEA = FLmRNA/CNT = 3/ TID = Hs.199538.0/ TIER = FL/STK = 0/ UG = Hs.199538/ LL = 3626/DEF = *Homo sapiens* inhibin, beta C (INHBC), mRNA./ PROD = inhibin beta C subunit precursor/ FL = gb: NM_005538.1 | HT_HG-U133_Plus_PM |
| 63 | 208725_PM_at | EIF2S2 | eukaryotic translation initiation factor 2, subunit 2 beta, 38 kDa | HT_HG-U133_Plus_PM |
| 64 | 208730_PM_x_at | RAB2A | RAB2A, member RAS oncogene family | HT_HG-U133_Plus_PM |
| 65 | 208963_PM_x_at | FADS1 | fatty acid desaturase 1 | HT_HG-U133_Plus_PM |
| 66 | 208997_PM_s_at | UCP2 | uncoupling protein 2 (mitochondrial, proton carrier) | HT_HG-U133_Plus_PM |
| 67 | 209321_PM_s_at | ADCY3 | adenylate cyclase 3 | HT_HG-U133_Plus_PM |
| 68 | 209331_PM_s_at | MAX | MYC associated factor X | HT_HG-U133_Plus_PM |
| 69 | 209410_PM_s_at | GRB10 | growth factor receptor bound protein 10 | HT_HG-U133_Plus_PM |
| 70 | 209415_PM_at | FZR1 | fizzy/cell division cycle 20 related 1 | HT_HG-U133_Plus_PM |
| 71 | 209568_PM_s_at | RGL1 | ral guanine nucleotide dissociation stimulator-like 1 | HT_HG-U133_Plus_PM |
| 72 | 209586_PM_s_at | PRUNE | prune exopolyphosphatase | HT_HG-U133_Plus_PM |
| 73 | 209913_PM_x_at | AP5Z1 | adaptor-related protein complex 5, zeta 1 subunit | HT_HG-U133_Plus_PM |
| 74 | 209935_PM_at | ATP2C1 | ATPase, Ca++ transporting, type 2C, member 1 | HT_HG-U133_Plus_PM |
| 75 | 210219_PM_at | SP100 | SP100 nuclear antigen | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| 76 | 210253_PM_at | HTATIP2 | HIV-1 Tat interactive protein 2 | HT_HG-U133_Plus_PM |
| 77 | 210743_PM_s_at | CDC14A | cell division cycle 14A | HT_HG-U133_Plus_PM |
| 78 | 211022_PM_s_at | ATRX | alpha thalassemia/mental retardation syndrome X-linked | HT_HG-U133_Plus_PM |
| 79 | 211435_PM_at | — | gb: AF202635.1/ DB_XREF = gi: 10732645/ FEA = FLmRNA/CNT = 1/ TID = Hs.302135.0/ TIER = FL/STK = 0/ UG = Hs.302135/ DEF = *Homo sapiens* PP1200 mRNA, complete cds./PROD = PP1200/ FL = gb: AF202635.1 | HT_HG-U133_Plus_PM |
| 80 | 211578_PM_s_at | RPS6KB1 | ribosomal protein S6 kinase, 70 kDa, polypeptide 1 | HT_HG-U133_Plus_PM |
| 81 | 211598_PM_x_at | VIPR2 | vasoactive intestinal peptide receptor 2 | HT_HG-U133_Plus_PM |
| 82 | 211977_PM_at | GPR107 | G protein-coupled receptor 107 | HT_HG-U133_Plus_PM |
| 83 | 212611_PM_at | DTX4 | deltex 4, E3 ubiquitin ligase | HT_HG-U133_Plus_PM |
| 84 | 213008_PM_at | FANCI | Fanconi anemia complementation group I | HT_HG-U133_Plus_PM |
| 85 | 213076_PM_at | ITPKC | inositol-trisphosphate 3-kinase C | HT_HG-U133_Plus_PM |
| 86 | 214195_PM_at | TPP1 | tripeptidyl peptidase I | HT_HG-U133_Plus_PM |
| 87 | 214289_PM_at | PSMB1 | proteasome subunit beta 1 | HT_HG-U133_Plus_PM |
| 88 | 214442_PM_s_at | PIAS2 | protein inhibitor of activated STAT 2 | HT_HG-U133_Plus_PM |
| 89 | 214510_PM_at | GPR20 | G protein-coupled receptor 20 | HT_HG-U133_Plus_PM |
| 90 | 214572_PM_s_at | INSL3 | insulin-like 3 (Leydig cell) | HT_HG-U133_Plus_PM |
| 91 | 214907_PM_at | CEACAM21 | carcinoembryonic antigen-related cell adhesion molecule 21 | HT_HG-U133_Plus_PM |
| 92 | 214947_PM_at | FAM105A | family with sequence similarity 105, member A | HT_HG-U133_Plus_PM |
| 93 | 215233_PM_at | JMJD6 | jumonji domain containing 6 | HT_HG-U133_Plus_PM |
| 94 | 215641_PM_at | SEC24D | SEC24 homolog D, COPII coat complex component | HT_HG-U133_Plus_PM |
| 95 | 215898_PM_at | TTLL5 | tubulin tyrosine ligase-like family member 5 | HT_HG-U133_Plus_PM |
| 96 | 216069_PM_at | PRMT2 | protein arginine methyltransferase 2 | HT_HG-U133_Plus_PM |
| 97 | 216517_PM_at | IGKC/// IGKV1-8/// IGKV1-9/// IGKV1D-8 | immunoglobulin kappa constant/// immunoglobulin kappa variable 1-8/// immunoglobulin kappa variable 1-9/// immunoglobulin kappa variable 1D-8 | HT_HG-U133_Plus_PM |
| 98 | 216951_PM_at | FCGR1A | Fc fragment of IgG, high affinity Ia, receptor (CD64) | HT_HG-U133_Plus_PM |
| 99 | 217137_PM_x_at | — | gb: K00627.1 DB_XREF = gi: 337653/ FEA = mRNA/CNT = 1/ TID = Hs.203776.0/ TIER = ConsEnd/STK = 0/ UG = Hs.203776/ | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| | | | UG_TITLE = Human kpni repeat mrna (cdna clone pcd-kpni-8), 3 end/ DEF = human kpni repeat mrna (cdna clone pcd-kpni-8), 3 end. | |
| 100 | 217208_PM_s_at | DLG1 | discs, large homolog 1 (*Drosophila*) | HT_HG-U133_Plus_PM |
| 101 | 217436_PM_x_at | HLA-J | major histocompatibility complex, class I, J (pseudogene) | HT_HG-U133_Plus_PM |
| 102 | 217622_PM_at | RHBDD3 | rhomboid domain containing 3 | HT_HG-U133_Plus_PM |
| 103 | 217671_PM_at | — | gb: BE466926/ DB_XREF = gi: 9512701/ DB_XREF = hz59a04.x1/ CLONE = IMAGE: 3212238/ FEA = EST/CNT = 3/ TID = Hs.279706.0/ TIER = ConsEnd/STK = 3/ UG = Hs.279706/ UG_TITLE = ESTs | HT_HG-U133_Plus_PM |
| 104 | 218332_PM_at | BEX1 | brain expressed X-linked 1 | HT_HG-U133_Plus_PM |
| 105 | 219471_PM_at | KIAA0226L | KIAA0226-like | HT_HG-U133_Plus_PM |
| 106 | 219497_PM_s_at | BCL11A | B-cell CLL/lymphoma 11A (zinc finger protein) | HT_HG-U133_Plus_PM |
| 107 | 219925_PM_at | ZMYM6 | zinc finger, MYM-type 6 | HT_HG-U133_Plus_PM |
| 108 | 219966_PM_x_at | BANP | BTG3 associated nuclear protein | HT_HG-U133_Plus_PM |
| 109 | 219980_PM_at | ABHD18 | abhydrolase domain containing 18 | HT_HG-U133_Plus_PM |
| 110 | 220315_PM_at | PARP11 | poly(ADP-ribose) polymerase family member 11 | HT_HG-U133_Plus_PM |
| 111 | 220396_PM_at | LOC105369820 | uncharacterized LOC105369820 | HT_HG-U133_Plus_PM |
| 112 | 220575_PM_at | FAM106A | family with sequence similarity 106, member A | HT_HG-U133_Plus_PM |
| 113 | 220702_PM_at | TLK1 | tousled-like kinase 1 | HT_HG-U133_Plus_PM |
| 114 | 221041_PM_s_at | SLC17A5 | solute carrier family 17 (acidic sugar transporter), member 5 | HT_HG-U133_Plus_PM |
| 115 | 221959_PM_at | FAM110B | family with sequence similarity 110, member B | HT_HG-U133_Plus_PM |
| 116 | 221992_PM_at | NPIP///NPIPA1///NPIPB15///NPIPB6///NPIPB8///NPIPB9///PDXDC2P | nuclear pore complex interacting protein family, member A1 pseudogene///nuclear pore complex interacting protein family, member A1///nuclear pore complex interacting protein family, member B15///nuclear pore complex interacting protein family, member B6///nuclear pore complex interacting protein family, member B8///nuclear pore complex interacting protein family, member B9///pyridoxal-dependent decarboxylase domain containing 2, pseudogene | HT_HG-U133_Plus_PM |
| 117 | 222364_PM_at | SLC44A1 | solute carrier family 44 (choline transporter), member 1 | HT_HG-U133_Plus_PM |
| 118 | 222419_PM_x_at | UBE2H | ubiquitin conjugating enzyme E2H | HT_HG-U133_Plus_PM |
| 119 | 222615_PM_s_at | LOC100630923///PRKRIP1 | LOC100289561-PRKRIP1 readthrough/// | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| | | | PRKR interacting protein 1 (IL11 inducible) | |
| 120 | 222799_PM_at | WDR91 | WD repeat domain 91 | HT_HG-U133_Plus_PM |
| 121 | 222889_PM_at | DCLRE1B | DNA cross-link repair 1B | HT_HG-U133_Plus_PM |
| 122 | 223080_PM_at | GLS | glutaminase | HT_HG-U133_Plus_PM |
| 123 | 223323_PM_x_at | TRPM7 | transient receptor potential cation channel, subfamily M, member 7 | HT_HG-U133_Plus_PM |
| 124 | 223621_PM_at | PNMA3 | paraneoplastic Ma antigen 3 | HT_HG-U133_Plus_PM |
| 125 | 224516_PM_s_at | CXXC5 | CXXC finger protein 5 | HT_HG-U133_Plus_PM |
| 126 | 224549_PM_x_at | — | gb: AF194537.1/ DB_XREF = gi: 11037116/ GEN = NAG13/ FEA = FLmRNA/CNT = 1/ TID = HsAffx.900497.1131/ TIER = FL/STK = 0/ DEF = Homo sapiens NAG13 (NAG13) mRNA, complete cds./ PROD = NAG13/ FL = gb: AF194537.1 | HT_HG-U133_Plus_PM |
| 127 | 224559_PM_at | MALAT1 | metastasis associated lung adenocarcinoma transcript 1 (non-protein coding) | HT_HG-U133_Plus_PM |
| 128 | 224840_PM_at | FKBP5 | FK506 binding protein 5 | HT_HG-U133_Plus_PM |
| 129 | 224954_PM_at | SHMT1 | serine hydroxymethyltransferase 1 (soluble) | HT_HG-U133_Plus_PM |
| 130 | 225232_PM_at | MTMR12 | myotubularin related protein 12 | HT_HG-U133_Plus_PM |
| 131 | 225759_PM_x_at | CLMN | calmin (calponin-like, transmembrane) | HT_HG-U133_Plus_PM |
| 132 | 225959_PM_s_at | ZNRF1 | zinc and ring finger 1, E3 ubiquitin protein ligase | HT_HG-U133_Plus_PM |
| 133 | 226137_PM_at | ZFHX3 | zinc finger homeobox 3 | HT_HG-U133_Plus_PM |
| 134 | 226450_PM_at | INSR | insulin receptor | HT_HG-U133_Plus_PM |
| 135 | 226456_PM_at | RMI2 | RecQ mediated genome instability 2 | HT_HG-U133_Plus_PM |
| 136 | 226540_PM_at | CFAP73 | cilia and flagella associated protein 73 | HT_HG-U133_Plus_PM |
| 137 | 226599_PM_at | FHDC1 | FH2 domain containing 1 | HT_HG-U133_Plus_PM |
| 138 | 226699_PM_at | FCHSD1 | FCH and double SH3 domains 1 | HT_HG-U133_Plus_PM |
| 139 | 226856_PM_at | MUSTN1 | musculoskeletal, embryonic nuclear protein 1 | HT_HG-U133_Plus_PM |
| 140 | 227052_PM_at | SMIM14 | small integral membrane protein 14 | HT_HG-U133_Plus_PM |
| 141 | 227053_PM_at | PACSIN1 | protein kinase C and casein kinase substrate in neurons 1 | HT_HG-U133_Plus_PM |
| 142 | 227106_PM_at | TMEM198B | transmembrane protein 198B, pseudogene | HT_HG-U133_Plus_PM |
| 143 | 227333_PM_at | DCUN1D3 | DCN1, defective in cullin neddylation 1, domain containing 3 | HT_HG-U133_Plus_PM |
| 144 | 227410_PM_at | FAM43A | family with sequence similarity 43, member A | HT_HG-U133_Plus_PM |
| 145 | 227709_PM_at | TPT1-AS1 | TPT1 antisense RNA 1 | HT_HG-U133_Plus_PM |
| 146 | 227710_PM_s_at | TPT1-AS1 | TPT1 antisense RNA 1 | HT_HG-U133_Plus_PM |
| 147 | 227743_PM_at | MYO15B | myosin XVB | HT_HG-U133_Plus_PM |
| 148 | 227912_PM_s_at | EXOSC3 | exosome component 3 | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| 149 | 228209_PM_at | ACBD6///LHX4-AS1 | acyl-CoA binding domain containing 6///LHX4 antisense RNA 1 | HT_HG-U133_Plus_PM |
| 150 | 228610_PM_at | TM9SF3 | transmembrane 9 superfamily member 3 | HT_HG-U133_Plus_PM |
| 151 | 228786_PM_at | SVIL-AS1 | SVIL antisense RNA 1 | HT_HG-U133_Plus_PM |
| 152 | 228928_PM_x_at | BANP | BTG3 associated nuclear protein | HT_HG-U133_Plus_PM |
| 153 | 229525_PM_at | — | gb: AW118132/ DB_XREF = gi: 6086716/ DB_XREF = xe03f10.x1/ CLONE = IMAGE: 2606059/ FEA = EST/CNT = 20/ TID = Hs.288151.1/ TIER = Stack/STK = 12/ UG = Hs.288151/ LL = 80145/ UG_GENE-FLJ23445/ UG_TITLE = hypothetical protein FLJ23445 | HT_HG-U133_Plus_PM |
| 154 | 229972_PM_at | LOC101926963 | uncharacterized LOC101926963 | HT_HG-U133_Plus_PM |
| 155 | 230057_PM_at | LOC285178 | uncharacterized LOC285178 | HT_HG-U133_Plus_PM |
| 156 | 230202_PM_at | — | gb: AI703057/ DB_XREF = gi: 4990957/ DB_XREF = wd81c08.x1/ CLONE = IMAGE: 2337998/ FEA = EST/CNT = 25/ TID = Hs.75569.2/ TIER = Stack/STK = 10/ UG = Hs.75569/LL = 5970/ UG_GENE-RELA/ UG_TITLE = v-rel avian/ reticuloendotheliosis viral oncogene homolog A (nuclear factor of kappa light polypeptide gene enhancer in B-cells 3 (p65)) | HT_HG-U133_Plus_PM |
| 157 | 230699_PM_at | PGLS | 6-phosphogluconolactonase | HT_HG-U133_Plus_PM |
| 158 | 230877_PM_at | IGHD | immunoglobulin heavy constant delta | HT_HG-U133_Plus_PM |
| 159 | 231252_PM_at | KANSL1L | KAT8 regulatory NSL complex subunit 1 like | HT_HG-U133_Plus_PM |
| 160 | 231437_PM_at | SLC35D2 | solute carrier family 35 (UDP-GlcNAc/UDP-glucose transporter), member D2 | HT_HG-U133_Plus_PM |
| 161 | 231854_PM_at | PIK3CA | phosphatidylinositol-4,5-bisphosphate 3-kinase, catalytic subunit alpha | HT_HG-U133_Plus_PM |
| 162 | 231937_PM_at | — | gb: AU153281/ DB_XREF = gi: 11014802/ DB_XREF = AU153281/ CLONE = NT2RP3002799/ FEA = mRNA/CNT = 20/ TID = Hs.185707.0/ TIER = ConsEnd/STK = 4/ UG = Hs.185707/ UG_TITLE = *Homo sapiens* cDNA FLJ14200 fis, clone NT2RP3002799 | HT_HG-U133_Plus_PM |
| 163 | 232107_PM_at | SDHC | succinate dehydrogenase complex, subunit C, integral membrane protein, 15 kDa | HT_HG-U133_Plus_PM |
| 164 | 232375_PM_at | — | gb: AI539443/ DB_XREF = gi: 4453578/ DB_XREF = te51e11.x1/ CLONE = IMAGE: 2090252/ FEA = mRNA/CNT = 10 TID = Hs.137447.0/ | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| 165 | 232622_PM_at | — | TIER = ConsEnd/STK = 3/ UG = Hs.137447/ UG_TITLE = *Homo sapiens* cDNA FLJ12169 fis, clone MAMMA1000643 gb: AK023865.1/ DB_XREF = gi: 10435932/ FEA = mRNA/CNT = 6/ TID = Hs.186104.0/ TIER = ConsEnd/STK = 0/ UG = Hs.186104/ UG_TITLE = *Homo sapiens* cDNA FLJ13803 fis, clone THYRO1000187/ DEF = *Homo sapiens* cDNA FLJ13803 fis, clone THYRO1000187. | HT_HG-U133_Plus_PM |
| 166 | 232864_PM_s_at | AFF4 | AF4/FMR2 family, member 4 | HT_HG-U133_Plus_PM |
| 167 | 232975_PM_at | HCG18 | HLA complex group 18 (non-protein coding) | HT_HG-U133_Plus_PM |
| 168 | 233430_PM_at | TBC1D22B | TBC1 domain family, member 22B | HT_HG-U133_Plus_PM |
| 169 | 233678_PM_at | — | gb: AL442094.1/ DB_XREF = gi: 10241769/ FEA = mRNA/CNT = 2/ TID = Hs.306925.0/ TIER = ConsEnd/STK = 0/ UG = Hs.306925/ UG_TITLE = *Homo sapiens* mRNA; cDNA DKFZp547E024 (from clone DKFZp547E024)/ DEF = *Homo sapiens* mRNA; cDNA DKFZp547E024 (from clone DKFZp547E024). | HT_HG-U133_Plus_PM |
| 170 | 233762_PM_at | — | gb: AU158436/ DB_XREF = gi: 11019957/ DB_XREF = AU158436/ CLONE = PLACE2000379/ FEA = mRNA/CNT = 2/ TID = Hs.296742.0/ TIER = ConsEnd/STK = 1/ UG = Hs.296742/ UG_TITLE = *Homo sapiens* cDNA FLJ13711 fis, clone PLACE2000379 | HT_HG-U133_Plus_PM |
| 171 | 233779_PM_x_at | — | gb: AK022046.1/ DB_XREF = gi: 10433365/ FEA = mRNA/CNT = 3/ TID = Hs.293922.0/ TIER = ConsEnd/STK = 0/ UG = Hs.293922/ UG_TITLE = *Homo sapiens* cDNA FLJ11984 fis, clone HEMBB1001348/ DEF = *Homo sapiens* CDNA FLJ11984 fis, clone HEMBB1001348. | HT_HG-U133_Plus_PM |
| 172 | 234041_PM_at | — | gb: AK026269.1/ DB_XREF = gi: 10439072/ FEA = mRNA/CNT = 2/ TID = Hs.287704.0/ TIER = ConsEnd/STK = 0/ UG = Hs.287704/ UG_TITLE = *Homo sapiens* cDNA: FLJ22616 fis, clone HSI05164/ DEF = *Homo sapiens* cDNA: FLJ22616 fis, clone HSI05164. | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| 173 | 235461_PM_at | TET2 | tet methylcytosine dioxygenase 2 | HT_HG-U133_Plus_PM |
| 174 | 235596_PM_at | — | gb: BE562520/ DB_XREF = gi: 9806240/ DB_XREF = 601335817F1/ CLONE-IMAGE: 3689740/ FEA = EST/CNT = 12/ TID = Hs.125720.0/ TIER = ConsEnd/STK = 0/ UG = Hs.125720/ UG_TITLE = ESTs | HT_HG-U133_Plus_PM |
| 175 | 235823_PM_at | ACSF3 | acyl-CoA synthetase family member 3 | HT_HG-U133_Plus_PM |
| 176 | 236072_PM_at | — | gb: N64578/ DB_XREF = gi: 1212407/ DB_XREF = yz51d10.s1/ CLONE = IMAGE: 286579/ FEA = EST/CNT = 7/ TID = Hs.49014.0/ TIER = ConsEnd/STK = 5/ UG = Hs.49014/ UG_TITLE = ESTs, Weakly similar to AF116721 112 PRO2738 (*H. sapiens*) | HT_HG-U133_Plus_PM |
| 177 | 236706_PM_at | LYG1 | lysozyme G-like 1 | HT_HG-U133_Plus_PM |
| 178 | 236962_PM_at | — | gb: AA521018/ DB_XREF = gi: 2261561/ DB_XREF = aa70f07.s1/ CLONE = IMAGE: 826309/ FEA = EST/CNT = 7/ TID = Hs.104419.0/ TIER = ConsEnd/STK = 5/ UG = Hs.104419/ UG_TITLE = ESTs | HT_HG-U133_Plus_PM |
| 179 | 237072_PM_at | — | gb: BF223935/ DB_XREF = gi: 11131129/ DB_XREF = 7q82b06.x1/ CLONE = IMAGE: 3704771/ FEA = EST/CNT = 5/ TID = Hs.192125.0/ TIER = ConsEnd/STK = 5/ UG = Hs.192125/ UG_TITLE = ESTs | HT_HG-U133_Plus_PM |
| 180 | 237689_PM_at | — | gb: BF111108/ DB_XREF = gi: 10940798/ DB_XREF = 7n43f06.x1/ CLONE = IMAGE: 3567491/ FEA = EST/CNT = 7/ TID = Hs.144063.0/ TIER = ConsEnd/STK = 7/ UG = Hs.144063/ UG_TITLE = ESTs, Moderately similar to SYS_HUMAN SERYL-TRNA SYNTHETASE (*H. sapiens*) | HT_HG-U133_Plus_PM |
| 181 | 238349_PM_at | UBN2 | ubinuclein 2 | HT_HG-U133_Plus_PM |
| 182 | 238545_PM_at | BRD7 | bromodomain containing 7 | HT_HG-U133_Plus_PM |
| 183 | 238797_PM_at | TRIM11 | tripartite motif containing 11 | HT_HG-U133_Plus_PM |
| 184 | 239063_PM_at | LOC105371932 | uncharacterized LOC105371932 | HT_HG-U133_Plus_PM |
| 185 | 239114_PM_at | — | gb: BE048824/ DB_XREF = gi: 8365868/ DB_XREF = hr54b02.x1/ CLONE = IMAGE: 3132267/ FEA = EST/CNT = 5/ TID = Hs.188966.0/ TIER = ConsEnd/STK = 4/ UG = Hs.188966/ UG_TITLE = ESTs | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| 186 | 239557_PM_at | — | gb: AW474960/<br>DB_XREF = gi: 7045066/<br>DB_XREF = hb01e08.x1/<br>CLONE = IMAGE: 2881958/<br>FEA = EST/CNT = 5/<br>TID = Hs.182258.0/<br>TIER = ConsEnd/STK = 4/<br>UG = Hs.182258/<br>UG_TITLE = ESTs | HT_HG-U133_Plus_PM |
| 187 | 239772_PM_x_at | DHX30 | DEAH (Asp-Glu-Ala-His) box helicase 30 | HT_HG-U133_Plus_PM |
| 188 | 239957_PM_at | — | gb: AW510793/<br>DB_XREF = gi: 7148871/<br>DB_XREF = hd39h04.x1/<br>CLONE = IMAGE: 2911927/<br>FEA = EST/CNT = 5/<br>TID = Hs.240728.0/<br>TIER = ConsEnd/STK = 4/<br>UG = Hs.240728/<br>UG_TITLE = ESTs | HT_HG-U133_Plus_PM |
| 189 | 240008_PM_at | — | gb: AI955765/<br>DB_XREF = gi: 5748075/<br>DB_XREF = wt59c08.x1/<br>CLONE = IMAGE: 2511758/<br>FEA = EST/CNT = 7/<br>TID = Hs.146907.0/<br>TIER = ConsEnd/STK = 1/<br>UG = Hs.146907/<br>UG_TITLE = ESTs | HT_HG-U133_Plus_PM |
| 190 | 240220_PM_at | — | gb: AI435046/<br>DB_XREF = gi: 4300436/<br>DB_XREF = th82b12.x1/<br>CLONE = IMAGE: 2125151/<br>FEA = EST/CNT = 7/<br>TID = Hs.164318.0/<br>TIER = ConsEnd/STK = 0/<br>UG = Hs.164318/<br>UG_TITLE = ESTs | HT_HG-U133_Plus_PM |
| 191 | 240410_PM_at | — | gb: AI928355/<br>DB_XREF = gi: 5664319/<br>DB_XREF = wo96c10.x1/<br>CLONE-IMAGE: 2463186/<br>FEA = EST/CNT = 4/<br>TID = Hs.185805.0/<br>TIER = ConsEnd/STK = 4/<br>UG = Hs.185805/<br>UG_TITLE = ESTs | HT_HG-U133_Plus_PM |
| 192 | 241458_PM_at | — | gb: AI868267/<br>DB_XREF = gi: 5541283/<br>DB_XREF-tj42h12.x1/<br>CLONE = IMAGE: 2144231/<br>FEA = EST/CNT = 11/<br>TID = Hs.295848.0/<br>TIER = ConsEnd/STK = 3/<br>UG = Hs.295848/<br>UG_TITLE = ESTs | HT_HG-U133_Plus_PM |
| 193 | 241667_PM_x_at | — | gb: AI820891/<br>DB_XREF = gi: 5439970/<br>DB_XREF = qv30e01.x5/<br>CLONE = IMAGE: 1983096/<br>FEA = EST/CNT = 8/<br>TID = Hs.145356.0/<br>TIER = ConsEnd/STK = 0/<br>UG = Hs.145356/<br>UG_TITLE = ESTs | HT_HG-U133_Plus_PM |
| 194 | 242014_PM_at | — | gb: AI825538/<br>DB_XREF = gi: 5446209/<br>DB_XREF = wb18h06.x1/<br>CLONE = IMAGE: 2306075/<br>FEA = EST/CNT = 3/<br>TID = Hs.187534.0/<br>TIER = ConsEnd/STK = 3/<br>UG = Hs.187534/<br>UG_TITLE = ESTs | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| 195 | 242176_PM_at | MEF2A | myocyte enhancer factor 2A | HT_HG-U133_Plus_PM |
| 196 | 242413_PM_at | — | gb: AI814925/ DB_XREF = gi: 5426140/ DB_XREF = wk68f11.x1/ CLONE = IMAGE: 2420589/ FEA = EST/CNT = 4/ TID = Hs.272102.0/ TIER = ConsEnd/STK = 3/ UG = Hs.272102/ UG_TITLE = ESTs | HT_HG-U133_Plus_PM |
| 197 | 242479_PM_s_at | MCM4 | minichromosome maintenance complex component 4 | HT_HG-U133_Plus_PM |
| 198 | 242874_PM_at | — | gb: AI741506/ DB_XREF = gi: 5109794/ DB_XREF = wg21a12.x1/ CLONE = IMAGE: 2365726/ FEA = EST/CNT = 3/ TID = Hs.186753.0/ TIER = ConsEnd/STK = 3/ UG = Hs.186753/ UG_TITLE = ESTs, Weakly similar to ALU1_HUMAN ALU SUBFAMILY J SEQUENCE CONTAMINATION WARNING ENTRY (*H. sapiens*) | HT_HG-U133_Plus_PM |
| 199 | 242918_PM_at | NASP | nuclear autoantigenic sperm protein (histone-binding) | HT_HG-U133_Plus_PM |
| 200 | 243470_PM_at | — | gb: AW206536/ DB_XREF = gi: 6506032/ DB_XREF = UI-H-BI1-aez-g-02-0-UI.s1/ CLONE = IMAGE: 2721195/ FEA = EST/CNT = 3/ TID = Hs.196461.0/ TIER = ConsEnd/STK = 3/ UG = Hs.196461/ UG_TITLE = ESTs | HT_HG-U133_Plus_PM |
| 201 | 243476_PM_at | LOC105371724/// NF1 | uncharacterized LOC105371724/// neurofibromin 1 | HT_HG-U133_Plus_PM |
| 202 | 243858_PM_at | — | gb: AA699970/ DB_XREF = gi: 2702933/ DB_XREF = zi65g08.s1/ CLONE = IMAGE: 435710/ FEA = EST/CNT = 3/ TID = Hs.186498.0/ TIER = ConsEnd/STK = 3/ UG = Hs.186498/ UG_TITLE = ESTs | HT_HG-U133_Plus_PM |
| 203 | 244047_PM_at | — | gb: AA447714/ DB_XREF = gi: 2161384/ DB_XREF = aa20c03.s1/ CLONE = IMAGE: 813796/ FEA = EST/CNT = 5/ TID = Hs.152188.0/ TIER = ConsEnd/STK = 1/ UG = Hs.152188/ UG_TITLE = ESTs | HT_HG-U133_Plus_PM |
| 204 | 244233_PM_at | TPGS2 | tubulin polyglutamylase complex subunit 2 | HT_HG-U133_Plus_PM |
| 205 | 244702_PM_at | — | gb: AI654208 DB_XREF = gi: 4738187/ DB_XREF = wb24f02.x1/ CLONE = IMAGE: 2306619/ FEA = EST/CNT = 3 TID = Hs.195381.0/ TIER = ConsEnd/STK = 3/ UG = Hs.195381/ UG_TITLE = ESTs | HT_HG-U133_Plus_PM |

TABLE 1-continued

Example Gene Signatures for TX versus non-TX Detection

| # | Probeset ID | Gene Symbol | Gene Title | Array Name |
|---|---|---|---|---|
| 206 | 244746_PM_at | SEMA6D | sema domain, transmembrane domain (TM), and cytoplasmic domain, (semaphorin) 6D | HT_HG-U133_Plus_PM |
| 207 | 35776_PM_at | ITSN1 | intersectin 1 | HT_HG-U133_Plus_PM |
| 208 | 44790_PM_s_at | KIAA0226L | KIAA0226-like | HT_HG-U133_Plus_PM |
| 209 | 49327_PM_at | SIRT3 | sirtuin 3 | HT_HG-U133_Plus_PM |
| 210 | 50314_PM_i_at | C20orf27 | chromosome 20 open reading frame 27 | HT_HG-U133_Plus_PM |

TABLE 2

Example Alternate Genes for use in TX versus non-TX Detection

| # | Probeset ID | Gene Symbol | Gene Title | Array Name |
|---|---|---|---|---|
| 1 | 1552411_PM_at | DEFB106A///DEFB106B | defensin, beta 106A///defensin, beta 106B | HT_HG-U133_Plus_PM |
| 2 | 1554241_PM_at | COCH | cochlin | HT_HG-U133_Plus_PM |
| 3 | 1555730_PM_a_at | CFL1 | cofilin 1 (non-muscle) | HT_HG-U133_Plus_PM |
| 4 | 1555843_PM_at | HNRNPM | heterogeneous nuclear ribonucleoprotein M | HT_HG-U133_Plus_PM |
| 5 | 1556015_PM_a_at | MESP2 | mesoderm posterior bHLH transcription factor 2 | HT_HG-U133_Plus_PM |
| 6 | 1556165_PM_at | LOC100505727 | uncharacterized LOC100505727 | HT_HG-U133_Plus_PM |
| 7 | 1556186_PM_s_at | EMC1 | ER membrane protein complex subunit 1 | HT_HG-U133_Plus_PM |
| 8 | 1556551_PM_s_at | SLC39A6 | solute carrier family 39 (zinc transporter), member 6 | HT_HG-U133_Plus_PM |
| 9 | 1556755_PM_s_at | LOC105375650 | uncharacterized LOC105375650 | HT_HG-U133_Plus_PM |
| 10 | 1556812_PM_a_at | — | gb: AF086041.1/DB_XREF = gi: 3483386/TID = Hs2.42975.1/CNT = 4/FEA = mRNA/TIER = ConsEnd/STK = 2/UG = Hs.42975/UG_TITLE = Homo sapiens full length insert cDNA clone YX53E08/DEF = Homo sapiens full length insert cDNA clone YX53E08. | HT_HG-U133_Plus_PM |
| 11 | 1556999_PM_at | LOC100271832 | uncharacterized LOC100271832 | HT_HG-U133_Plus_PM |
| 12 | 1557112_PM_a_at | VPS53 | vacuolar protein sorting 53 homolog (S. cerevisiae) | HT_HG-U133_Plus_PM |
| 13 | 1557265_PM_at | — | gb: BE242353/DB_XREF = gi: 9094081/DB_XREF = TCAAPIT2047/CLONE = TCAAP2047/TID = Hs2.255157.1/CNT = 9/FEA = mRNA/TIER = ConsEnd/STK = 1/UG = Hs.255157/UG_TITLE = Homo sapiens cDNA FLJ31889 fis, clone NT2RP7003091. | HT_HG-U133_Plus_PM |
| 14 | 1557276_PM_at | LINC01016 | long intergenic non-protein coding RNA 1016 | HT_HG-U133_Plus_PM |
| 15 | 1557615_PM_a_at | ARHGAP19-SLIT1 | ARHGAP19-SLIT1 readthrough (NMD candidate) | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| 16 | 1557744_PM_at | — | gb: AI978831/ DB_XREF = gi: 5803861/ DB_XREF = wr60c07.x1/ CLONE = IMAGE: 2492076/ TID = Hs2.375849.1/ CNT = 3/FEA = mRNA/ TIER = ConsEnd/STK = 1/ UG = Hs.375849/ UG_TITLE = Homo sapiens cDNA FLJ25841 fis, clone TST08665. | HT_HG-U133_Plus_PM |
| 17 | 1560263_PM_at | — | gb: BC016780.1/ DB_XREF = gi: 23271116/ TID = Hs2.396207.1/ CNT = 4/FEA = mRNA/ TIER = ConsEnd/STK = 0/ UG = Hs.396207/ UG_TITLE = Homo sapiens, clone IMAGE: 4106389, mRNA/ DEF = Homo sapiens, clone IMAGE: 4106389, mRNA. | HT_HG-U133_Plus_PM |
| 18 | 1560724_PM_at | — | gb: N93148/ DB_XREF = gi: 1265457/ DB_XREF = zb30b02.s1/ CLONE = IMAGE: 305067/ TID = Hs2.189084.1/ CNT = 3/FEA = mRNA/ TIER = ConsEnd/STK = 0/ UG = Hs.189084/ UG_TITLE = Homo sapiens cDNA FLJ33564 fis, clone BRAMY2010135. | HT_HG-U133_Plus_PM |
| 19 | 1561236_PM_at | | gb: BC035177.1/ DB_XREF = gi: 23273365/ TID = Hs2.385559.1/ CNT = 2/FEA = mRNA/ TIER = ConsEnd/STK = 1/ UG = Hs.385559/ UG_TITLE = Homo sapiens, clone IMAGE: 5266063, mRNA/ DEF = Homo sapiens, clone IMAGE: 5266063, mRNA. | HT_HG-U133_Plus_PM |
| 20 | 1562267_PM_s_at | ZNF709 | zinc finger protein 709 | HT_HG-U133_Plus_PM |
| 21 | 1562505_PM_at | — | gb: BC035700.1/ DB_XREF = gi: 23272849/ TID = Hs2.337138.1/ CNT = 2/FEA = mRNA/ TIER = ConsEnd/STK = 0/ UG = Hs.337138/ UG TITLE = Homo sapiens, clone IMAGE: 5550275, mRNA/ DEF = Homo sapiens, clone IMAGE: 5550275, mRNA. | HT_HG-U133_Plus_PM |
| 22 | 1564362_PM_x_at | ZNF843 | zinc finger protein 843 | HT_HG-U133_Plus_PM |
| 23 | 1566084_PM_at | — | gb: AK090649.1/ DB_XREF = gi: 21748852/ TID = Hs2.33074.1/ CNT = 3/FEA = mRNA/ TIER = ConsEnd/STK = 0/ UG = Hs.33074/ UG_TITLE = Homo sapiens cDNA FLJ40968 fis, clone | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| 24 | 1566145_PM_s_at | LOC101928669/// LOC101930100/// LOC644450 | UTERU2012615./ DEF = Homo sapiens cDNA FLJ33330 fis, clone BRACE2000441. uncharacterized LOC101928669/// uncharacterized LOC101930100/// uncharacterized LOC644450 | HT_HG-U133_Plus_PM |
| 25 | 1566671_PM_a_at | LOC105372824/// PDXK | uncharacterized protein C21orf124///pyridoxal (pyridoxine, vitamin B6) kinase | HT_HG-U133_Plus_PM |
| 26 | 1569496_PM_s_at | LOC100130872 | uncharacterized LOC100130872 | HT_HG-U133_Plus_PM |
| 27 | 1569521_PM_s_at | ERAP1/// LOC101929747 | endoplasmic reticulum aminopeptidase 1/// uncharacterized LOC101929747 | HT_HG-U133_Plus_PM |
| 28 | 1569527_PM_at | — | gb: BC017275.1/ DB_XREF = gi: 23398506/ TID = Hs2.385730.1/ CNT = 3/FEA = mRNA/ TIER = ConsEnd/STK = 0/ UG = Hs.385730/ UG_TITLE = Homo sapiens, clone IMAGE: 4842907, mRNA/ DEF = Homo sapiens, clone IMAGE: 4842907, mRNA. | HT_HG-U133_Plus_PM |
| 29 | 1570388_PM_a_at | LOC101929800/// LOC440896 | uncharacterized LOC101929800/// uncharacterized LOC440896 | HT_HG-U133_Plus_PM |
| 30 | 200041_PM_s_at | ATP6V1G2-DDX39B/// DDX39B | ATP6V1G2-DDX39B readthrough (NMD candidate)///DEAD (Asp-Glu-Ala-Asp) box polypeptide 39B | HT_HG-U133_Plus_PM |
| 31 | 200805_PM_at | LMAN2 | lectin, mannose-binding 2 | HT_HG-U133_Plus_PM |
| 32 | 200928_PM_s_at | RAB14 | RAB14, member RAS oncogene family | HT_HG-U133_Plus_PM |
| 33 | 201127_PM_s_at | ACLY | ATP citrate lyase | HT_HG-U133_Plus_PM |
| 34 | 201222_PM_s_at | RAD23B | RAD23 homolog B, nucleotide excision repair protein | HT_HG-U133_Plus_PM |
| 35 | 201251_PM_at | PKM | pyruvate kinase, muscle | HT_HG-U133_Plus_PM |
| 36 | 202015_PM_x_at | — | gb: NM_006838.1/ DB_XREF = gi: 5803091/ GEN = MNPEP/ FEA = FLmRNA/ CNT = 160/ TID = Hs.78935.0/ TIER = FL/STK = 0/ UG = Hs.78935/ LL = 10988/DEF = Homo sapiens methionine aminopeptidase; eIF-2-associated p67 (MNPEP), mRNA./ PROD = methionine aminopeptidase; eIF-2-associated p67/ FL = gb: NM_006838.1 gb: U29607.1 | HT_HG-U133_Plus_PM |
| 37 | 203744_PM_at | HMGB3 | high mobility group box 3 | HT_HG-U133_Plus_PM |
| 38 | 203768_PM_s_at | STS | steroid sulfatase (microsomal), isozyme S | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| 39 | 204218_PM_at | ANAPC15 | anaphase promoting complex subunit 15 | HT_HG-U133_Plus_PM |
| 40 | 204701_PM_s_at | STOML1 | stomatin (EPB72)-like 1 | HT_HG-U133_Plus_PM |
| 41 | 204787_PM_at | VSIG4 | V-set and immunoglobulin domain containing 4 | HT_HG-U133_Plus_PM |
| 42 | 205743_PM_at | STAC | SH3 and cysteine rich domain | HT_HG-U133_Plus_PM |
| 43 | 205905_PM_s_at | MICA/// MICB | MHC class I polypeptide-related sequence A/// MHC class I polypeptide-related sequence B | HT_HG-U133_Plus_PM |
| 44 | 206123_PM_at | LLGL1 | lethal giant larvae homolog 1 (Drosophila) | HT_HG-U133_Plus_PM |
| 45 | 206663_PM_at | SP4 | Sp4 transcription factor | HT_HG-U133_Plus_PM |
| 46 | 206759_PM_at | FCER2 | Fc fragment of IgE, low affinity II, receptor for (CD23) | HT_HG-U133_Plus_PM |
| 47 | 207346_PM_at | STX2 | syntaxin 2 | HT_HG-U133_Plus_PM |
| 48 | 207688_PM_s_at |  | gb: NM_005538.1/ DB_XREF = gi: 5031794/ GEN = INHBC/ FEA = FLmRNA/CNT = 3/ TID = Hs.199538.0/ TIER = FL/STK = 0/ UG = Hs. 199538/ LL = 3626/DEF = Homo sapiens inhibin, beta C (INHBC), mRNA./ PROD = inhibin beta C subunit precursor/ FL = gb: NM_005538.1 | HT_HG-U133_Plus_PM |
| 49 | 208725_PM_at | EIF2S2 | eukaryotic translation initiation factor 2, subunit 2 beta, 38kDa | HT_HG-U133_Plus_PM |
| 50 | 208963_PM_x_at | FADS1 | fatty acid desaturase 1 | HT_HG-U133_Plus_PM |
| 51 | 208997_PM_s_at | UCP2 | uncoupling protein 2 (mitochondrial, proton carrier) | HT_HG-U133_Plus_PM |
| 52 | 209321_PM_s_at | ADCY3 | adenylate cyclase 3 | HT_HG-U133_Plus_PM |
| 53 | 209331_PM_s_at | MAX | MYC associated factor X | HT_HG-U133_Plus_PM |
| 54 | 209410_PM_s_at | GRB10 | growth factor receptor bound protein 10 | HT_HG-U133_Plus_PM |
| 55 | 209415_PM_at | FZR1 | fizzy/cell division cycle 20 related 1 | HT_HG-U133_Plus_PM |
| 56 | 209568_PM_s_at | RGL1 | ral guanine nucleotide dissociation stimulator-like 1 | HT_HG-U133_Plus_PM |
| 57 | 209586_PM_s_at | PRUNE | prune exopolyphosphatase | HT_HG-U133_Plus_PM |
| 58 | 209913_PM_x_at | AP5Z1 | adaptor-related protein complex 5, zeta 1 subunit | HT_HG-U133_Plus_PM |
| 59 | 209935_PM_at | ATP2C1 | ATPase, Ca++ transporting, type 2C, member 1 | HT_HG-U133_Plus_PM |
| 60 | 210253_PM_at | HTATIP2 | HIV-1 Tat interactive protein 2 | HT_HG-U133_Plus_PM |
| 61 | 211022_PM_s_at | ATRX | alpha thalassemia/mental retardation syndrome X-linked | HT_HG-U133_Plus_PM |
| 62 | 211435_PM_at | — | gb: AF202635.1/ DB_XREF = gi: 10732645/ FEA = FLmRNA/CNT = 1/ TID = Hs.302135.0/ TIER = FL/STK = 0/ UG = Hs.302135/ DEF = Homo sapiens PP1200 mRNA, complete cds./PROD = PP1200/ FL = gb: AF202635.1 | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| 63 | 211578_PM_s_at | RPS6KB1 | ribosomal protein S6 kinase, 70kDa, polypeptide 1 | HT_HG-U133_Plus_PM |
| 64 | 211598_PM_x_at | VIPR2 | vasoactive intestinal peptide receptor 2 | HT_HG-U133_Plus_PM |
| 65 | 211977_PM_at | GPR107 | G protein-coupled receptor 107 | HT_HG-U133_Plus_PM |
| 66 | 212611_PM_at | DTX4 | deltex 4, E3 ubiquitin ligase | HT_HG-U133_Plus_PM |
| 67 | 213008_PM_at | FANCI | Fanconi anemia complementation group I | HT_HG-U133_Plus_PM |
| 68 | 213076_PM_at | ITPKC | inositol-trisphosphate 3-kinase C | HT_HG-U133_Plus_PM |
| 69 | 214195_PM_at | TPP1 | tripeptidyl peptidase I | HT_HG-U133_Plus_PM |
| 70 | 214289_PM_at | PSMB1 | proteasome subunit beta 1 | HT_HG-U133_Plus_PM |
| 71 | 214442_PM_s_at | PIAS2 | protein inhibitor of activated STAT 2 | HT_HG-U133_Plus_PM |
| 72 | 214510_PM_at | GPR20 | G protein-coupled receptor 20 | HT_HG-U133_Plus_PM |
| 73 | 214572_PM_s_at | INSL3 | insulin-like 3 (Leydig cell) | HT_HG-U133_Plus_PM |
| 74 | 214907_PM_at | CEACAM21 | carcinoembryonic antigen-related cell adhesion molecule 21 | HT_HG-U133_Plus_PM |
| 75 | 215233_PM_at | JMJD6 | jumonji domain containing 6 | HT_HG-U133_Plus_PM |
| 76 | 215641_PM_at | SEC24D | SEC24 homolog D, COPII coat complex component | HT_HG-U133_Plus_PM |
| 77 | 216517_PM_at | IGKC/// IGKV1-8/// IGKV1-9/// IGKV1D-8 | immunoglobulin kappa constant/// immunoglobulin kappa variable 1-8/// immunoglobulin kappa variable 1-9/// immunoglobulin kappa variable 1D-8 | HT_HG-U133_Plus_PM |
| 78 | 216951_PM_at | FCGR1A | Fc fragment of IgG, high affinity Ia, receptor (CD64) | HT_HG-U133_Plus_PM |
| 79 | 217137_PM_x_at | — | gb: K00627.1/ DB_XREF = gi: 337653/ FEA = mRNA/CNT = 1/ TID = Hs.203776.0/ TIER = ConsEnd/STK = 0/ UG = Hs.203776/ UG_TITLE = Human kpni repeat mrna (cdna clone pcd-kpni-8), 3 end/ DEF = human kpni repeat mrna (cdna clone pcd-kpni-8), 3 end. | HT_HG-U133 Plus_PM |
| 80 | 217436_PM_x_at | HLA-J | major histocompatibility complex, class I, J (pseudogene) | HT_HG-U133_Plus_PM |
| 81 | 217622_PM_at | RHBDD3 | rhomboid domain containing 3 | HT_HG-U133_Plus_PM |
| 82 | 218332_PM_at | BEX1 | brain expressed X-linked 1 | HT_HG-U133_Plus_PM |
| 83 | 219925_PM_at | ZMYM6 | zinc finger, MYM-type 6 | HT_HG-U133_Plus_PM |
| 84 | 219966_PM_x_at | BANP | BTG3 associated nuclear protein | HT_HG-U133_Plus_PM |
| 85 | 219980_PM_at | ABHD18 | abhydrolase domain containing 18 | HT_HG-U133_Plus_PM |
| 86 | 220315_PM_at | PARP11 | poly(ADP-ribose) polymerase family member 11 | HT_HG-U133_Plus_PM |
| 87 | 220396_PM_at | LOC105369820 | uncharacterized LOC105369820 | HT_HG-U133_Plus_PM |
| 88 | 220575_PM_at | FAM106A | family with sequence similarity 106, member A | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| 89 | 221041_PM_s_at | SLC17A5 | solute carrier family 17 (acidic sugar transporter), member 5 | HT_HG-U133_Plus_PM |
| 90 | 221959_PM_at | FAM110B | family with sequence similarity 110, member B | HT_HG-U133_Plus_PM |
| 91 | 221992_PM_at | NPIP/// NPIPA1/// NPIPB15/// NPIPB6/// NPIPB8/// NPIPB9/// PDXDC2P | nuclear pore complex interacting protein family, member A1 pseudogene/// nuclear pore complex interacting protein family, member A1/// nuclear pore complex interacting protein family, member B15/// nuclear pore complex interacting protein family, member B6/// nuclear pore complex interacting protein family, member B8/// nuclear pore complex interacting protein family, member B9/// pyridoxal-dependent decarboxylase domain containing 2, pseudogene | HT_HG-U133_Plus_PM |
| 92 | 222364_PM_at | SLC44A1 | solute carrier family 44 (choline transporter), member 1 | HT_HG-U133_Plus_PM |
| 93 | 222419_PM_x_at | UBE2H | ubiquitin conjugating enzyme E2H | HT_HG-U133_Plus_PM |
| 94 | 222615_PM_s_at | LOC100630923/// PRKRIP1 | LOC100289561-PRKRIP1 readthrough/// PRKR interacting protein 1 (IL11 inducible) | HT_HG-U133_Plus_PM |
| 95 | 222799_PM_at | WDR91 | WD repeat domain 91 | HT_HG-U133_Plus_PM |
| 96 | 222889_PM_at | DCLRE1B | DNA cross-link repair 1B | HT_HG-U133_Plus_PM |
| 97 | 223621_PM_at | PNMA3 | paraneoplastic Ma antigen 3 | HT_HG-U133_Plus_PM |
| 98 | 224549_PM_x_at | — | gb: AF194537.1/ DB_XREF = gi: 11037116/ GEN = NAG13/ FEA = FLmRNA/CNT = 1/ TID = HsAffx.900497.1131/ TIER = FL/STK = 0/ DEF = Homo sapiens NAG13 (NAG13) mRNA, complete cds./ PROD = NAG13/ FL = gb: AF194537.1 | HT_HG-U133_Plus_PM |
| 99 | 224559_PM_at | MALAT1 | metastasis associated lung adenocarcinoma transcript 1 (non-protein coding) | HT_HG-U133_Plus_PM |
| 100 | 224840_PM_at | FKBP5 | FK506 binding protein 5 | HT_HG-U133_Plus_PM |
| 101 | 224954_PM_at | SHMT1 | serine hydroxymethyltransferase 1 (soluble) | HT_HG-U133_Plus_PM |
| 102 | 225759_PM_x_at | CLMN | calmin (calponin-like, transmembrane) | HT_HG-U133_Plus_PM |
| 103 | 225959_PM_s_at | ZNRF1 | zinc and ring finger 1, E3 ubiquitin protein ligase | HT_HG-U133_Plus_PM |
| 104 | 226137_PM_at | ZFHX3 | zinc finger homeobox 3 | HT_HG-U133_Plus_PM |
| 105 | 226450_PM_at | INSR | insulin receptor | HT_HG-U133_Plus_PM |
| 106 | 226540_PM_at | CFAP73 | cilia and flagella associated protein 73 | HT_HG-U133_Plus_PM |
| 107 | 226599_PM_at | FHDC1 | FH2 domain containing 1 | HT_HG-U133_Plus_PM |
| 108 | 226699_PM_at | FCHSD1 | FCH and double SH3 domains 1 | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| 109 | 226856_PM_at | MUSTN1 | musculoskeletal, embryonic nuclear protein 1 | HT_HG-U133_Plus_PM |
| 110 | 227052_PM_at | SMIM14 | small integral membrane protein 14 | HT_HG-U133_Plus_PM |
| 111 | 227053_PM_at | PACSIN1 | protein kinase C and casein kinase substrate in neurons 1 | HT_HG-U133_Plus_PM |
| 112 | 227106_PM_at | TMEM198B | transmembrane protein 198B, pseudogene | HT_HG-U133_Plus_PM |
| 113 | 227333_PM_at | DCUN1D3 | DCN1, defective in cullin neddylation 1, domain containing 3 | HT_HG-U133_Plus_PM |
| 114 | 227709_PM_at | TPT1-AS1 | TPT1 antisense RNA 1 | HT_HG-U133_Plus_PM |
| 115 | 227710_PM_s_at | TPT1-AS1 | TPT1 antisense RNA 1 | HT_HG-U133_Plus_PM |
| 116 | 227743_PM_at | MYO15B | myosin XVB | HT_HG-U133_Plus_PM |
| 117 | 228209_PM_at | ACBD6/// LHX4-AS1 | acyl-CoA binding domain containing 6///LHX4 antisense RNA 1 | HT_HG-U133_Plus_PM |
| 118 | 228610_PM_at | TM9SF3 | transmembrane 9 superfamily member 3 | HT_HG-U133_Plus_PM |
| 119 | 228786_PM_at | SVIL-AS1 | SVIL antisense RNA 1 | HT_HG-U133_Plus_PM |
| 120 | 228928_PM_x_at | BANP | BTG3 associated nuclear protein | HT_HG-U133_Plus_PM |
| 121 | 229525_PM_at | — | gb: AW118132/ DB_XREF = gi: 6086716/ DB_XREF = xe03f10.x1/ CLONE = IMAGE: 2606059/ FEA = EST/CNT = 20/ TID = Hs.288151.1/ TIER = Stack/STK = 12/ UG = Hs.288151/ LL = 80145/ UG_GENE = FLJ23445/ UG_TITLE = hypothetical protein FLJ23445 | HT_HG-U133_Plus_PM |
| 122 | 229972_PM_at | LOC101926963 | uncharacterized LOC101926963 | HT_HG-U133_Plus_PM |
| 123 | 230057_PM_at | LOC285178 | uncharacterized LOC285178 | HT_HG-U133_Plus_PM |
| 124 | 230202_PM_at | — | gb: AI703057/ DB_XREF = gi: 4990957/ DB_XREF = wd81c08.x1/ CLONE = IMAGE: 2337998/ FEA = EST/CNT = 25/ TID = Hs.75569.2/ TIER = Stack/STK = 10/ UG = Hs.75569/LL = 5970/ UG_GENE = RELA/ UG_TITLE = v-rel avian reticuloendotheliosis viral oncogene homolog A (nuclear factor of kappa light polypeptide gene enhancer in B-cells 3 (p65)) | HT_HG-U133_Plus_PM |
| 125 | 230699_PM_at | PGLS | 6-phosphogluconolactonase | HT_HG-U133_Plus_PM |
| 126 | 231252_PM_at | KANSL1L | KAT8 regulatory NSL complex subunit 1 like | HT_HG-U133_Plus_PM |
| 127 | 231854_PM_at | PIK3CA | phosphatidylinositol-4,5-bisphosphate 3-kinase, catalytic subunit alpha | HT_HG-U133_Plus_PM |
| 128 | 231937_PM_at | — | gb: AU153281/ DB_XREF = gi: 11014802/ DB_XREF = AU153281/ CLONE = NT2RP3002799/ FEA = mRNA/CNT = 20/ TID = Hs.185707.0/ TIER = ConsEnd/STK = 4/ UG = Hs.185707/ | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| 129 | 232622_PM_at | — | UG_TITLE = Homo sapiens cDNA FLJ14200 fis, clone NT2RP3002799 gb: AK023865.1/ DB_XREF = gi: 10435932/ FEA = mRNA/CNT = 6/ TID = Hs.186104.0/ TIER = ConsEnd/STK = 0/ UG = Hs.186104/ UG_TITLE = Homo sapiens cDNA FLJ13803 fis, clone THYRO1000187/ DEF = Homo sapiens cDNA FLJ13803 fis, clone THYRO1000187. | HT_HG-U133_Plus_PM |
| 130 | 232864_PM_s_at | AFF4 | AF4/FMR2 family, member 4 | HT_HG-U133_Plus_PM |
| 131 | 232975_PM_at | HCG18 | HLA complex group 18 (non-protein coding) | HT_HG-U133_Plus_PM |
| 132 | 233678_PM_at | — | gb: AL442094.1/ DB_XREF = gi: 10241769/ FEA = mRNA /CNT = 2/ TID = Hs.306925.0/ TIER = ConsEnd/STK = 0/ UG = Hs.306925/ UG_TITLE = Homo sapiens mRNA; cDNA DKFZp547E024 (from clone DKFZp547E024)/ DEF = Homo sapiens mRNA; cDNA DKFZp547E024 (from clone DKFZp547E024). | HT_HG-U133_Plus_PM |
| 133 | 233762_PM_at | — | gb: AU158436/ DB_XREF = gi: 11019957/ DB_XREF = AU158436/ CLONE = PLACE2000379/ FEA = mRNA/CNT = 2/ TID = Hs.296742.0/ TIER = ConsEnd/STK = 1/ UG-Hs.296742/ UG_TITLE = Homo sapiens cDNA FLJ13711 fis, clone PLACE2000379 | HT_HG-U133_Plus_PM |
| 134 | 233779_PM_x_at | — | gb: AK022046.1/ DB_XREF = gi: 10433365/ FEA = mRNA /CNT = 3/ TID = Hs.293922.0/ TIER = ConsEnd/STK = 0/ UG = Hs.293922/ UG_TITLE = Homo sapiens cDNA FLJ11984 fis, clone HEMBB1001348/ DEF = Homo sapiens CDNA FLJ11984 fis, clone HEMBB1001348. | HT_HG-U133_Plus_PM |
| 135 | 234041_PM_at | — | gb: AK026269.1/ DB_XREF = gi: 10439072/ FEA = mRNA/CNT = 2/ TID = Hs.287704.0/ TIER = ConsEnd/STK = 0/ UG = Hs.287704/ UG_TITLE = Homo sapiens cDNA: FLJ22616 fis, clone HSI05164/ DEF = Homo sapiens CDNA: FLJ22616 fis, clone HSI05164. | HT_HG-U133_Plus_PM |
| 136 | 235596_PM_at | — | gb: BE562520/ DB_XREF = gi: 9806240/ DB_XREF = 601335817F1/ CLONE = IMAGE: 3689740/ FEA = EST/CNT = 12/ | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| | | | TID = Hs. 125720.0/<br>TIER = ConsEnd/STK = 0/<br>UG = Hs.125720/<br>UG_TITLE = ESTs | |
| 137 | 235823_PM_at | ACSF3 | acyl-CoA synthetase family member 3 | HT_HG-U133_Plus_PM |
| 138 | 236072_PM_at | — | gb: N64578/<br>DB_XREF = gi: 1212407/<br>DB_XREF = yz51d10.s1/<br>CLONE = IMAGE: 286579/<br>FEA = EST/CNT = 7/<br>TID = Hs.49014.0/<br>TIER = ConsEnd/STK = 5/<br>UG = Hs.49014/<br>UG_TITLE = ESTs, Weakly similar to AF116721 112 PRO2738 (H.sapiens) | HT_HG-U133_Plus_PM |
| 139 | 236706_PM_at | LYG1 | lysozyme G-like 1 | HT_HG-U133_Plus_PM |
| 140 | 236962_PM_at | — | gb: AA521018/<br>DB_XREF = gi: 2261561/<br>DB_XREF = aa70f07.s1/<br>CLONE = IMAGE: 826309/<br>FEA = EST/CNT = 7/<br>TID = Hs.104419.0/<br>TIER = ConsEnd/STK = 5/<br>UG = Hs.104419/<br>UG_TITLE = ESTs | HT_HG-U133_Plus_PM |
| 141 | 237072_PM_at | — | gb: BF223935/<br>DB_XREF = gi: 11131129/<br>DB_XREF = 7q82b06.x1/<br>CLONE = IMAGE: 3704771/<br>FEA = EST/CNT = 5/<br>TID = Hs. 192125.0/<br>TIER = ConsEnd/STK = 5/<br>UG = Hs.192125/<br>UG_TITLE = ESTs | HT_HG-U133_Plus_PM |
| 142 | 237689_PM_at | — | gb: BF111108/<br>DB_XREF = gi: 10940798/<br>DB_XREF = 7n43f06.x1/<br>CLONE = IMAGE: 3567491/<br>FEA = EST/CNT = 7/<br>TID = Hs.144063.0/<br>TIER = ConsEnd/STK = 7/<br>UG = Hs.144063/<br>UG_TITLE = ESTs, Moderately similar to SYS_HUMAN SERYL-TRNA SYNTHETASE (H.sapiens) | HT_HG-U133_Plus_PM |
| 143 | 238797_PM_at | TRIM11 | tripartite motif containing 11 | HT_HG-U133_Plus_PM |
| 144 | 239114_PM_at | — | gb: BE048824/<br>DB_XREF = gi: 8365868/<br>DB_XREF = hr54b02.x1/<br>CLONE = IMAGE: 3132267/<br>FEA = EST/CNT = 5/<br>TID = Hs.188966.0/<br>TIER = ConsEnd/STK = 4/<br>UG = Hs.188966/<br>UG_TITLE = ESTs | HT_HG-U133_Plus_PM |
| 145 | 239557_PM_at | — | gb: AW474960/<br>DB_XREF = gi: 7045066/<br>DB_XREF = hb01e08.x1/<br>CLONE = IMAGE: 2881958/<br>FEA = EST/CNT = 5/<br>TID = Hs.182258.0/<br>TIER = ConsEnd/STK = 4/<br>UG = Hs.182258/<br>UG_TITLE = ESTs | HT_HG-U133_Plus_PM |
| 146 | 239772_PM_x_at | DHX30 | DEAH (Asp-Glu-Ala-His) box helicase 30 | HT_HG-U133_Plus_PM |
| 147 | 239957_PM_at | — | gb: AW510793/<br>DB_XREF = gi: 7148871/ | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| | | | DB_XREF = hd39h04.x1/ CLONE = IMAGE: 2911927/ FEA = EST/CNT = 5/ TID = Hs.240728.0/ TIER = ConsEnd/STK = 4/ UG = Hs.240728/ UG_TITLE = ESTs | |
| 148 | 241458_PM_at | — | gb: AI868267/ DB_XREF = gi: 5541283/ DB_XREF = tj42h12.x1/ CLONE = IMAGE: 2144231/ FEA = EST/CNT = 11/ TID = Hs.295848.0/ TIER = ConsEnd/STK = 3/ UG = Hs.295848/ UG_TITLE = ESTs | HT_HG-U133_Plus_PM |
| 149 | 241667_PM_x_at | — | gb: AI820891/ DB_XREF = gi: 5439970/ DB_XREF = qv30e01.x5/ CLONE = IMAGE: 1983096/ FEA = EST/CNT = 8/ TID = Hs. 145356.0/ TIER = ConsEnd/STK = 0/ UG = Hs.145356/ UG_TITLE = ESTs | HT_HG-U133_Plus_PM |
| 150 | 242176_PM_at | MEF2A | myocyte enhancer factor 2A | HT_HG-U133_Plus_PM |
| 151 | 242413_PM_at | — | gb: AI814925/ DB_XREF = gi: 5426140/ DB_XREF = wk68f11.x1/ CLONE = IMAGE: 2420589/ FEA = EST/CNT = 4/ TID = Hs.272102.0/ TIER = ConsEnd/STK = 3/ UG = Hs.272102/ UG = TITLE = ESTs | HT_HG-U133_Plus_PM |
| 152 | 243476_PM_at | LOC105371724/// NF1 | uncharacterized LOC105371724/// neurofibromin 1 | HT_HG-U133_Plus_PM |
| 153 | 243858_PM_at | — | gb: AA699970/ DB_XREF = gi: 2702933/ DB_XREF = zi65g08.s1/ CLONE = IMAGE: 435710/ FEA = EST/CNT = 3/ TID = Hs.186498.0/ TIER = ConsEnd/STK = 3/ UG = Hs.186498/ UG_TITLE = ESTs | HT_HG-U133_Plus_PM |
| 154 | 244047_PM_at | — | gb: AA447714/ DB_XREF = gi: 2161384/ DB_XREF = aa20c03.s1/ CLONE = IMAGE: 813796/ FEA = EST/CNT = 5/ TID = Hs. 152188.0/ TIER = ConsEnd/STK = 1/ UG = Hs.152188/ UG_TITLE = ESTs | HT_HG-U133_Plus_PM |
| 155 | 244702_PM_at | — | gb: AI654208/ DB_XREF = gi: 4738187/ DB_XREF = wb24f02.x1/ CLONE = IMAGE:2306619/ FEA = EST/CNT = 3/ TID = Hs.195381.0/ TIER = ConsEnd/STK = 3/ UG = Hs.195381/ UG_TITLE = ESTs | HT_HG-U133_Plus_PM |
| 156 | 244746_PM_at | SEMA6D | sema domain, transmembrane domain (TM), and cytoplasmic domain, (semaphorin) 6D | HT_HG-U133_Plus_PM |
| 157 | 35776_PM_at | ITSN1 | intersectin 1 | HT_HG-U133_Plus_PM |
| 158 | 49327_PM_at | SIRT3 | sirtuin 3 | HT_HG-U133_Plus_PM |

TABLE 2-continued

Example Alternate Genes for use in TX versus non-TX Detection

| # | Probeset ID | Gene Symbol | Gene Title | Array Name |
|---|---|---|---|---|
| 159 | 50314_PM_i_at | C20orf27 | chromosome 20 open reading frame 27 | HT_HG-U133_Plus_PM |

TABLE 3

Example 2 of Gene Signature for TX versus non-TX Discrimination

| # | Probeset ID | Gene Symbol | Gene Title | Array Name |
|---|---|---|---|---|
| 1 | 1553856_PM_s_at | P2RY10 | purinergic receptor P2Y, G-protein coupled, 10 | HT_HG-U133_Plus_PM |
| 2 | 1554608_PM_at | TGOLN2 | trans-golgi network protein 2 | HT_HG-U133_Plus_PM |
| 3 | 1555730_PM_a_at | CFL1 | cofilin 1 (non-muscle) | HT_HG-U133_Plus_PM |
| 4 | 1555812_PM_a_at | ARHGDIB | Rho GDP dissociation inhibitor (GDI) beta | HT_HG-U133_Plus_PM |
| 5 | 1556033_PM_at | LINC01138 | long intergenic non-protein coding RNA 1138 | HT_HG-U133_Plus_PM |
| 6 | 1557116_PM_at | APOL6 | apolipoprotein L, 6 | HT_HG-U133_Plus_PM |
| 7 | 1561058_PM_at | — | Homo sapiens cDNA clone IMAGE: 5278570. | HT_HG-U133_Plus_PM |
| 8 | 1562505_PM_at | — | Homo sapiens, clone IMAGE: 5550275, mRNA. | HT_HG-U133_Plus_PM |
| 9 | 1565913_PM_at | — | Homo sapiens full length insert cDNA clone YR04D03. | HT_HG-U133_Plus_PM |
| 10 | 1566129_PM_at | LIMS1 | LIM and senescent cell antigen-like domains 1 | HT_HG-U133_Plus_PM |
| 11 | 1570264_PM_at | — | Homo sapiens, clone IMAGE: 4337699, mRNA. | HT_HG-U133_Plus_PM |
| 12 | 200041_PM_s_at | ATP6V1G2-DDX39B///DDX39B | ATP6V1G2-DDX39B readthrough (NMD candidate)///DEAD (Asp-Glu-Ala-Asp) box polypeptide 39B | HT_HG-U133_Plus_PM |
| 13 | 200623_PM_s_at | CALM2///CALM3 | calmodulin 2 (phosphorylase kinase, delta)///calmodulin 3 (phosphorylase kinase, delta) | HT_HG-U133_Plus_PM |
| 14 | 200634_PM_at | PFN1 | profilin 1 | HT_HG-U133_Plus_PM |
| 15 | 200745_PM_s_at | GNB1 | guanine nucleotide binding protein (G protein), beta polypeptide 1 | HT_HG-U133_Plus_PM |
| 16 | 200885_PM_at | RHOC | ras homolog family member C | HT_HG-U133_Plus_PM |
| 17 | 201236_PM_s_at | BTG2 | BTG family, member 2 | HT_HG-U133_Plus_PM |
| 18 | 201251_PM_at | PKM | pyruvate kinase, muscle | HT_HG-U133_Plus_PM |
| 19 | 201537_PM_s_at | DUSP3 | dual specificity phosphatase 3 | HT_HG-U133_Plus_PM |
| 20 | 201612_PM_at | ALDH9A1 | aldehyde dehydrogenase 9 family, member A1 | HT_HG-U133_Plus_PM |
| 21 | 202080_PM_s_at | TRAK1 | trafficking protein, kinesin binding 1 | HT_HG-U133_Plus_PM |
| 22 | 202333_PM_s_at | UBE2B | ubiquitin conjugating enzyme E2B | HT_HG-U133_Plus_PM |
| 23 | 202366_PM_at | ACADS | acyl-CoA dehydrogenase, C-2 to C-3 short chain | HT_HG-U133_Plus_PM |
| 24 | 203273_PM_s_at | TUSC2 | tumor suppressor candidate 2 | HT_HG-U133_Plus_PM |
| 25 | 203921_PM_at | CHST2 | carbohydrate (N-acetylglucosamine-6-O) sulfotransferase 2 | HT_HG-U133_Plus_PM |
| 26 | 204516_PM_at | ATXN7 | ataxin 7 | HT_HG-U133_Plus_PM |
| 27 | 205297_PM_s_at | CD79B | CD79b molecule, immunoglobulin-associated beta | HT_HG-U133_Plus_PM |

TABLE 3-continued

Example 2 of Gene Signature for TX versus non-TX Discrimination

| # | Probeset ID | Gene Symbol | Gene Title | Array Name |
|---|---|---|---|---|
| 28 | 205495_PM_s_at | GNLY | granulysin | HT_HG-U133_Plus_PM |
| 29 | 205603_PM_s_at | DIAPH2 | diaphanous-related formin 2 | HT_HG-U133_Plus_PM |
| 30 | 205905_PM_s_at | MICA///MICB | MHC class I polypeptide-related sequence A///MHC class I polypeptide-related sequence B | HT_HG-U133_Plus_PM |
| 31 | 206652_PM_at | ZMYM5 | zinc finger, MYM-type 5 | HT_HG-U133_Plus_PM |
| 32 | 207194_PM_s_at | ICAM4 | intercellular adhesion molecule 4 (Landsteiner-Wiener blood group) | HT_HG-U133_Plus_PM |
| 33 | 208174_PM_x_at | ZRSR2 | zinc finger (CCCH type), RNA binding motif and serine/arginine rich 2 | HT_HG-U133_Plus_PM |
| 34 | 208784_PM_s_at | KLHDC3 | kelch domain containing 3 | HT_HG-U133_Plus_PM |
| 35 | 208997_PM_s_at | UCP2 | uncoupling protein 2 (mitochondrial, proton carrier) | HT_HG-U133_Plus_PM |
| 36 | 209199_PM_s_at | MEF2C | myocyte enhancer factor 2C | HT_HG-U133_Plus_PM |
| 37 | 209304_PM_x_at | GADD45B | growth arrest and DNA-damage-inducible, beta | HT_HG-U133_Plus_PM |
| 38 | 209306_PM_s_at | SWAP70 | SWAP switching B-cell complex 70kDa subunit | HT_HG-U133_Plus_PM |
| 39 | 210057_PM_at | SMG1 | SMG1 phosphatidylinositol 3-kinase-related kinase | HT_HG-U133_Plus_PM |
| 40 | 210125_PM_s_at | BANF1 | barrier to autointegration factor 1 | HT_HG-U133_Plus_PM |
| 41 | 210253_PM_at | HTATIP2 | HIV-1 Tat interactive protein 2 | HT_HG-U133_Plus_PM |
| 42 | 210356_PM_x_at | MS4A1 | membrane-spanning 4-domains, subfamily A, member 1 | HT_HG-U133_Plus_PM |
| 43 | 210985_PM_s_at | SP100 | SP100 nuclear antigen | HT_HG-U133_Plus_PM |
| 44 | 210996_PM_s_at | YWHAE | tyrosine 3-monooxygenase/tryptophan 5-monooxygenase activation protein, epsilon | HT_HG-U133_Plus_PM |
| 45 | 210999_PM_s_at | GRB10 | growth factor receptor bound protein 10 | HT_HG-U133_Plus_PM |
| 46 | 211207_PM_s_at | ACSL6 | acyl-CoA synthetase long-chain family member 6 | HT_HG-U133_Plus_PM |
| 47 | 212099_PM_at | RHOB | ras homolog family member B | HT_HG-U133_Plus_PM |
| 48 | 212386_PM_at | TCF4 | transcription factor 4 | HT_HG-U133_Plus_PM |
| 49 | 212467_PM_at | DNAJC13 | DnaJ (Hsp40) homolog, subfamily C, member 13 | HT_HG-U133_Plus_PM |
| 50 | 212762_PM_s_at | TCF7L2 | transcription factor 7-like 2 (T-cell specific, HMG-box) | HT_HG-U133_Plus_PM |
| 51 | 213286_PM_at | ZFR | zinc finger RNA binding protein | HT_HG-U133_Plus_PM |
| 52 | 214511_PM_x_at | FCGR1B | Fc fragment of IgG, high affinity Ib, receptor (CD64) | HT_HG-U133_Plus_PM |
| 53 | 214669_PM_x_at | IGK///IGKC///IGKV1-5///IGKV3-20///IGKV3D-20 | immunoglobulin kappa locus///immunoglobulin kappa constant///immunoglobulin kappa variable 1-5///immunoglobulin kappa variable 3-20///immunoglobulin kappa variable 3D-20 | HT_HG-U133_Plus_PM |
| 54 | 214907_PM_at | CEACAM21 | carcinoembryonic antigen-related cell adhesion molecule 21 | HT_HG-U133_Plus_PM |
| 55 | 216069_PM_at | PRMT2 | protein arginine methyltransferase 2 | HT_HG-U133_Plus_PM |
| 56 | 216950_PM_s_at | FCGR1A///FCGR1C | Fc fragment of IgG, high affinity Ia, receptor (CD64)///Fc fragment of IgG, high affinity Ic, receptor (CD64), pseudogene | HT_HG-U133_Plus_PM |

TABLE 3-continued

Example 2 of Gene Signature for TX versus non-TX Discrimination

| # | Probeset ID | Gene Symbol | Gene Title | Array Name |
|---|---|---|---|---|
| 57 | 217418_PM_x_at | MS4A1 | membrane-spanning 4-domains, subfamily A, member 1 | HT_HG-U133_Plus_PM |
| 58 | 217436_PM_x_at | HLA-J | major histocompatibility complex, class I, J (pseudogene) | HT_HG-U133_Plus_PM |
| 59 | 217979_PM_at | TSPAN13 | tetraspanin 13 | HT_HG-U133_Plus_PM |
| 60 | 217991_PM_x_at | SSBP3 | single stranded DNA binding protein 3 | HT_HG-U133_Plus_PM |
| 61 | 218438_PM_s_at | MED28 | mediator complex subunit 28 | HT_HG-U133_Plus_PM |
| 62 | 218527_PM_at | APTX | aprataxin | HT_HG-U133_Plus_PM |
| 63 | 219100_PM_at | OBFC1 | oligonucleotide/oligosaccharide-binding fold containing 1 | HT_HG-U133_Plus_PM |
| 64 | 219191_PM_s_at | BIN2 | bridging integrator 2 | HT_HG-U133_Plus_PM |
| 65 | 219233_PM_s_at | GSDMB | gasdermin B | HT_HG-U133_Plus_PM |
| 66 | 219471_PM_at | KIAA0226L | KIAA0226-like | HT_HG-U133_Plus_PM |
| 67 | 219938_PM_s_at | PSTPIP2 | proline-serine-threonine phosphatase interacting protein 2 | HT_HG-U133_Plus_PM |
| 68 | 219966_PM_x_at | BANP | BTG3 associated nuclear protein | HT_HG-U133_Plus_PM |
| 69 | 221013_PM_s_at | APOL2 | apolipoprotein L, 2 | HT_HG-U133_Plus_PM |
| 70 | 221508_PM_at | TAOK3 | TAO kinase 3 | HT_HG-U133_Plus_PM |
| 71 | 222471_PM_s_at | KCMF1 | potassium channel modulatory factor 1 | HT_HG-U133_Plus_PM |
| 72 | 222582_PM_at | PRKAG2 | protein kinase, AMP-activated, gamma 2 non-catalytic subunit | HT_HG-U133_Plus_PM |
| 73 | 222799_PM_at | WDR91 | WD repeat domain 91 | HT_HG-U133_Plus_PM |
| 74 | 222891_PM_s_at | BCL11A | B-cell CLL/lymphoma 11A (zinc finger protein) | HT_HG-U133_Plus_PM |
| 75 | 222996_PM_s_at | CXXC5 | CXXC finger protein 5 | HT_HG-U133_Plus_PM |
| 76 | 223465_PM_at | COL4A3BP | collagen, type IV, alpha 3 (Goodpasture antigen) binding protein | HT_HG-U133_Plus_PM |
| 77 | 223950_PM_s_at | FLYWCH1 | FLYWCH-type zinc finger 1 | HT_HG-U133_Plus_PM |
| 78 | 224516_PM_s_at | CXXC5 | CXXC finger protein 5 | HT_HG-U133_Plus_PM |
| 79 | 224549_PM_x_at | — | Homo sapiens NAG13 (NAG13) mRNA, complete cds | HT_HG-U133_Plus_PM |
| 80 | 224559_PM_at | MALAT1 | metastasis associated lung adenocarcinoma transcript 1 (non-protein coding) | HT_HG-U133_Plus_PM |
| 81 | 224767_PM_at | LOC100506548///RPL37 | uncharacterized LOC100506548///ribosomal protein L37 | HT_HG-U133_Plus_PM |
| 82 | 224840_PM_at | FKBP5 | FK506 binding protein 5 | HT_HG-U133_Plus_PM |
| 83 | 225012_PM_at | HDLBP | high density lipoprotein binding protein | HT_HG-U133_Plus_PM |
| 84 | 225108_PM_at | AGPS | alkylglycerone phosphate synthase | HT_HG-U133_Plus_PM |
| 85 | 225232_PM_at | MTMR12 | myotubularin related protein 12 | HT_HG-U133_Plus_PM |
| 86 | 225294_PM_s_at | TRAPPC1 | trafficking protein particle complex 1 | HT_HG-U133_Plus_PM |
| 87 | 225870_PM_s_at | TRAPPC5 | trafficking protein particle complex 5 | HT_HG-U133_Plus_PM |
| 88 | 225933_PM_at | CCDC137 | coiled-coil domain containing 137 | HT_HG-U133_Plus_PM |
| 89 | 226518_PM_at | KCTD10 | potassium channel tetramerization domain containing 10 | HT_HG-U133_Plus_PM |
| 90 | 227052_PM_at | SMIM14 | small integral membrane protein 14 | HT_HG-U133_Plus_PM |

TABLE 3-continued

Example 2 of Gene Signature for TX versus non-TX Discrimination

| # | Probeset ID | Gene Symbol | Gene Title | Array Name |
|---|---|---|---|---|
| 91 | 227410_PM_at | FAM43A | family with sequence similarity 43, member A | HT_HG-U133_Plus_PM |
| 92 | 227458_PM_at | CD274 | CD274 molecule | HT_HG-U133_Plus_PM |
| 93 | 227787_PM_s_at | MED30 | mediator complex subunit 30 | HT_HG-U133_Plus_PM |
| 94 | 228928_PM_x_at | BANP | BTG3 associated nuclear protein | HT_HG-U133_Plus_PM |
| 95 | 229187_PM_at | LOC283788 | FSHD region gene 1 pseudogene | HT_HG-U133_Plus_PM |
| 96 | 231035_PM_s_at | OTUD1 | OTU deubiquitinase 1 | HT_HG-U133_Plus_PM |
| 97 | 232340_PM_at | MIATNB | MIAT neighbor (non-protein coding) | HT_HG-U133_Plus_PM |
| 98 | 232375_PM_at | — | Homo sapiens cDNA FLJ12169 fis, clone MAMMA1000643 | HT_HG-U133_Plus_PM |
| 99 | 232405_PM_at | — | Homo sapiens cDNA: FLJ22832 fis, clone KAIA4195 | HT_HG-U133_Plus_PM |
| 100 | 232420_PM_x_at | MAN1B1-AS1 | MAN1B1 antisense RNA 1 (head to head) | HT_HG-U133_Plus_PM |
| 101 | 232864_PM_s_at | AFF4 | AF4/FMR2 family, member 4 | HT_HG-U133_Plus_PM |
| 102 | 233186_PM_s_at | BANP | BTG3 associated nuclear protein | HT_HG-U133_Plus_PM |
| 103 | 233309_PM_at | — | Homo sapiens cDNA FLJ11759 fis, clone HEMBA1005616 | HT_HG-U133_Plus_PM |
| 104 | 235461_PM_at | TET2 | tet methylcytosine dioxygenase 2 | HT_HG-U133_Plus_PM |
| 105 | 235533_PM_at | COX19 | COX19 cytochrome c oxidase assembly factor | HT_HG-U133_Plus_PM |
| 106 | 235645_PM_at | ESCO1 | establishment of sister chromatid cohesion N-acetyltransferase 1 | HT_HG-U133_Plus_PM |
| 107 | 236298_PM_at | PDSS1 | prenyl (decaprenyl) diphosphate synthase, subunit 1 | HT_HG-U133_Plus_PM |
| 108 | 239294_PM_at | PIK3CG | phosphatidylinositol-4,5-bisphosphate 3-kinase, catalytic subunit gamma | HT_HG-U133_Plus_PM |
| 109 | 240008_PM_at | — | Homo sapiens cDNA, 3' end/ clone = IMAGE-1703976/ clone_end = 3'/gb = AI161200/ gi = 3694505/ug = Hs.146907/ len = 424 | HT_HG-U133_Plus_PM |
| 110 | 242014_PM_at | | DB_XREF = wb18h06.x1/ CLONE = IMAGE:2306075 | HT_HG-U133_Plus_PM |
| 111 | 242374_PM_at | — | nx92b05.s1 Homo sapiens cDNA/clone = IMAGE-1269681/gb = AA747563/ gi = 2787521/ug = Hs.131799/ len = 325 | HT_HG-U133_Plus_PM |
| 112 | 242751_PM_at | — | qu42g07.x1 Homo sapiens cDNA, 3' end/clone = IMAGE-1967484/clone_end = 3'/ gb = AI281464/gi = 3919697/ ug = Hs.38038/len = 387 | HT_HG-U133_Plus_PM |
| 113 | 242918_PM_at | NASP | nuclear autoantigenic sperm protein (histone-binding) | HT_HG-U133_Plus_PM |
| 114 | 243417_PM_at | ZADH2 | zinc binding alcohol dehydrogenase domain containing 2 | HT_HG-U133_Plus_PM |
| 115 | 243981_PM_at | STK4 | serine/threonine kinase 4 | HT_HG-U133_Plus_PM |
| 116 | 244433_PM_at | — | accn = NULL class = lincRNA name = Human lincRNA ref = Scripture Reconstruction LincRNAs By Luo transcriptId = linc_luo_1183 cpcScore = −1.3227000 cnci = −0.4318137 | HT_HG-U133_Plus_PM |
| 117 | 44790_PM_s_at | KIAA0226L | KIAA0226-like | HT_HG-U133_Plus_PM |
| 118 | 50314_PM_i_at | C20orf27 | chromosome 20 open reading frame 27 | HT_HG-U133_Plus_PM |
| 119 | 54632_PM_at | THADA | thyroid adenoma associated | HT_HG-U133_Plus_PM |

TABLE 3-continued

Example 2 of Gene Signature for TX versus non-TX Discrimination

| # | Probeset ID | Gene Symbol | Gene Title | Array Name |
|---|---|---|---|---|
| 120 | 59644_PM_at | BMP2K | BMP2 inducible kinase | HT_HG-U133_Plus_PM |

TABLE 4

Example 2 Alternate Genes for use in TX versus non-TX Discrimination

| # | Probeset ID | Gene Symbol | Gene Title | Array Name |
|---|---|---|---|---|
| 1 | 1554608_PM_at | TGOLN2 | trans-golgi network protein 2 | HT_HG-U133_Plus_PM |
| 2 | 1555730_PM_a_at | CFL1 | cofilin 1 (non-muscle) | HT_HG-U133_Plus_PM |
| 3 | 1557116_PM_at | APOL6 | apolipoprotein L, 6 | HT_HG-U133_Plus_PM |
| 4 | 1561058_PM_at | — | *Homo sapiens* cDNA clone IMAGE: 5278570. | HT_HG-U133_Plus_PM |
| 5 | 1562505_PM_at | — | *Homo sapiens*, clone IMAGE: 5550275, mRNA. | HT_HG-U133_Plus_PM |
| 6 | 1565913_PM_at | — | *Homo sapiens* full length insert cDNA clone YR04D03. | HT_HG-U133_Plus_PM |
| 7 | 1566129_PM_at | LIMS1 | LIM and senescent cell antigen-like domains 1 | HT_HG-U133_Plus_PM |
| 8 | 1570264_PM_at | — | *Homo sapiens*, clone IMAGE: 4337699, mRNA. | HT_HG-U133_Plus_PM |
| 9 | 200041_PM_s_at | ATP6V1G2-DDX39B///DDX39B | ATP6V1G2-DDX39B readthrough (NMD candidate)///DEAD (Asp-Glu-Ala-Asp) box polypeptide 39B | HT_HG-U133_Plus_PM |
| 10 | 200885_PM_at | RHOC | ras homolog family member C | HT_HG-U133_Plus_PM |
| 11 | 201251_PM_at | PKM | pyruvate kinase, muscle | HT_HG-U133_Plus_PM |
| 12 | 201612_PM_at | ALDH9A1 | aldehyde dehydrogenase 9 family, member A1 | HT_HG-U133_Plus_PM |
| 13 | 202366_PM_at | ACADS | acyl-CoA dehydrogenase, C-2 to C-3 short chain | HT_HG-U133_Plus_PM |
| 14 | 203273_PM_s_at | TUSC2 | tumor suppressor candidate 2 | HT_HG-U133_Plus_PM |
| 15 | 205495_PM_s_at | GNLY | granulysin | HT_HG-U133_Plus_PM |
| 16 | 205905_PM_s_at | MICA///MICB | MHC class I polypeptide-related sequence A///MHC class I polypeptide-related sequence B | HT_HG-U133_Plus_PM |
| 17 | 206652_PM_at | ZMYM5 | zinc finger, MYM-type 5 | HT_HG-U133_Plus_PM |
| 18 | 207194_PM_s_at | ICAM4 | intercellular adhesion molecule 4 (Landsteiner-Wiener blood group) | HT_HG-U133_Plus_PM |
| 19 | 208174_PM_x_at | ZRSR2 | zinc finger (CCCH type), RNA binding motif and serine/arginine rich 2 | HT_HG-U133_Plus_PM |
| 20 | 208784_PM_s_at | KLHDC3 | kelch domain containing 3 | HT_HG-U133_Plus_PM |
| 21 | 208997_PM_s_at | UCP2 | uncoupling protein 2 (mitochondrial, proton carrier) | HT_HG-U133_Plus_PM |
| 22 | 209199_PM_s_at | MEF2C | myocyte enhancer factor 2C | HT_HG-U133_Plus_PM |
| 23 | 209304_PM_x_at | GADD45B | growth arrest and DNA-damage-inducible, beta | HT_HG-U133_Plus_PM |
| 24 | 209306_PM_s_at | SWAP70 | SWAP switching B-cell complex 70 kDa subunit | HT_HG-U133_Plus_PM |
| 25 | 210057_PM_at | SMG1 | SMG1 phosphatidylinositol 3-kinase-related kinase | HT_HG-U133_Plus_PM |

TABLE 4-continued

Example 2 Alternate Genes for use in TX versus non-TX Discrimination

| # | Probeset ID | Gene Symbol | Gene Title | Array Name |
|---|---|---|---|---|
| 26 | 210125_PM_s_at | BANF1 | barrier to autointegration factor 1 | HT_HG-U133_Plus_PM |
| 27 | 210253_PM_at | HTATIP2 | HIV-1 Tat interactive protein 2 | HT_HG-U133_Plus_PM |
| 28 | 210999_PM_s_at | GRB10 | growth factor receptor bound protein 10 | HT_HG-U133_Plus_PM |
| 29 | 211207_PM_s_at | ACSL6 | acyl-CoA synthetase long-chain family member 6 | HT_HG-U133_Plus_PM |
| 30 | 212099_PM_at | RHOB | ras homolog family member B | HT_HG-U133_Plus_PM |
| 31 | 212762_PM_s_at | TCF7L2 | transcription factor 7-like 2 (T-cell specific, HMG-box) | HT_HG-U133_Plus_PM |
| 32 | 214511_PM_x_at | FCGRIB | Fc fragment of IgG, high affinity Ib, receptor (CD64) | HT_HG-U133_Plus_PM |
| 33 | 214907_PM_at | CEACAM21 | carcinoembryonic antigen-related cell adhesion molecule 21 | HT_HG-U133_Plus_PM |
| 34 | 216950_PM_s_at | FCGR1A/// FCGRIC | Fc fragment of IgG, high affinity Ia, receptor (CD64)/// Fc fragment of IgG, high affinity Ic, receptor (CD64), pseudogene | HT_HG-U133_Plus_PM |
| 35 | 217436_PM_x_at | HLA-J | major histocompatibility complex, class I, J (pseudogene) | HT_HG-U133_Plus_PM |
| 36 | 217991_PM_x_at | SSBP3 | single stranded DNA binding protein 3 | HT_HG-U133_Plus_PM |
| 37 | 218438_PM_s_at | MED28 | mediator complex subunit 28 | HT_HG-U133_Plus_PM |
| 38 | 218527_PM_at | APTX | aprataxin | HT_HG-U133_Plus_PM |
| 39 | 219100_PM_at | OBFC1 | oligonucleotide/oligosaccharide-binding fold containing 1 | HT_HG-U133_Plus_PM |
| 40 | 219233_PM_s_at | GSDMB | gasdermin B | HT_HG-U133_Plus_PM |
| 41 | 219966_PM_x_at | BANP | BTG3 associated nuclear protein | HT_HG-U133_Plus_PM |
| 42 | 221013_PM_s_at | APOL2 | apolipoprotein L, 2 | HT_HG-U133_Plus_PM |
| 43 | 221508_PM_at | TAOK3 | TAO kinase 3 | HT_HG-U133_Plus_PM |
| 44 | 222471_PM_s_at | KCMF1 | potassium channel modulatory factor 1 | HT_HG-U133_Plus_PM |
| 45 | 222799_PM_at | WDR91 | WD repeat domain 91 | HT_HG-U133_Plus_PM |
| 46 | 223465_PM_at | COL4A3BP | collagen, type IV, alpha 3 (Goodpasture antigen) binding protein | HT_HG-U133_Plus_PM |
| 47 | 223950_PM_s_at | FLYWCH1 | FLYWCH-type zinc finger 1 | HT_HG-U133_Plus_PM |
| 48 | 224549_PM_x_at | — | *Homo sapiens* NAG13 (NAG13) mRNA, complete cds | HT_HG-U133_Plus_PM |
| 49 | 224559_PM_at | MALAT1 | metastasis associated lung adenocarcinoma transcript 1 (non-protein coding) | HT_HG-U133_Plus_PM |
| 50 | 224840_PM_at | FKBP5 | FK506 binding protein 5 | HT_HG-U133_Plus_PM |
| 51 | 225012_PM_at | HDLBP | high density lipoprotein binding protein | HT_HG-U133_Plus_PM |
| 52 | 225294_PM_s_at | TRAPPC1 | trafficking protein particle complex 1 | HT_HG-U133_Plus_PM |
| 53 | 225870_PM_s_at | TRAPPC5 | trafficking protein particle complex 5 | HT_HG-U133_Plus_PM |
| 54 | 225933_PM_at | CCDC137 | coiled-coil domain containing 137 | HT_HG-U133_Plus_PM |
| 55 | 226518_PM_at | KCTD10 | potassium channel tetramerization domain containing 10 | HT_HG-U133_Plus_PM |
| 56 | 227052_PM_at | SMIM14 | small integral membrane protein 14 | HT_HG-U133_Plus_PM |
| 57 | 227458_PM_at | CD274 | CD274 molecule | HT_HG-U133_Plus_PM |

TABLE 4-continued

Example 2 Alternate Genes for use in TX versus non-TX Discrimination

| # | Probeset ID | Gene Symbol | Gene Title | Array Name |
|---|---|---|---|---|
| 58 | 227787_PM_s_at | MED30 | mediator complex subunit 30 | HT_HG-U133_Plus_PM |
| 59 | 228928_PM_x_at | BANP | BTG3 associated nuclear protein | HT_HG-U133_Plus_PM |
| 60 | 229187_PM_at | LOC283788 | FSHD region gene 1 pseudogene | HT_HG-U133_Plus_PM |
| 61 | 232375_PM_at | — | Homo sapiens cDNA FLJ12169 fis, clone MAMMA1000643 | HT_HG-U133_Plus_PM |
| 62 | 232405_PM_at | — | Homo sapiens cDNA: FLJ22832 fis, clone KAIA4195 | HT_HG-U133_Plus_PM |
| 63 | 232864_PM_s_at | AFF4 | AF4/FMR2 family, member 4 | HT_HG-U133_Plus_PM |
| 64 | 233186_PM_s_at | BANP | BTG3 associated nuclear protein | HT_HG-U133_Plus_PM |
| 65 | 235533_PM_at | COX19 | COX19 cytochrome c oxidase assembly factor | HT_HG-U133_Plus_PM |
| 66 | 242751_PM_at | — | qu42g07.x1 Homo sapiens cDNA, 3' end /clone = IMAGE-1967484 /clone_end = 3' /gb = AI281464 /gi = 3919697 /ug = Hs.38038 /len = 387 | HT_HG-U133_Plus_PM |
| 67 | 243417_PM_at | ZADH2 | zinc binding alcohol dehydrogenase domain containing 2 | HT_HG-U133_Plus_PM |
| 68 | 50314_PM_i_at | C20orf27 | chromosome 20 open reading frame 27 | HT_HG-U133_Plus_PM |
| 69 | 59644_PM_at | BMP2K | BMP2 inducible kinase | HT_HG-U133_Plus_PM |

TABLE 5

Example Gene Set for use in TX versus subAR Discrimination

| # | Probeset ID | Gene Symbol | Gene Title | Array Name |
|---|---|---|---|---|
| 1 | 1555730_PM_a_at | CFL1 | cofilin 1 (non-muscle) | HT_HG-U133_Plus_PM |
| 2 | 1555812_PM_a_at | ARHGDIB | Rho GDP dissociation inhibitor (GDI) beta | HT_HG-U133_Plus_PM |
| 3 | 1555916_PM_at | RPUSD3 | RNA pseudouridylate synthase domain containing 3 | HT_HG-U133_Plus_PM |
| 4 | 1558525_PM_at | LOC101928595 | uncharacterized LOC101928595 | HT_HG-U133_Plus_PM |
| 5 | 1562460_PM_at | CNDP2 | CNDP dipeptidase 2 (metallopeptidase M20 family) | HT_HG-U133_Plus_PM |
| 6 | 1563641_PM_a_at | SNX20 | sorting nexin 20 | HT_HG-U133_Plus_PM |
| 7 | 1569189_PM_at | TTC9C | tetratricopeptide repeat domain 9C | HT_HG-U133_Plus_PM |
| 8 | 200041_PM_s_at | ATP6V1G2-DDX39B///DDX39B | ATP6V1G2-DDX39B readthrough (NMD candidate)///DEAD (Asp-Glu-Ala-Asp) box polypeptide 39B | HT_HG-U133_Plus_PM |
| 9 | 200613_PM_at | AP2M1 | adaptor-related protein complex 2, mu 1 subunit | HT_HG-U133_Plus_PM |
| 10 | 200634_PM_at | PFN1 | profilin 1 | HT_HG-U133_Plus_PM |
| 11 | 201040_PM_at | GNAI2 | guanine nucleotide binding protein (G protein), alpha inhibiting activity polypeptide 2 | HT_HG-U133_Plus_PM |
| 12 | 201234_PM_at | ILK | integrin linked kinase | HT_HG-U133_Plus_PM |

TABLE 5-continued

Example Gene Set for use in TX versus subAR Discrimination

| # | Probeset ID | Gene Symbol | Gene Title | Array Name |
|---|---|---|---|---|
| 13 | 201251_PM_at | PKM | pyruvate kinase, muscle | HT_HG-U133_Plus_PM |
| 14 | 201841_PM_s_at | HSPB1 | heat shock 27 kDa protein 1 | HT_HG-U133_Plus_PM |
| 15 | 201977_PM_s_at | KIAA0141 | KIAA0141 | HT_HG-U133_Plus_PM |
| 16 | 202009_PM_at | TWF2 | twinfilin actin binding protein 2 | HT_HG-U133_Plus_PM |
| 17 | 202358_PM_s_at | SNX19 | sorting nexin 19 | HT_HG-U133_Plus_PM |
| 18 | 203110_PM_at | PTK2B | protein tyrosine kinase 2 beta | HT_HG-U133_Plus_PM |
| 19 | 203536_PM_s_at | CIAO1 | cytosolic iron-sulfur assembly component 1 | HT_HG-U133_Plus_PM |
| 20 | 203671_PM_at | TPMT | thiopurine S-methyltransferase | HT_HG-U133 Plus_PM |
| 21 | 203729_PM_at | EMP3 | epithelial membrane protein 3 | HT_HG-U133_Plus_PM |
| 22 | 204191_PM_at | IFNAR1 | interferon (alpha, beta and omega) receptor 1 | HT_HG-U133_Plus_PM |
| 23 | 206949_PM_s_at | RUSC1 | RUN and SH3 domain containing 1 | HT_HG-U133_Plus_PM |
| 24 | 208997_PM_s_at | UCP2 | uncoupling protein 2 (mitochondrial, proton carrier) | HT_HG-U133_Plus_PM |
| 25 | 209936_PM_at | RBM5 | RNA binding motif protein 5 | HT_HG-U133_Plus_PM |
| 26 | 210889_PM_s_at | FCGR2B | Fc fragment of IgG, low affinity IIb, receptor (CD32) | HT_HG-U133_Plus_PM |
| 27 | 212431_PM_at | HMGXB3 | HMG box domain containing 3 | HT_HG-U133_Plus_PM |
| 28 | 213082_PM_s_at | SLC35D2 | solute carrier family 35 (UDP-GlcNAc/UDP-glucose transporter), member D2 | HT_HG-U133_Plus_PM |
| 29 | 214116_PM_at | BTD | biotinidase | HT_HG-U133_Plus_PM |
| 30 | 215399_PM_s_at | OS9 | osteosarcoma amplified 9, endoplasmic reticulum lectin | HT_HG-U133_Plus_PM |
| 31 | 217436_PM_x_at | HLA-J | major histocompatibility complex, class I, J (pseudogene) | HT_HG-U133_Plus_PM |
| 32 | 218776_PM_s_at | TMEM62 | transmembrane protein 62 | HT_HG-U133_Plus_PM |
| 33 | 219100_PM_at | OBFC1 | oligonucleotide/oligosaccharide-binding fold containing 1 | HT_HG-U133_Plus_PM |
| 34 | 219805_PM_at | CXorf56 | chromosome X open reading frame 56 | HT_HG-U133_Plus_PM |
| 35 | 221269_PM_s_at | SH3BGRL3 | SH3 domain binding glutamate-rich protein like 3 | HT_HG-U133_Plus_PM |
| 36 | 221657_PM_s_at | ASB6 | ankyrin repeat and SOCS box containing 6 | HT_HG-U133_Plus_PM |
| 37 | 221883_PM_at | PKNOX1 | PBX/knotted 1 homeobox 1 | HT_HG-U133_Plus_PM |
| 38 | 222026_PM_at | RBM3 | RNA binding motif (RNP1, RRM) protein 3 | HT_HG-U133_Plus_PM |
| 39 | 222064_PM_s_at | AARSD1/// PTGES3L-AARSDI | alanyl-tRNA synthetase domain containing 1/// PTGES3L-AARSD1 readthrough | HT_HG-U133_Plus_PM |
| 40 | 222165_PM_x_at | C9orf16 | chromosome 9 open reading frame 16 | HT_HG-U133_Plus_PM |
| 41 | 222471_PM_s_at | KCMF1 | potassium channel modulatory factor 1 | HT_HG-U133_Plus_PM |
| 42 | 222815_PM_at | RLIM | ring finger protein, LIM domain interacting | HT_HG-U133_Plus_PM |
| 43 | 223222_PM_at | SLC25A19 | solute carrier family 25 (mitochondrial thiamine pyrophosphate carrier), member 19 | HT_HG-U133_Plus_PM |

TABLE 5-continued

Example Gene Set for use in TX versus subAR Discrimination

| # | Probeset ID | Gene Symbol | Gene Title | Array Name |
|---|---|---|---|---|
| 44 | 223613_PM_at | UQCR11 | ubiquinol-cytochrome c reductase, complex III subunit XI | HT_HG-U133_Plus_PM |
| 45 | 224926_PM_at | EXOC4 | exocyst complex component 4 | HT_HG-U133_Plus_PM |
| 46 | 225208_PM_s_at | FAM103A1 | family with sequence similarity 103, member A1 | HT_HG-U133_Plus_PM |
| 47 | 225294_PM_s_at | TRAPPC1 | trafficking protein particle complex 1 | HT_HG-U133_Plus_PM |
| 48 | 225680_PM_at | LRWD1 | leucine-rich repeats and WD repeat domain containing 1 | HT_HG-U133_Plus_PM |
| 49 | 225947_PM_at | MYO19 | myosin XIX | HT_HG-U133_Plus_PM |
| 50 | 226035_PM_at | USP31 | ubiquitin specific peptidase 31 | HT_HG-U133_Plus_PM |
| 51 | 226644_PM_at | MIB2 | mindbomb E3 ubiquitin protein ligase 2 | HT_HG-U133_Plus_PM |
| 52 | 226696_PM_at | RBBP9 | retinoblastoma binding protein 9 | HT_HG-U133_Plus_PM |
| 53 | 227937_PM_at | MYPOP | Myb-related transcription factor, partner of profilin | HT_HG-U133_Plus_PM |
| 54 | 229035_PM_s_at | KLHDC4/// LOC105371397 | kelch domain containing 4/// uncharacterized LOC105371397 | HT_HG-U133_Plus_PM |
| 55 | 229069_PM_at | SARNP | SAP domain containing ribonucleoprotein | HT_HG-U133_Plus_PM |
| 56 | 230761_PM_at | — | zi38f01.s1 Homo sapiens cDNA, 3' end /clone = IMAGE-433081 /clone_end = 3' /gb = AA676567 /gi = 2657089 /ug = Hs.113759 /len = 407 | HT_HG-U133_Plus_PM |
| 57 | 238591_PM_at | — | qe50c03.x1 Homo sapiens cDNA, 3' end /clone = IMAGE-1742404 /clone_end = 3' /gb = AI185922 /gi = 3736560 /ug = Hs.168203 /len = 465 | HT_HG-U133_Plus_PM |
| 58 | 242241_PM_x_at | — | DB_XREF = yi33f06.s1 /CLONE = IMAGE: 141059 | HT_HG-U133_Plus_PM |
| 59 | 242728_PM_at | — | Homo sapiens cDNA FLJ42479 fis, clone BRACE2031899. | HT_HG-U133_Plus_PM |
| 60 | 32811_PM_at | MYO1C | myosin IC | HT_HG-U133_Plus_PM |
| 61 | 50314_PM_i_at | C20orf27 | chromosome 20 open reading frame 27 | HT_HG-U133_Plus_PM |

TABLE 6

Example Alternate Gene Set for use in TX versus subAR Discrimination

| # | Probeset ID | Gene Symbol | Gene Title | Array Name |
|---|---|---|---|---|
| 1 | 222064_PM_s_at | AARSD1 | alanyl-tRNA synthetase domain containing 1 | HT_HG-U133_Plus_PM |
| 2 | 200613_PM_at | AP2M1 | adaptor related protein complex 2 mu 1 subunit | HT_HG-U133_Plus_PM |
| 3 | 221657_PM_s_at | ASB6 | ankyrin repeat and SOCS box containing 6 | HT_HG-U133_Plus_PM |
| 4 | 214116_PM_at | BTD | biotinidase | HT_HG-U133_Plus_PM |
| 5 | 50314_PM_i_at | C20orf27 | chromosome 20 open reading frame 27 | HT_HG-U133_Plus_PM |
| 6 | 222165_PM_x_at | C9orf16 | chromosome 9 open reading frame 16 | HT_HG-U133_Plus_PM |

TABLE 6-continued

Example Alternate Gene Set for use in TX versus subAR Discrimination

| # | Probeset ID | Gene Symbol | Gene Title | Array Name |
|---|---|---|---|---|
| 7 | 1555730_PM_a_at | CFL1 | cofilin 1 | HT_HG-U133_Plus_PM |
| 8 | 203536_PM_s_at | CIAO1 | cytosolic iron-sulfur assembly component 1 | HT_HG-U133_Plus_PM |
| 9 | 1562460_PM_at | CNDP2 | carnosine dipeptidase 2 | HT_HG-U133_Plus_PM |
| 10 | 219805_PM_at | CXorf56 | chromosome X open reading frame 56 | HT_HG-U133_Plus_PM |
| 11 | 200041_PM_s_at | DDX39B | DExD-box helicase 39B | HT_HG-U133_Plus_PM |
| 12 | 217436_PM_x_at | HLA-J | major histocompatibility complex, class I, J (pseudogene) | HT_HG-U133_Plus_PM |
| 13 | 212431_PM_at | HMGXB3 | HMG-box containing 3 | HT_HG-U133_Plus_PM |
| 14 | 201841_PM_s_at | HSPB1 | heat shock protein family B (small) member 1 | HT_HG-U133_Plus_PM |
| 15 | 204191_PM_at | IFNAR1 | interferon alpha and beta receptor subunit 1 | HT_HG-U133_Plus_PM |
| 16 | 201234_PM_at | ILK | integrin linked kinase | HT_HG-U133_Plus_PM |
| 17 | 222471_PM_s_at | KCMF1 | potassium channel modulatory factor 1 | HT_HG-U133_Plus_PM |
| 18 | 201977_PM_s_at | KIAA0141 | KIAA0141 | HT_HG-U133_Plus_PM |
| 19 | 229035_PM_s_at | KLHDC4 | kelch domain containing 4 | HT_HG-U133_Plus_PM |
| 20 | 1558525_PM_at | LOC101928595 | uncharacterized LOC101928595 | HT_HG-U133_Plus_PM |
| 21 | 225680_PM_at | LRWD1 | leucine rich repeats and WD repeat domain containing 1 | HT_HG-U133_Plus_PM |
| 22 | 226644_PM_at | MIB2 | mindbomb E3 ubiquitin protein ligase 2 | HT_HG-U133_Plus_PM |
| 23 | 225947_PM_at | MYO19 | myosin XIX | HT_HG-U133_Plus_PM |
| 24 | 32811_PM_at | MYO1C | myosin IC | HT_HG-U133_Plus_PM |
| 25 | 203110_PM_at | PTK2B | protein tyrosine kinase 2 beta | HT_HG-U133_Plus_PM |
| 26 | 226696_PM_at | RBBP9 | RB binding protein 9, serine hydrolase | HT_HG-U133_Plus_PM |
| 27 | 209936_PM_at | RBM5 | RNA binding motif protein 5 | HT_HG-U133_Plus_PM |
| 28 | 222815_PM_at | RLIM | ring finger protein, LIM domain interacting | HT_HG-U133_Plus_PM |
| 29 | 1555916_PM_at | RPUSD3 | RNA pseudouridylate synthase domain containing 3 | HT_HG-U133_Plus_PM |
| 30 | 206949_PM_s_at | RUSC1 | RUN and SH3 domain containing 1 | HT_HG-U133_Plus_PM |
| 31 | 229069_PM_at | SARNP | SAP domain containing ribonucleoprotein | HT_HG-U133_Plus_PM |
| 32 | 221269_PM_s_at | SH3BGRL3 | SH3 domain binding glutamate rich protein like 3 | HT_HG-U133_Plus_PM |
| 33 | 223222_PM_at | SLC25A19 | solute carrier family 25 member 19 | HT_HG-U133_Plus_PM |
| 34 | 202358_PM_s_at | SNX19 | sorting nexin 19 | HT_HG-U133_Plus_PM |
| 35 | 1563641_PM_a_at | SNX20 | sorting nexin 20 | HT_HG-U133_Plus_PM |
| 36 | 219100_PM_at | STN1 | STN1, CST complex subunit | HT_HG-U133_Plus_PM |
| 37 | 218776_PM_s_at | TMEM62 | transmembrane protein 62 | HT_HG-U133_Plus_PM |
| 38 | 202009_PM_at | TWF2 | twinfilin actin binding protein 2 | HT_HG-U133_Plus_PM |
| 39 | 208997_PM_s_at | UCP2 | uncoupling protein 2 | HT_HG-U133_Plus_PM |
| 40 | 223613_PM_at | UQCR11 | ubiquinol-cytochrome c reductase, complex III subunit XI | HT_HG-U133_Plus_PM |
| 41 | 230761_PM_at* | — | *Homo sapiens* cDNA, 3' end /clone = IMAGE-433081 | HT_HG-U133_Plus_PM |

TABLE 6-continued

Example Alternate Gene Set for use in TX versus subAR Discrimination

| # | Probeset ID | Gene Symbol | Gene Title | Array Name |
|---|---|---|---|---|
| 42 | 238591_PM_at* | — | /clone_end = 3'<br>/gb = AA676567<br>/gi = 2657089<br>/ug = Hs.113759<br>/len = 407<br>Homo sapiens cDNA, 3' end<br>/clone = IMAGE-1742404<br>/clone_end = 3'<br>/gb = AI185922<br>/gi = 3736560<br>/ug = Hs.168203<br>/len = 465 | HT_HG-U133_Plus_PM |
| 43 | 242241_PM_x_at | — | gb: R66713<br>/DB_XREF = gi: 839351<br>/DB_XREF = yi33f06.s1<br>/CLONE = IMAGE: 141059<br>/FEA = EST<br>/CNT = 3<br>/TID = Hs.270927.0<br>/TIER = ConsEnd<br>/STK = 3<br>/UG = Hs.270927<br>/UG_TITLE = ESTs | HT_HG-U133_Plus_PM |

VI. Analysis of Expression Profiles and Classification of Samples

Before expression profiles can be used to classify samples according to the methods of the disclosure, data from determined expression levels may be transformed. Analysis of expression levels initially provides a measurement of the expression level of each of several individual genes. The expression level can be absolute in terms of a concentration of an expression product, or relative in terms of a relative concentration of an expression product of interest to another expression product in the sample. For example, relative expression levels of genes can be expressed with respect to the expression level of a house-keeping gene in the sample. Relative expression levels can also be determined by simultaneously analyzing differentially labeled samples hybridized to the same array. Expression levels can also be expressed in arbitrary units, for example, related to signal intensity.

The individual expression levels, whether absolute or relative, can be converted into values or other designations providing an indication of presence or risk of TX, non-TX, or subAR by comparison with one or more reference points. Preferably, genes in Tables 1, 2, 3, 4, 5, 6 and/or 8 are used for such analysis. The reference points can include a measure of an average or mean expression level of a gene in subjects having had a kidney transplant without subAR or with TX, an average or mean value of expression levels in subjects having had a kidney transplant with subAR or non-TX, and/or an average/mean value of expression levels in subjects having had a kidney transplant with acute rejection. The reference points can also include a scale of values found in kidney transplant patients including patients having and not having subAR or non-TX. The reference points can also or alternatively include a reference value in the subject before kidney transplant, or a reference value in a population of patients who have not undergone kidney transplant. Such reference points can be expressed in terms of absolute or relative concentrations of gene products as for measured values in a sample.

For comparison between a measured expression level and reference level(s), the measured level sometimes needs to be normalized for comparison with the reference level(s) or vice versa. The normalization serves to eliminate or at least minimize changes in expression level unrelated to subAR or non-TX conditions (e.g., from differences in overall health of the patient or sample preparation). Normalization can be performed by determining what factor is needed to equalize a profile of expression levels measured from different genes in a sample with expression levels of these genes in a set of reference samples from which the reference levels were determined. Commercial software is available for performing such normalizations between different sets of expression levels.

The data (e.g. expression level or expression profile) derived from the patient sample the sample may be compared to data pertaining to one or more control samples, which may be samples from the same patient at different times or samples from different patients. In some cases, the one or more control samples may comprise one or more samples from healthy subjects, unhealthy subjects, or a combination thereof. The one or more control samples may comprise one or more samples from healthy (TX) subjects, subjects suffering from nonstable renal transplant function (non-TX), or subjects suffering from subclinical acute transplant rejection (subAR), or a combination thereof. The healthy subjects may be subjects with normal transplant function. The data pertaining to the sample may be sequentially compared to two or more classes of samples. The data pertaining to the sample may be sequentially compared to three or more classes of samples. The classes of samples may comprise control samples classified as being from subjects with normal transplant function (TX), control samples classified as being from subjects suffering from nonstable renal transplant function, control samples classified as being from subjects suffering from subclinical acute transplant rejection (subAR), or a combination thereof.

Sensitivity, Specificity, Accuracy and Other Measures of Performance

The methods provided herein can help determine whether the patient either has or is at enhanced risk of subAR or non-TX with a high degree of accuracy, sensitivity, and/or specificity. In some cases, the accuracy (e.g., for detecting subAR or non-TX, for distinguishing between TX and SubAR, or distinguishing between TX and non-TX) is greater than 75%, 90%, or 95%. In some cases, the sensitivity (e.g., for detecting subAR or non-TX, for distinguishing subAR versus TX, or for distinguishing between TX and non-TX) is greater than 75%, 85%, or 90%. In some cases, the specificity (e.g., for detecting subAR or non-TX, for distinguishing between TX and SubAR, or distinguishing between TX and non-TX) is greater than 75%, 85%, 90%, or 95%. In some cases, the positive predictive value or PPV (e.g. for detecting subAR or non-TX, for distinguishing subAR versus TX, or for distinguishing between TX and non-TX) of the method is greater than 75%, 85%, 90%, or 95%. The AUC after thresholding in any of the methods provided herein may be greater than 0.9, 0.91, 0.92, 0.93, 0.94, 0.95. 0.96, 0.97, 0.98, 0.99, 0.995, or 0.999.

The methods and systems for use in identifying, classifying or characterizing a sample (e.g., for detecting subAR or non-TX, for distinguishing subAR versus TX, or for distinguishing between TX and non-TX) described herein may be characterized by having a specificity of at least about 50%, 55%, 57%, 60%, 62%, 65%, 67%, 70%, 72%, 75%, 77%, 80%, 82%, 85%, 87%, 90%, 92%, 95%, or 97%.

The methods and systems for use in identifying, classifying or characterizing a sample (e.g., for detecting subAR or non-TX, for distinguishing subAR versus TX, or for distinguishing between TX and non-TX) described herein may be characterized by having a sensitivity of at least about 50%, 55%, 57%, 60%, 62%, 65%, 67%, 70%, 72%, 75%, 77%, 80%, 82%, 85%, 87%, 90%, 92%, 95%, or 97%.

The methods and systems for use in identifying, classifying or characterizing a sample (e.g., for detecting subAR or non-TX, for distinguishing subAR versus TX, or for distinguishing between TX and non-TX) may be characterized by having a negative predictive value (NPV) greater than or equal to 90%. The NPV may be at least about 60%, 65%, 70%, 75%, 80%, 85%, 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 100%. The NPV may be at least about 95%. The NPV may be at least about 60%. The NPV may be at least about 70%. The NPV may be at least about 80%.

The methods and/or systems disclosed herein for use in identifying, classifying or characterizing a sample (e.g., for detecting subAR or non-TX, for distinguishing subAR versus TX, or for distinguishing between TX and non-TX) may be characterized by having a positive predictive value (PPV) of at least about 30%. The PPV may be at least about 32%, 35%, 40%, 45%, 50%, 55%, 60%, 65%, 70%, 75%, 80%, 85%, 90%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 100%. The PPV may be greater than or equal to 95%. The PPV may be greater than or equal to 96%. The PPV may be greater than or equal to 97%. The PPV may be greater than or equal to 98%.

Classifiers

The methods include using a trained classifier or algorithm to analyze sample data, particularly to detect subAR or non-TX conditions. For example, a sample can be classified as, or predicted to be: a) TX, b) non-TX, and/or c) subAR. Many statistical classification techniques are known to those of skill in the art. In supervised learning approaches, a group of samples from two or more groups (e.g. TX and subAR) are analyzed with a statistical classification method. Differential gene expression data can be discovered that can be used to build a classifier that differentiates between the two or more groups. A new sample can then be analyzed so that the classifier can associate the new sample with one of the two or more groups. Commonly used supervised classifiers include without limitation the neural network (multi-layer perceptron), support vector machines, k-nearest neighbours, Gaussian mixture model, Gaussian, naive Bayes, decision tree and radial basis function (RBF) classifiers. Linear classification methods include Fisher's linear discriminant, LDA, logistic regression, naive Bayes classifier, perceptron, and support vector machines (SVMs). Other classifiers for use with the invention include quadratic classifiers, k-nearest neighbor, boosting, decision trees, random forests, neural networks, pattern recognition, Elastic Net, Golub Classifier, Parzen-window, Iterative RELIEF, Classification Tree, Maximum Likelihood Classifier, Nearest Centroid, Prediction Analysis of Microarrays (PAM), Fuzzy C-Means Clustering, Bayesian networks and Hidden Markov models. One of skill will appreciate that these or other classifiers, including improvements of any of these, are contemplated within the scope of the invention, as well as combinations of any of the foregoing.

Classification using supervised methods is generally performed by the following methodology:

In order to solve a given problem of supervised learning (e.g. learning to recognize handwriting) one has to consider various steps:

1. Gather a training set. These can include, for example, samples that are from TX patients, samples that are from non-TX patients, and/or samples that are from subAR patients. The training samples are used to "train" the classifier.
2. Determine the input "feature" representation of the learned function. The accuracy of the learned function depends on how the input object is represented. Typically, the input object is transformed into a feature vector, which contains a number of features that are descriptive of the object. The number of features should not be too large, because of the curse of dimensionality; but should be large enough to accurately predict the output.
3. Determine the structure of the learned function and corresponding learning algorithm. A learning algorithm is chosen, e.g., artificial neural networks, decision trees, Bayes classifiers or support vector machines. The learning algorithm is used to build the classifier.
4. Build the classifier (e.g. classification model). The learning algorithm is run on the gathered training set. Parameters of the learning algorithm may be adjusted by optimizing performance on a subset (called a validation set) of the training set, or via cross-validation. After parameter adjustment and learning, the performance of the algorithm may be measured on a test set of naive samples that is separate from the training set.

Once the classifier (e.g. classification model) is determined as described above, it can be used to classify a sample, e.g., that of a kidney transplant recipient analyzed by the methods of the invention. In some instances, gene expression levels are measured in a sample from a transplant recipient (or a healthy or transplant excellent control) and a classifier/classification model or algorithm (e.g., trained algorithm) is applied to the resulting data in order to detect, predict, monitor, or estimate the risk of a transplant condition (e.g., subAR, non-TX)

Training of multi-dimensional classifiers (e.g., algorithms) may be performed using numerous samples. For example, training of the multi-dimensional classifier may be performed using at least about 10, 20, 30, 40, 50, 60, 70, 80, 90, 100, 110, 120, 130, 140, 150, 160, 170, 180, 190, 200 or more samples. In some cases, training of the multi-dimensional classifier may be performed using at least about 200, 210, 220, 230, 240, 250, 260, 270, 280, 290, 300, 350, 400, 450, 500 or more samples. In some cases, training of the multi-dimensional classifier may be performed using at least about 525, 550, 600, 650, 700, 750, 800, 850, 900, 950, 1000, 1100, 1200, 1300, 1400, 1500, 1600, 1700, 1800, 2000 or more samples.

Further disclosed herein are classifier sets and methods of producing one or more classifier sets (e.g. limited sets of genes used to generate a classification model). The classifier set may comprise one or more genes, particularly genes from Tables 1, 2, 3, 4, 5, 6 and/or 8. In some cases, the classifier set may comprise 1, 2, 3, 4, 5, 6, 7, 8, 9, 10, 11, 12, 13, 14, 15, 16, 17, 18, 19, 20, 50, 60, 70, 80, 90, 100, 110, 120, 130, 140, 150, 160, 170, 180, 190, 200, 210, or more genes from Tables 1, 2, 3, 4, 5, 6 and/or 8. Disclosed herein is the use of a classification system comprising one or more classifiers. In some instances, the classifier is a 2-, 3-, 4-, 5-, 6-, 7-, 8-, 9-, or 10-way classifier. In some preferred embodiments, the classifier is a two-way classifier. In some embodiments, the classifier is a three-way classifier.

A two-way classifier may classify a sample from a subject into one of two classes. In some instances, a two-way classifier may classify a sample from an organ transplant recipient into one of two classes comprising subAR and normal transplant function (TX). In some instances, a two-way classifier may classify a sample from an organ transplant recipient into one of two classes comprising non-TX and TX (normal transplant function).

A three way classifier may classify a sample from a subject into one of three classes. A three-way classifier may classify a sample from an organ transplant recipient into one of three classes comprising AR, subAR, and TX. In some cases, the classifier may work by applying two or more classifiers sequentially. For example, the first classifier may classify AR+subAR and TX, which results in a set of samples that are classified either as (1) TX or (2) AR or subAR. In some cases, a second classifier capable of distinguishing between AR and subAR is applied to the samples classified as having AR or subAR in order to detect the subAR samples.

Classifiers and/or classifier probe sets may be used to either rule-in or rule-out a sample as healthy. For example, a classifier may be used to classify a sample as being from a healthy subject. Alternatively, a classifier may be used to classify a sample as being from an unhealthy subject. Alternatively, or additionally, classifiers may be used to either rule-in or rule-out a sample as transplant rejection. For example, a classifier may be used to classify a sample as being from a subject suffering from a transplant rejection. In another example, a classifier may be used to classify a sample as being from a subject that is not suffering from a transplant rejection. Classifiers may be used to either rule-in or rule-out a sample as subclinical acute rejection. Classifiers may be used to either rule-in or rule-out a sample as non-TX.

Unsupervised learning approaches can also be used with the invention. Clustering is an unsupervised learning approach wherein a clustering algorithm correlates a series of samples without the use the labels. The most similar samples are sorted into "clusters." A new sample could be sorted into a cluster and thereby classified with other members that it most closely associates.

Computer Implemented Methods

Expression levels can be analyzed and associated with status of a subject (e.g., presence or susceptibility to subAR or non-TX) in a digital computer. As shown in FIG. 1, a sample (110) is first collected from a subject (for example, from a transplant recipient). The sample is assayed (120) and gene expression products are generated. A computer system (130) is used in analyzing the data and making a classification (140) based on the results of the results. Optionally, such a computer is directly linked to a scanner or the like receiving experimentally determined signals related to expression levels. Alternatively, expression levels can be input by other means. The computer can be programmed to convert raw signals into expression levels (absolute or relative), compare measured expression levels with one or more reference expression levels, or a scale of such values, as described above. The computer can also be programmed to assign values or other designations to expression levels based on the comparison with one or more reference expression levels, and to aggregate such values or designations for multiple genes in an expression profile. The computer can also be programmed to output a value or other designation providing an indication of presence or susceptibility to subAR or non-TX as well as any of the raw or intermediate data used in determining such a value or designation.

A typical computer (see e.g. U.S. Pat. No. 6,785,613 FIGS. 4 and 5) includes a bus which interconnects major subsystems such as a central processor, a system memory, an input/output controller, an external device such as a printer via a parallel port, a display screen via a display adapter, a serial port, a keyboard, a fixed disk drive and a floppy disk drive operative to receive a floppy disk. Many other devices can be connected such as a scanner via I/O controller, a mouse connected to serial port or a network interface. The computer contains computer readable media holding codes to allow the computer to perform a variety of functions. These functions include controlling automated apparatus, receiving input and delivering output as described above. The automated apparatus can include a robotic arm for delivering reagents for determining expression levels, as well as small vessels, e.g., microtiter wells for performing the expression analysis.

Figure 2:
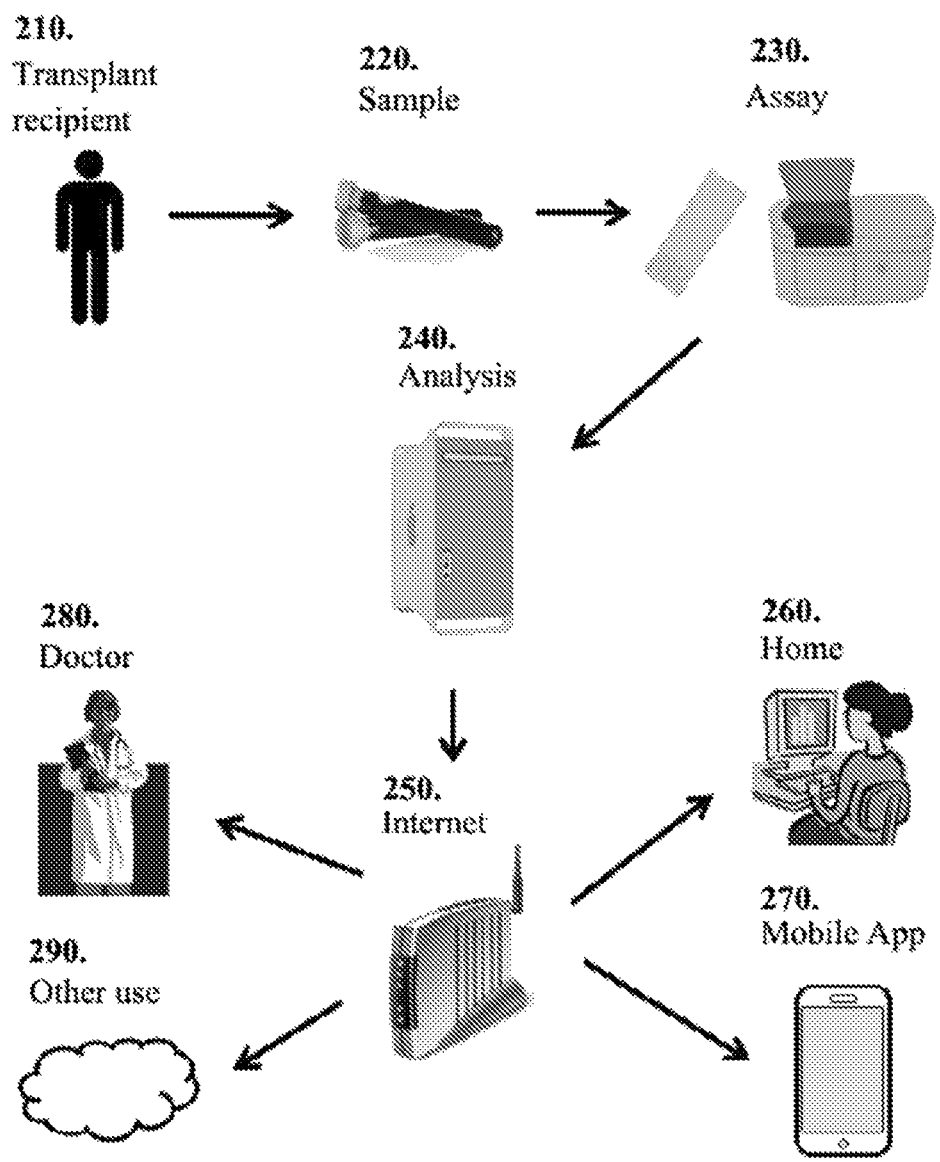
FIG. 2 is a flowchart illustrating a system for implementing transplant diagnostic methods according to disclosure and delivering the results to various parties.

The methods, systems, kits and compositions provided herein may also be capable of generating and transmitting results through a computer network. As shown in FIG. 2, a sample 220 is first collected from a subject (e.g. transplant recipient, 210). The sample is assayed 230 and gene expression products are generated. A computer system 240 is used in analyzing the data and making classification of the sample. The result is capable of being transmitted to different types of end users via a computer network 250. In some instances, the subject (e.g. patient) may be able to access the result by using a standalone software and/or a web-based application on a local computer capable of accessing the internet 260. In some instances, the result can be accessed via a mobile application 270 provided to a mobile digital processing device (e.g. mobile phone, tablet, etc.). In some instances, the result may be accessed by physicians and help them identify and track conditions of their patients 280. In some instances, the result may be used for other purposes 290 such as education and research.

Computer Program

The methods, kits, and systems disclosed herein may include at least one computer program, or use of the same. A computer program may include a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. The computer program will normally provide a sequence of instructions from one location or a plurality of locations. In various embodiments, a computer program includes, in part or in whole, one or more web applications, one or more mobile applications, one or more standalone applications, one or more web browser plug-ins, extensions, add-ins, or add-ons, or combinations thereof.

Further disclosed herein are systems for classifying one or more samples and uses thereof. The system may comprise (a) a digital processing device comprising an operating system configured to perform executable instructions and a memory device; (b) a computer program including instructions executable by the digital processing device to classify a sample from a subject comprising: (i) a first software module configured to receive a gene expression profile of one or more genes from the sample from the subject (e.g. any of the genes from Tables 1, 2, 3, 4, 5, 6 and/or 8); (ii) a second software module configured to analyze the gene expression profile from the subject; and (iii) a third software module configured to classify the sample from the subject based on a classification system comprising two or more classes (e.g. TX vs non-TX, TX vs SubAR, TX vs SubAR vs AR). At least one of the classes may be selected from TX, non-TX, subAR, and AR. At least two of the classes may be selected from TX, non-TX, subAR, and AR. Three of the classes may be selected from TX, non-TX, subAR, and AR. Analyzing the gene expression profile from the subject may comprise applying an algorithm. Analyzing the gene expression profile may comprise normalizing the gene expression profile from the subject. In some instances, normalizing the gene expression profile does not comprise quantile normalization.

Figure 4:
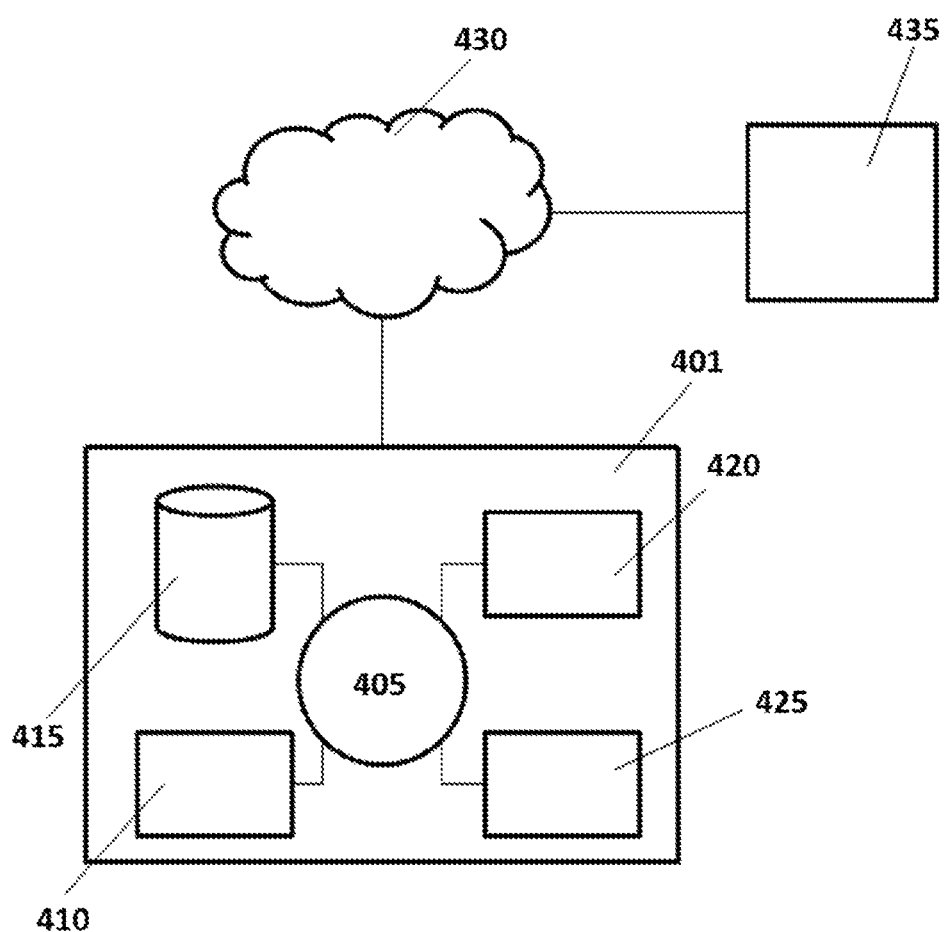
FIG. 4 is a chart illustrating a computer system suitable for implementing the transplant diagnostic methods according to the disclosure.

FIG. 4 shows a computer system (also "system" herein) 201 programmed or otherwise configured for implementing the methods of the disclosure, such as producing a selector set and/or for data analysis. The system 401 includes a central processing unit (CPU, also "processor" and "computer processor" herein) 405, which can be a single core or multi core processor, or a plurality of processors for parallel processing. The system 401 also includes memory 410 (e.g., random-access memory, read-only memory, flash memory), electronic storage unit 415 (e.g., hard disk), communications interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communications bus (solid lines), such as a motherboard. The storage unit 415 can be a data storage unit (or data repository) for storing data. The system 401 is operatively coupled to a computer network ("network") 430 with the aid of the communications interface 420. The network 430 can be the Internet, an internet and/or extranet, or an intranet and/or extranet that is in communication with the Internet. The network 430 in some instances is a telecommunication and/or data network. The network 430 can include one or more computer servers, which can enable distributed computing, such as cloud computing. The network 430 in some instances, with the aid of the system 401, can implement a peer-to-peer network, which may enable devices coupled to the system 401 to behave as a client or a server.

The system 401 is in communication with a processing system 435. The processing system 435 can be configured to implement the methods disclosed herein. In some examples, the processing system 435 is a microarray scanner. In some examples, the processing system 435 is a real-time PCR machine. In some examples, the processing system 435 is a nucleic acid sequencing system, such as, for example, a next generation sequencing system (e.g., Illumina sequencer, Ion Torrent sequencer, Pacific Biosciences sequencer). The processing system 435 can be in communication with the system 401 through the network 430, or by direct (e.g., wired, wireless) connection. The processing system 435 can be configured for analysis, such as nucleic acid sequence analysis.

Methods as described herein can be implemented by way of machine (or computer processor) executable code (or software) stored on an electronic storage location of the system 401, such as, for example, on the memory 410 or electronic storage unit 415. During use, the code can be executed by the processor 405. In some examples, the code can be retrieved from the storage unit 415 and stored on the memory 410 for ready access by the processor 405. In some situations, the electronic storage unit 415 can be precluded, and machine-executable instructions are stored on memory 410.

Digital Processing Device

The methods, kits, and systems disclosed herein may include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

The digital processing device will normally include an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

The device generally includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

A display to send visual information to a user will normally be initialized. Examples of displays include a cathode ray tube (CRT, a liquid crystal display (LCD), a thin film transistor liquid crystal display (TFT-LCD, an organic light emitting diode (OLED) display. In various further embodiments, on OLED display is a passive-matrix OLED (PMOLED) or active-matrix OLED (AMOLED) display. In some embodiments, the display may be a plasma display, a video projector or a combination of devices such as those disclosed herein.

The digital processing device may include an input device to receive information from a user. The input device may be, for example, a keyboard, a pointing device including, by way of non-limiting examples, a mouse, trackball, track pad, joystick, game controller, or stylus; a touch screen, or a multi-touch screen, a microphone to capture voice or other sound input, a video camera to capture motion or visual input or a combination of devices such as those disclosed herein.

Non-Transitory Computer Readable Storage Medium

The methods, kits, and systems disclosed herein may include one or more non-transitory computer readable storage media encoded with a program including instructions executable by the operating system to perform and analyze the test described herein; preferably connected to a networked digital processing device. The computer readable storage medium is a tangible component of a digital that is optionally removable from the digital processing device. The computer readable storage medium includes, by way of non-limiting examples, CD-ROMs, DVDs, flash memory devices, solid state memory, magnetic disk drives, magnetic tape drives, optical disk drives, cloud computing systems and services, and the like. In some instances, the program and instructions are permanently, substantially permanently, semi-permanently, or non-transitorily encoded on the media.

A non-transitory computer-readable storage media may be encoded with a computer program including instructions executable by a processor to create or use a classification system. The storage media may comprise (a) a database, in a computer memory, of one or more clinical features of two or more control samples, wherein (i) the two or more control samples may be from two or more subjects; and (ii) the two or more control samples may be differentially classified based on a classification system comprising two or more classes; (b) a first software module configured to compare the one or more clinical features of the two or more control samples; and (c) a second software module configured to produce a classifier set based on the comparison of the one or more clinical features.

At least two of the classes may be selected from TX, non-TX, SubAR, and AR. Three of the classes may be selected from TX, non-TX, SubAR, and AR. The storage media may further comprise one or more additional software modules configured to classify a sample from a subject. Classifying the sample from the subject may comprise a classification system comprising two or more classes.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™ JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS© Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The methods, kits, and systems disclosed herein may include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

The methods, kits, and systems disclosed herein may comprise one or more databases, or use of the same. In view of the disclosure provided herein, those of skill in the art will recognize that many databases are suitable for storage and retrieval of information pertaining to gene expression profiles, sequencing data, classifiers, classification systems, therapeutic regimens, or a combination thereof. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Data Transmission

The methods, kits, and systems disclosed herein may be used to transmit one or more reports. The one or more reports may comprise information pertaining to the classification and/or identification of one or more samples from one or more subjects. The one or more reports may comprise information pertaining to a status or outcome of a transplant in a subject. The one or more reports may comprise information pertaining to therapeutic regimens for use in treating transplant rejection in a subject in need thereof. The one or more reports may comprise information pertaining to therapeutic regimens for use in treating transplant dysfunction in a subject in need thereof. The one or more reports may comprise information pertaining to therapeutic regimens for use in suppressing an immune response in a subject in need thereof.

The one or more reports may be transmitted to a subject or a medical representative of the subject. The medical representative of the subject may be a physician, physician's assistant, nurse, or other medical personnel. The medical representative of the subject may be a family member of the subject. A family member of the subject may be a parent, guardian, child, sibling, aunt, uncle, cousin, or spouse. The medical representative of the subject may be a legal representative of the subject.

VII. Guiding a Therapeutic Decision

In some instances, the methods, compositions, systems and kits described herein provide information to a medical practitioner that can be useful in making a therapeutic decision. Therapeutic decisions may include decisions to: continue with a particular therapy, modify a particular therapy, alter the dosage of a particular therapy, stop or terminate a particular therapy, altering the frequency of a therapy, introduce a new therapy, introduce a new therapy to be used in combination with a current therapy, or any combination of the above. In some instances, the results of diagnosing, predicting, or monitoring a condition of a transplant recipient may be useful for informing a therapeutic decision such as removal of the transplant. In some instances, the removal of the transplant can be an immediate removal. In other instances, the therapeutic decision can be a retransplant. Other examples of therapeutic regimen can include a blood transfusion in instances where the transplant recipient is refractory to immunosuppressive or antibody therapy.

If a patient is indicated as having or being at enhanced risk of AR, subAR, or non-TX, the physician can subject the patient to additional testing including performing a kidney biopsy or performing other analyses such as creatinine, BUN, or glomerular filtration rate at increased frequency. Additionally or alternatively, the physician can change the treatment regime being administered to the patient. A change in treatment regime can include administering an additional or different drug to a patient, or administering a higher dosage or frequency of a drug already being administered to the patient.

Many different drugs are available for treating rejection, such as immunosuppressive drugs used to treat transplant rejection calcineurin inhibitors (e.g., cyclosporine, tacrolimus), mTOR inhibitors (e.g., sirolimus and everolimus), anti-proliferatives (e.g., azathioprine, mycophenolic acid, mycophenolate mofetil or MMF), corticosteroids (e.g., prednisolone and hydrocortisone), antibodies (e.g., basiliximab, daclizumab, Orthoclone, alemtuzumab, anti-thymocyte globulin and anti-lymphocyte globulin), and biologics (e.g. belatacept).

Alternatively, if the patient is not indicated as having or being at enhanced risk of AR, subAR, or non-TX, the patient's regimen may be managed in such a way that avoids unneccessary treatment of AR, subAR, or transplant dysfunction conditions. For instance, when subAR or AR is not detected, suitable management may include refraining from biopsy procedures or immunosuppressant regimen adjustments for a specific period of time, such as e.g. 1 week, 2 weeks, 3 weeks, 4 weeks, 2 months, 3 months, 4 months, 5 months, or 6 months. In some cases, when subAR is not detected and the patient has previously received an increase in dose of a particular immunosuppressant of their regimen within a particular period of time (e.g. 1 week, 2 weeks, 3 weeks, 4 weeks, 2 months, 3 months, 4 months, 5 months, or 6 months), or has received administration of a new immunosuppressant within a particular period of time (e.g. 1 week, 2 weeks, 3 weeks, 4 weeks, 2 months, 3 months, 4 months, 5 months, or 6 months), the current increase in dose or immunosuppressant administration may be maintained (e.g. 1 week, 2 weeks, 3 weeks, 4 weeks, 2 months, 3 months, 4 months, 5 months, 6 months, 1 year, 1.5 years, 2 years, 3 years, 4 years, 5 years, or indefinitely).

As used herein, the term "stable" when used to refer to renal function in a subject refers to a serum creatinine level less than 2.3 mg/dl and a less than 20% increase in creatinine compared to a minimum of 2-3 prior values over a mean period and range of 132 and 75-187 days, respectively.

As used herein, the term "normal" when used to refer to renal allograft status in a subject refers to normal histology on a surveillance biopsy (e.g. no evidence of rejection—Banff i=0 and t=0, g=0, ptc=0; ci=0 or 1 and ct=0 or 1) and stable renal function.

As used herein, the term "normal" when used to refer to creatinine levels in a subject refers to a serum creatinine level of less than 2.3 mg/dl.

The terms "immunosuppressant drug regimen" or "immunosuppressant treatment regimen", as used herein, refers to a set of at least one drug with immunosuppressant activity which is administered to a patient on an ongoing basis to treat or prevent allograft rejection. Immunosuppressant drug regimens may include, but are not limited to, an "induction" regimen (which is administered to a patient immediately before and optionally immediately after transplantation, see e.g. Kasiske et al. Am J Transplant. 2009 November; 9 Suppl 3:S1-155), an initial maintenance regimen, a long-term maintenance regimen, a breakout regimen, or a combination thereof.

With respect to immunosuppression therapy of kidney transplant recipients, the 2009 Kidney Disease: Improving Global Outcomes (KDIGO) guidelines (see e.g. Kasiske et al. Am J Transplant. 2009 November; 9 Suppl 3:S1-155, which is incorporated by reference herein) outline an example immunosuppression regimen for a kidney transplant recipient. Prior to transplant, a patient receives an "induction" combination of immunosuppressants, ideally comprising a biologic agent such as an IL-2 receptor antagonist (e.g. basiliximab or daclizumab) or a lymphocyte-depleting agent (e.g. antithymocyte globulin, antilymphocyte globulin, alemtuzumab, and/or monomurab-CD3), which may be continued immediately after transplantation. The use of a lymphocyte-depleting agent may be recommended for patients considered at high risk of immune-mediated rejection. Calcineurin inhibitors (CNIs, e.g. tacrolimus) may be additionally used in the "induction" phase. After transplant, a patient may be treated with an initial maintenance immunosuppression regimen which ideally comprises a calcineurin inhibitor (e.g. tacrolimus) or an mTOR inhibitor (e.g. sirolimus) and an antiproliferative agent (e.g. mycophenolate mofetil or MMF). The initial maintenance regimen may optionally additionally comprise a corticosteroid. Within 2-4 months after transplantation with no acute rejection, the immunosuppression regimen may be adjusted to a long-term maintenance phase, where the lowest planned doses of immunosuppressants are used, calcineurin inhibitor therapy is continued (if originally used), and corticosteroid therapy is continued (if used beyond the first week of transplant).

An additional immunosuppressant regimen to note is a "breakout" regimen used for treatment of any rejection episodes that occur after organ transplant. This may be a permanent adjustment to the maintenance regimen or temporary drug therapy used to minimize damage during the acute rejection episode. The adjustment may comprise temporary or long-term addition of a corticosteroid, temporary use of lymphocyte-depleting agents, and long-term addition of antiproliferative agents (e.g. mycophenolate mofetil/MMF or azathioprine, for patients not already receiving it), and any combination thereof. Treatment may also comprise plasma exchange, intravenous immunoglobulin, and anti-CD-20 antibody therapy, and any combination thereof.

The methods and systems used in this disclosure may guide the decision points in these treatment regimens (e.g. addition of agents to the immunosuppression regimen due to increased evaluation of risk). For example, they may allow the evaluation of a patient with low time-of-transplant risk factors (e.g. high HLA matching between recipient and donor organ) as having subAR or AR, justifying the adjustment of an immunosuppression regimen as described above.

Conversely, if the patient is indicated as having low risk of AR or subAR, or is identified as TX, the physician need not order further diagnostic procedures, particularly not invasive ones such as biopsy. Further, the physician can continue an existing treatment regime, or even decrease the dose or frequency of an administered drug.

In some methods, expression levels are determined at intervals in a particular patient (i.e., monitoring). Preferably, the monitoring is conducted by serial minimally-invasive tests such as blood draws; but, in some cases, the monitoring may also involve analyzing a kidney biopsy, either histologically or by analyzing a molecular profile. The monitoring may occur at different intervals, for example the monitoring may be hourly, daily, weekly, monthly, yearly, or some other time period, such as twice a month, three times a month, every two months, every three months, every 4 months, every 5 months, every 6 months, every 7 months, every 8 months, every 9 months, every 10 months, every 11 months, or every 12 months.

Such methods can provide a series of values changing over time indicating whether the aggregate expression levels in a particular patient are more like the expression levels in patients undergoing subAR or not undergoing subAR, or having a TX condition kidney or a non-TX condition kidney. Movement in value toward or away from subAR or non-TX can provide an indication whether an existing immunosuppressive regimen is working, whether the immunosuppressive regimen should be changed (e.g. via administration of a new immunosuppressant to the transplant recipient or increase in dose of an immunosuppressant currently being administered to the transplant recipient) or whether a biopsy or increased monitoring by markers such as creatinine or glomerular filtration rate should be performed. In some cases, consecutive (e.g. at least two) tests positive for subAR or non-TX as described herein indicate that an additional action be taken, e.g. adjustment of the immunosuppressive regimen (e.g. via administration of a new immunosuppressant to the transplant recipient or increase in dose of an immunosuppressant currently being administered to the transplant recipient), collection and evaluation of a kidney biopsy, or administration of a serum creatinine and/or eGFR test. In some cases, consecutive (e.g. at least two, three, four, five, six, seven, eight, nine, ten) tests ambiguous for subAR or non-TX as described herein indicate that an additional confirmatory action be taken, e.g. collection and evaluation of a kidney biopsy or administration of a serum creatinine and/or eGFR test. The consecutive (e.g. at least two, three, four, five, six, seven, eight, nine, ten) tests may be separated by an appropriate time period (e.g. one day, one week, two weeks, three weeks, one month, two months, three months, four months, five months, six months, or one year) to ensure that the tests accurately represent a trend.

The methods provided herein include administering a blood test (e.g., a test to detect subclinical acute rejection) to a transplant recipient who has already undergone a surveillance or protocol biopsy of the kidney and received a biopsy result in the form of a histological analysis or a molecular profiling analysis. In some particular instances, the analysis of the kidney biopsy (e.g., by histology or molecular profiling) may result in ambiguous, inconclusive or borderline results. In such cases, a blood test provided herein may assist a caregiver with determining whether the transplant recipient has subclinical acute rejection or with interpreting the biopsy. In other cases the biopsy itself may be inconclusive or ambiguous, and in such cases the molecular analysis of the biopsy may be used in adjunct with the histology to confirm a diagnosis. In some instances, the analysis of the kidney biopsy may yield a negative result. In such cases, the subject may receive a blood test provided herein in order to confirm the negative result, or to detect subclinical acute rejection. In some cases, after receiving any type of biopsy result (e.g., negative result, ambiguous, inconclusive, borderline, positive), the patient may receive multiple, serial blood tests to monitor changes in molecular markers correlated with subclinical acute rejection.

Figure 3:
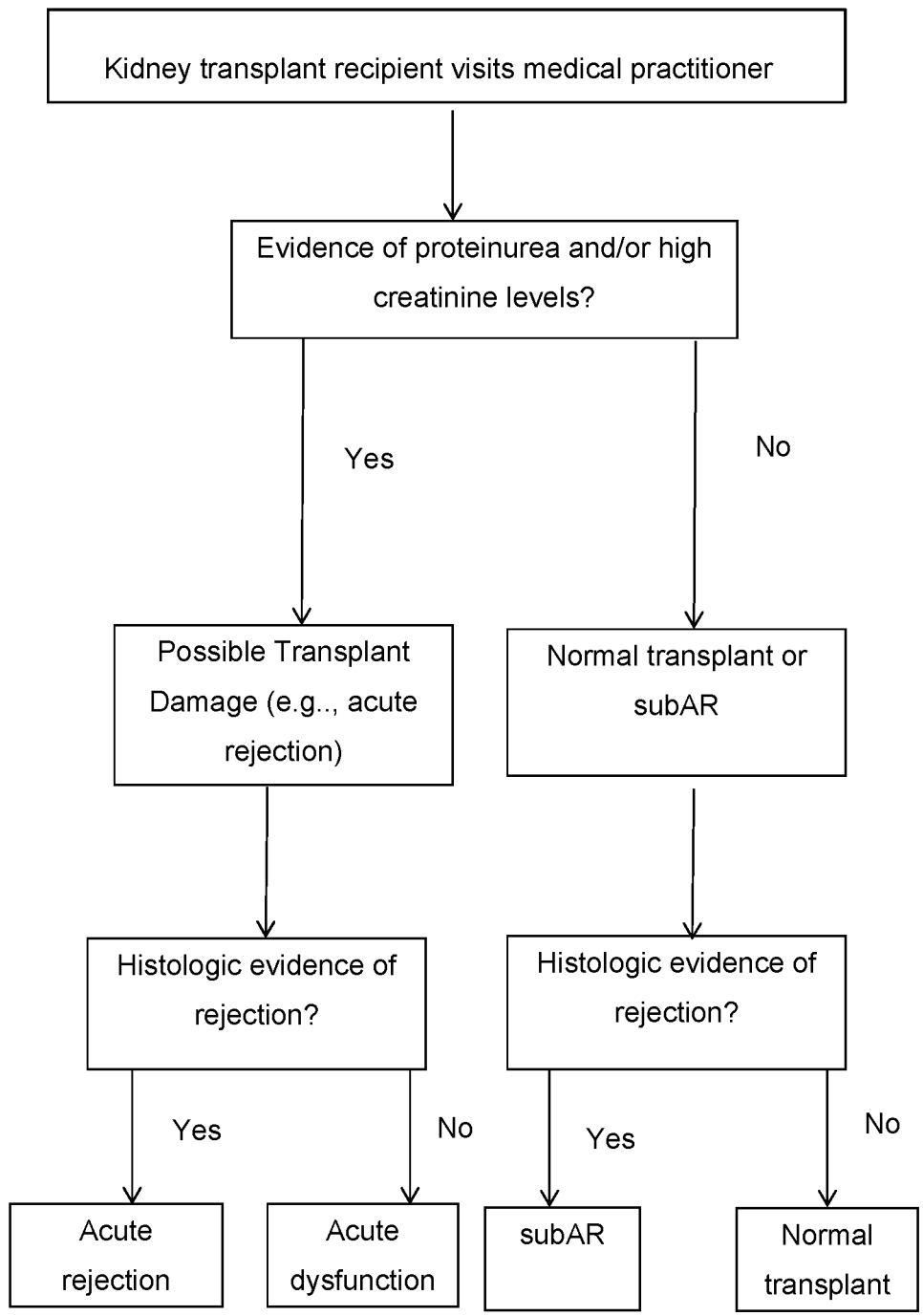
FIG. 3 is a flowchart illustrating the relationship between different transplant conditions in terms of symptoms observed by medical practitioners.

The methods provided herein also include administering a biopsy test (e.g., histology or molecular profiling) to a transplant recipient who has received a molecular blood profiling test. For example, the transplant recipient may receive an ambiguous, inconclusive or borderline result on a blood molecular profiling test. In such cases, the patient's healthcare worker may use the results of a kidney biopsy test as a complement to the blood test to determine whether the subject is experiencing subclinical acute rejection. In another example, the transplant recipient may have received a positive result on a blood molecular profiling test, indicating that the transplant recipient has, or likely has, subclinical acute rejection, or even multiple positive results over time. In such cases, the patient's physician or other healthcare worker may decide to biopsy the patient's kidney in order to detect subAR. Such kidney biopsy test may be a molecular profiling analysis of the patient's kidney, as described herein. In some cases, a histological analysis of the kidney biopsy may be performed instead of, or in addition to, the molecular analysis of the biopsy. As shown in FIG. 3, a subject (such as a kidney transplant recipient) visits a medical practitioner. The medical practitioner determines whether there is evidence of proteinuria (e.g. >1.0 g/24 h) and/or high creatinine levels (e.g. serum creatinine levels above 1.0 mg/dL). If there is evidence of proteinuria and/or high creatinine levels, then there may be possible transplant damage (e.g. acute rejection). If there is no evidence of proteinuria and/or high creatinine levels, then it is a normal transplant or subAR. Histological evidence of rejection can be obtained in either case. If there is histological evidence of rejection following possible transplant damage, then it is acute rejection. If there is not histological evidence of rejection following possible transplant damage, then it is acute dysfunction. If there is histological evidence of rejection following normal transplant or subAR, then it is subAR. If there is not histological evidence of rejection following normal transplant or subAR, then it is a normal transplant. In some cases, the physician may decide to wait a certain period of time after receiving the positive blood result to perform the biopsy test.

The methods provided herein may often provide early detection of subAR and may help a patient to obtain early treatment such as receiving immunosuppressive therapy or increasing an existing immunosuppressive regimen. Such early treatment may enable the patient to avoid more serious consequences associated with acute rejection later in time, such as allograft loss or procedures such as kidney dialysis. In some cases, such early treatments may be administered after the patient receives both a molecular profiling blood test and a biopsy analyzed either by molecular profiling or histologically.

The diagnosis or detection of condition of a transplant recipient may be particularly useful in limiting the number of invasive diagnostic interventions that are administered to the patient. For example, the methods provided herein may limit or eliminate the need for a transplant recipient (e.g., kidney transplant recipient) to receive a biopsy (e.g., kidney biopsies) or to receive multiple biopsies. In a further embodiment, the methods provided herein can be used alone or in combination with other standard diagnosis methods currently used to detect or diagnose a condition of a transplant recipient, such as but not limited to results of biopsy analysis for kidney allograft rejection, results of histopathology of the biopsy sample, serum creatinine level, creatinine clearance, ultrasound, radiological imaging results for the kidney, urinalysis results, elevated levels of inflammatory molecules such as neopterin, and lymphokines, elevated plasma interleukin (IL)-1 in azathioprine-treated patients, elevated IL-2 in cyclosporine-treated patients, elevated IL-6 in serum and urine, intrarenal expression of cytotoxic molecules (granzyme B and perforin) and immunoregulatory cytokines (IL-2, -4, -10, interferon gamma and transforming growth factor-b1).

The methods herein may be used in conjunction with kidney function tests, such as complete blood count (CBC), serum electrolytes tests (including sodium, potassium, chloride, bicarbonate, calcium, and phosphorus), blood urea test, blood nitrogen test, serum creatinine test, urine electrolytes tests, urine creatinine test, urine protein test, urine fractional excretion of sodium (FENA) test, glomerular filtration rate (GFR) test. Kidney function may also be assessed by a renal biopsy. Kidney function may also be assessed by one or more gene expression tests.

EXAMPLES

Example 1. Detection of subAR in a Kidney Transplant Recipient Under Treatment with Immunosuppressants Post-induction kidney transplant recipients with stable allograft function on a maintenance immunosuppressant regimen (e.g. calcineurin inhibitor or mTOR inhibitor plus mycophenolate mofetil) are surveilled with peripheral blood draws on a defined schedule (e.g. 1 draw per 1-3 months). Gene expression analysis blood samples by microarray platform is performed as described herein above (e.g. using the HT_HG-U133_Plus_PM microarray).

A classifier to detect subAR is composed of differentially-expressed genes between TX and subAR (using e.g. at least 5 genes from Tables 5, 6, or 8, or at least 5 genes contacted by probes from Tables 5, 6, or 8). The classifier is applied to the microarray gene expression data above to identify a patient sample as having subAR or lack of subAR (e.g. transplant normal status, TX).

Patients identified as having subAR receive an adjustment to their immunosuppression regimen such as a temporary or long-term addition of a corticosteroid, temporary use of lymphocyte-depleting agents, plasma exchange, intravenous immunoglobulin, anti-CD-20 antibody therapy, or long-term addition of antiproliferative agents (e.g. mycophenolate mofetil or azathioprine, for patients not already receiving it). Alternatively, patients undergo a confirmatory biopsy. In contrast, patients with TX would continue monitoring as per transplant center protocol without the need for a biopsy.

Example 2. Detection of Non-TX Condition of a Transplanted Kidney Under Immunosuppressant Treatment Post-induction kidney transplant recipients with stable allograft function on a maintenance immunosuppressant regimen (e.g. calcineurin inhibitor or mTOR inhibitor plus mycophenolate mofetil) are surveilled with peripheral blood draws on a defined schedule (e.g. 1 draw per 1-3 months). Gene expression analysis of blood samples by microarray platform is performed as described herein above (e.g. using the HT_HG-U133_Plus_PM microarray).

A classifier to detect non-TX is composed of differentially-expressed genes between TX and non-TX (e.g. comprising a classifier gene set comprising 5 or more of the genes from Tables 1, 2, 3, or 4 or at least 5 genes contacted by probes from Tables 1, 2, 3, or 4). The classifier is applied to the microarray gene expression data above to identify a patient sample as having a non-TX organ.

Patients detected as having a non-TX organ are subjected to follow-up testing including serum creatinine, blood urea nitrogen, Glomerular Filtration Rate, and/or a kidney biopsy followed by histopathological analysis for organ rejection. Non-TX patients may include patients with kidney injury, acute dysfunction with no rejection, subAR, or acute rejection. Patients with impaired measures of kidney filtration and no signs of immune rejection via biopsy may have kidney injury or acute dysfunction with no rejection. Patients with impaired measures of kidney filtration and signs of immune rejection via biopsy have acute rejection. Patients without impaired measures of kidney filtration and signs of immune rejection via biopsy have subAR. In contrast, patients with TX would continue to be monitored/treated as per transplant center protocol without the need for a biopsy.

Example 3. subAR vs TX Test Classification in Kidney Transplant Patient with subAR A blood sample is taken from a kidney transplant patient with subclinical acute rejection. Serum creatinine levels of the kidney transplant patient are normal or stable. Gene expression analysis of the blood sample by microarray platform as described above is performed.

A classifier to distinguish subAR from TX (using e.g. at least 5 genes from Tables 5, 6, or 8, or at least 5 genes contacted by probes from Tables 5, 6, or 8) is applied to the gene expression data from the microarray analysis. The patient is classified as subAR.

Example 4. Non-TX vs TX Test Classification in Kidney Transplant Patient with AR A blood sample is taken from a kidney transplant patient with acute rejection. Gene expression analysis of the blood sample by microarray platform as described above is performed.

A classifier to distinguish TX from non-TX (from Tables 1, 2, 3, or 4 or at least 5 genes contacted by probes from Tables 1, 2, 3, or 4) is applied to the gene expression data from the microarray analysis. The patient is classified as non-TX.

Example 5. Development and Evaluation of a Blood-Based subAR Gene Expression Profile Classifier in a Clinical Setting A multi-center study (the Clinical Trials in Organ Transplantation 08, "CTOT-08") was conducted to develop a gene expression profile biomarker for subAR vs. no subAR and to assess its clinical validity. Serial blood samples paired with surveillance biopsies from precisely-phenotyped kidney recipients in both discovery and validation cohorts were used for biomarker development and validation. FIG. 10 depicts the study design for the CTOT-08 study. Subjects in the study underwent serial blood sampling (dark gray arrows) coupled with periodic kidney biopsies ("surveillance biopsies") (light gray arrows). Subjects diagnosed with subclinical acute rejection ("subAR") had more frequent blood sampling (lower dark gray arrows), and a follow-up biopsy 8 weeks later (skinny light gray arrows). Subjects presenting with renal dysfunction underwent "for-cause" biopsies (lowest light gray arrows). Episodes of clinical acute rejection ("cAR") also had more frequent blood sampling for 8 weeks, but no follow-up biopsy. All patients were scheduled for a biopsy at 24 months post-transplant as part of the clinical composite endpoint (CCE). FIG. 11 depicts the association of clinical phenotype with 24 month clinical composite endpoints. The chart illustrates the percentage of subjects who reached an endpoint (either the clinical composite endpoint—CCE) or each individual component of the CCE (Grade 2 IFTA on 24-month biopsy ["IFTA≥II" ]; any episode of biopsy proven acute rejection ["BPAR" ]; or drop in GFR>10 ml/min/1.73 m2 between months 4 and 24 ["ΔeGFR" ]). Subjects are divided by their clinical phenotypes (those with only TX on biopsies (blue bars/first bars in each group), those with either subAR or TX (orange bars/second bars in each group), subjects that had at least one episode of subAR (grey bars, third bars in each group), and then subjects that only had subAR (yellow bars, fourth bars in each group) on surveillance biopsies. FIG. 12A-B depicts the association of clinical phenotypes with de novo donor-specific antibody ("dnDSA") anytime post-transplant. FIG. 12A (top panel) shows the percentage of subjects that developed de novo donor specific antibodies (dnDSA) at any time during the study, either Class I (left-hand bars of each group/dark gray) or Class II (right-hand bars of each group/light gray), based on their clinical phenotypic group in the 24-month trial (subjects that had TX only on biopsies, at least one episode of subAR on biopsy, or only subAR on surveillance biopsy). FIG. 12B (bottom panel) shows a similar depiction to FIG. 12A with the association between dnDSA and clinical phenotypes but limited to biopsy results obtained in the first year post transplant. FIG. 13A-C depicts the association of the subclinical acute rejection ("subAR") gene expression profile (GEP) developed herein with 24-month outcomes and dnDSA. FIG. 13A (top panel) shows the association of the subAR GEP with 24 month outcomes. Shown are the percentage of subjects who reached an endpoint (either the composite endpoint—CCE) or each individual component of the CCE (Grade 2 IFTA on 24-month biopsy ["IFTA≥II" ]; any episode of biopsy proven acute rejection ["BPAR" ]; or drop in GFR >10 ml/min/1.73 m2 between months 4 and 24 ["ΔeGFR" ]). Subjects are divided by their Gene Expression Profile (GEP) tests results. Those that had only TX on GEP (blue bars/first bar in each group), those with either subAR or TX (orange bars/second bar in each group), subjects that had at least test with subAR (grey bars/third bar in each group), and then subjects that only had subAR tests (yellow bars/fourth bar in each group). FIG. 13B (middle panel) shows the association between the subAR gene expression profile (GEP) test and the development of de novo donor specific antibodies (dnDSA) anytime post-transplant. This includes GEP tests done any time in the 24-month study period. Shown are the percentage of subjects that developed dnDSA, both Class I (blue bars/first bar in each group) and Class II (orange bars/second bar in each group) grouped based on their GEP tests. The subject groups are those with only TX blood tests, at least one subAR blood test, or only subAR blood tests. All blood tests were paired with surveillance biopsies. FIG. 13C (bottom panel) shows a similar analysis to Panel B (association between GEP test and the development of de novo donor specific antibodies dnDSA), except that it is limited to the first year post transplant. FIG. 6 depicts the receiver operating characteristic (ROC) curve illustrating the process for identifying subAR classifier biomarkers. The 530 CTOT-08 paired peripheral blood and surveillance biopsy samples cohort from the CTOT "discovery" cohort were used.

Serial blood samples paired with surveillance biopsies from precisely-phenotyped kidney recipients in both discovery and validation cohorts were used for biomarker development. Differentially expressed genes mapped to biologically relevant molecular pathways of allograft rejection in both cohorts. A Random Forests model trained on the discovery dataset yielded a gene expression profile (GEP) for subAR (AUC 085). The GEP was further validated on an external cohort using the locked model and a defined threshold. This molecular biomarker diagnosed the absence of subAR in 72-75% of KT recipients (NPV: 78-88%), while the remaining 25-28% were identified as potentially harboring subAR (PPV: 47-61%). The subAR clinical phenotype and a positive biomarker test within the first 12 months following transplantation were both independently and significantly associated with the development of de novo donor-specific antibodies and worse transplant outcomes at 24 months. The data suggest that a blood-based biomarker can be used to non-invasively monitor kidney transplant recipients with stable renal function for the presence or absence of subAR. Use of a serial biomarker-informed monitoring strategy would risk-stratify patients and therefore limit the use of biopsies that are often negative unnecessary, improving both the clinician's ability to actively manage immunosuppression and transplant outcomes.

The approach presented herein has a number of analytical, statistical, and practical strengths. First, the gene expression profile validated herein has a biologically plausible mechanism connected to clinically significant outcomes (e.g. development of dnDSAs and worse graft outcome). Second, this approach allows for probability threshold selection emphasizing specificity/NPV of subAR over sensitivity/PPV, making it suitable for serial use in clinical practice to assess the absence of subAR and eliminating the need for indiscriminate and potentially unnecessary surveillance biopsies in most patients. Finally, the patient cohort design and analytical process used (e.g. use of centers with diverse populations agnostic to immunologic risk or immunosuppression regimen, use of clinical algorithms blinded to biomarker development, inclusion of confounders known to corrupt primary analyses, applied central biopsy reads, and ComBat adjustment) minimizes confounding factors common to other transplant rejection studies.

A. Characteristics of Patient Cohorts Selected for Discovery Validation 307 adult kidney transplant recipients were enrolled prospectively into CTOT-08 between March 2011 and May 2014 at 5 US transplant centers and followed them for 24 months. Study inclusion criteria were: male or female kidney transplant recipients (negative pregnancy test within 6 weeks of enrollment) age ≥18; able to provide informed consent; and recipients of a first or subsequent kidney transplant from either deceased or living donors. Combined and 'en-bloc' kidney grafts, and Human Immunodeficiency Virus or Hepatitis C Virus infected subjects were excluded. Participating sites that routinely perform surveillance biopsies were geographically selected to provide racial and ethnic diversity.

Kidney transplant recipients were contemporaneously enrolled into the NU transplant program's biorepository study, with eligibility criteria identical to CTOT-08. Patients undergo surveillance biopsies at NU with a frequency similar to CTOT-08. Patients who underwent surveillance biopsies at NU but who did not participate in CTOT-08 were enrolled into the NU biorepository study.

Figure 5:
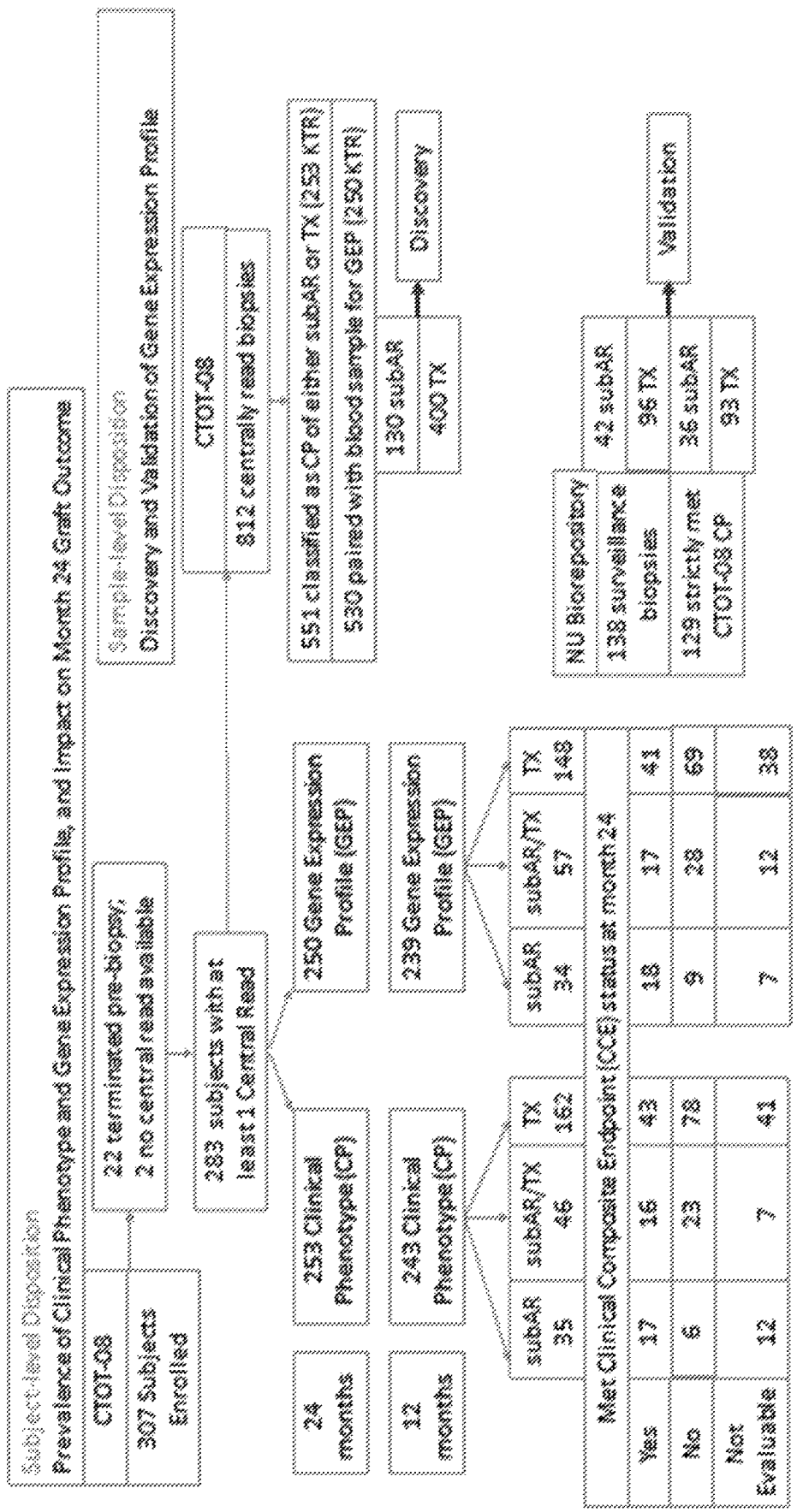
FIG. 5 is a diagram showing cohort selection and division for CTOT-08 and NU biorepository paired sample cohorts and discovery and validation cohorts derived therefrom; these cohorts were utilized to develop classifier methods described herein.

Disposition of transplant recipients into CTOT-08 and NU biorepository cohorts, as well as their sub-selection into discovery and validation cohorts is presented in FIG. 5. As demonstrated in FIG. 5, the NU repository cohort was used for validation of the blood-based subAR gene expression profile classifier, while the CTOT-08 cohort was used for discovery. The remaining 551 were classified as having the clinical phenotypes of either subAR (n=136[24.7%]; 79% 'borderline changes', 21%>1A rejection) or TX (no rejection or other histologic findings; n=415[75.3%]). 530 surveillance biopsies with available paired peripheral blood samples were used for biomarker discovery. Despite meeting the more general definition of either rejection or no rejection on a surveillance biopsy, the remaining 21 paired samples did not meet the strict criteria for either TX or subAR based on the pre-defined phenotype algorithm and were therefore excluded. Of note, there were no instances of BK virus nephropathy among the 530 biopsies. In contrast to the CTOT-08 discovery cohort, patients contributing to the Northwestern University (NU) Biorepository did not undergo serial sampling. Instead, these paired samples, used for validation of the biomarker were obtained at the time of surveillance biopsies performed at the NU transplant center and represent single time points within 24 months following kidney transplantation.

Of 307 subjects enrolled in CTOT-08, 283 with stable renal function had centrally-read surveillance biopsies and serial clinical data, and 253/283 had sufficient data to define the clinical phenotype of either subAR or Transplant eXcellent (TX) (i.e. no subAR) for each paired (surveillance biopsy and peripheral blood) sample used for biomarker discovery. During the 24-month observational period, these 253 subjects underwent 742 centrally-read biopsies; 191 were 'for cause' (associated with acute renal dysfunction) and were therefore not considered as surveillance biopsies, performed only in the setting of stable renal function.

Clinical parameters for both patients in both the CTOT-08 and NU transplant biorepository studies are presented in Table 7. There were no discemable differences in demographics including type of immunosuppression between the groups. Of the 253 precisely-phenotyped CTOT-08 subjects with stable renal function who underwent >1 surveillance biopsies, 33 (13.0%) demonstrated only subAR (no TX), 146 subjects (57.71%) only TX (no subAR), and 74 (29.2%) subjects demonstrated individual instances of either subAR or TX (i.e. at least 1 instance of subAR during the 24-month study). The subAR only (no instances of TX per surveillance biopsies during the study period) and the subAR or TX groups collectively represent subjects with at least 1 episode of subAR (>1 subAR). At the patient-level, the prevalent incidence of >1 biopsy-proven instance(s) of subAR was 42.3% (107/253) versus 57.7% for TX only. Since, subjects in the NU biorepository did not undergo serial sampling, and therefore there were only 2 groups: the sample-level prevalent incidence of subAR was 27.9% (36/129) compared to 72.1% for TX (93/129).

CTOT-08 subjects underwent multiple surveillance biopsies during the 24 month study. While some subjects only demonstrated either subAR or TX phenotypes, others demonstrated more than one phenotype at different times. Therefore, we classified subjects into 3 phenotypic groups: subjects with surveillance biopsies demonstrating subAR only (no TX), TX only (no subAR), and subjects with individual biopsies demonstrating either subAR or TX. This third group therefore consisted of subjects who had experienced >1 (at least 1) instance of subAR and >1 (at least 1) instance of TX during the study period.

During the CTOT-08 study period, clinical care followed standard practice at each center for immunosuppression and prophylaxis regimens. All biopsies were processed for routine histology, Simian Virus-40 (SV40) and c4d staining and were read by a central pathologist blinded to the clinical course using Banff 2007 criteria (Solez et al. Am. J. Transplant. 8, 753-760 (2008)).

All biopsies were centrally read. Clinical phenotypes were assigned by the Data Coordinating Center (DCC at Rho Federal Systems) for the discovery and validation cohorts using the following predefined algorithm:

Sample-Level:

SubAR: histology on a surveillance biopsy consistent with acute rejection (≥Banff borderline cellular rejection and/or antibody mediated rejection) AND stable renal function, defined as serum creatinine <2.3 mg/dl and <20% increase in creatinine compared to a minimum of 2-3 prior values over a mean period and range of 132 and 75-187 days, respectively;

Transplant eXcellence (TX): normal histology on surveillance biopsy (no evidence of rejection—Banff i=0 and t=0, g=0, ptc=0; ci=0 or 1 and ct=0 or 1) AND stable renal function as defined above. Surveillance biopsies were performed on all subjects at 2-6, 12 and 24 months following transplantation.

Subject Level:

CTOT-08 subjects underwent multiple surveillance biopsies during the 24 month study. While some subjects only demonstrated either subAR or TX phenotypes, others demonstrated more than one phenotype at different times. Therefore, we classified subjects into 3 phenotypic groups: subjects with surveillance biopsies demonstrating subAR only (no TX), TX only (no subAR), and subjects with individual biopsies demonstrating either subAR or TX. This third group therefore consisted of subjects who had experienced >1 (at least 1) instance of subAR and >1 (at least 1) instance of TX during the study period Subjects diagnosed with subAR on a surveillance biopsy were managed based on each site's interpretation of the histopathology, according to local practice; they subsequently underwent intensive monitoring consisting of blood sample collection every 2 weeks and repeat biopsy at week 8. Intense monitoring was limited to 1 subAR episode per subject.

TABLE 7

Donor and recipient patient-level demographics and prevalence of clinical phenotype for both CTOT-08 and NU Biorepository subjects.

| | CTOT-08 Cohort (N = 253) | | | NU Cohort (N = 129) | |
|---|---|---|---|---|---|
| Characteristic-n (%) | SubAR, no TX (N = 33) | TX, no SubAR (N = 146) | SubAR and TX (N = 74) | SubAR, no TX (N = 36) | TX, no SubAR (N = 93) |
| Donor Demographics Age - yr | | | | | |
| Mean ± SD | 39.0 ± 15.57 | 38.1 ± 13.49 | 43.1 ± 13.30 | 40.7 ± 13.63 | 38.6 ± 13.28 |
| Range | 10-66 | 8-71 | 6-71 | 13-73 | 13-73 |
| Male Sex | 17 (51.5) | 75 (51.4) | 39 (52.7) | 23 (63.9) | 46 (49.5) |
| Race | | | | | |
| White | 26 (78.8) | 98 (67.1) | 59 (79.7) | 23 (63.9) | 52 (55.9) |
| Black or African American | 2 (6.1) | 23 (15.8) | 2 (2.7) | 5 (13.9) | 15 (16.1) |
| Other | 1 (3.0) | 6 (4.1) | 4 (5.4) | 8 (22.2) | 25 (26.9) |
| Unknown or Not Reported | 4 (12.1) | 19 (13.0) | 9 (12.2) | 0 | 1 (1.1) |
| Ethnicity | | | | | |
| Hispanic or Latino | 5 (15.2) | 19 (13.0) | 11 (14.9) | 6 (16.7) | 21 (22.6) |
| Not Hispanic or Latino | 25 (75.8) | 110 (75.3) | 56 (75.7) | 30 (83.3) | 71 (76.3) |
| Unknown or Not Reported | 3 (9.1) | 17 (11.6) | 7 (9.5) | 0 | 1 (1.1) |
| Recipient Demographics Age - yr | | | | | |
| Mean ± SD | 50.1 ± 14.76 | 50.2 ± 13.69 | 53.4 ± 13.53 | 52.1 ± 13.15 | 53.0 ± 12.67 |
| Range | 19-75 | 21-78 | 21-78 | 22-72 | 25-75 |
| Male Sex | 22 (66.7) | 94 (64.4) | 51 (68.9) | 22 (61.1) | 52 (55.9) |
| Race | | | | | |
| White | 23 (69.7) | 87 (59.6) | 51 (68.9) | 21 (58.3) | 49 (52.7) |
| Black or African American | 6 (18.2) | 34 (23.3) | 8 (10.8) | 6 (16.7) | 18 (19.4) |
| Other | 4 (12.1) | 11 (7.5) | 5 (6.8) | 9 (25.0) | 26 (28.0) |
| Unknown or Not Reported | 0 | 14 (9.6) | 10 (13.5) | 0 | 0 |
| Ethnicity | | | | | |
| Hispanic or Latino | 2 (6.1) | 27 (18.5) | 12 (16.2) | 7 (19.4) | 15 (16.1) |
| Not Hispanic or Latino | 30 (90.9) | 112 (76.7) | 57 (77.0) | 28 (77.8) | 74 (79.6) |
| Unknown or Not Reported | 1 (3.0) | 7 (4.8) | 5 (6.8) | 1 (2.8) | 4 (4.3) |
| Deceased Donor | 22 (66.7) | 60 (41.1) | 26 (35.1) | 19 (52.8) | 30 (32.3) |
| Primary Reason for ESRD | | | | | |
| Cystic (includes PKD) | 2 (6.1) | 13 (8.9) | 14 (18.9) | 4 (11.1) | 10 (10.8) |
| Diabetes Mellitus | 8 (24.2) | 30 (20.5) | 15 (20.3) | 10 (27.8) | 23 (24.7) |
| Glomerulonephritis | 9 (27.3) | 47 (32.2) | 13 (17.6) | 8 (22.2) | 28 (30.1) |
| Hypertension | 4 (12.1) | 29 (19.9) | 12 (16.2) | 7 (19.4) | 18 (19.4) |
| Other | 10 (30.3) | 27 (18.5) | 20 (27.0) | 7 (19.4) | 14 (15.1) |
| Secondary Reason for ESRD | | | | | |
| Cystic (includes PKD) | 0 | 1 (0.7) | 0 | 0 | 1 (1.1) |
| Diabetes Mellitus | 0 | 7 (4.8) | 1 (1.4) | 2 (5.6) | 2 (2.2) |
| Glomerulonephritis | 0 | 7 (4.8) | 2 (2.7) | 3 (8.3) | 5 (5.4) |

TABLE 7-continued

Donor and recipient patient-level demographics and prevalence of clinical phenotype for both CTOT-08 and NU Biorepository subjects.

| | CTOT-08 Cohort (N = 253) | | | NU Cohort (N = 129) | |
|---|---|---|---|---|---|
| Characteristic-n (%) | SubAR, no TX (N = 33) | TX, no SubAR (N = 146) | SubAR and TX (N = 74) | SubAR, no TX (N = 36) | TX, no SubAR (N = 93) |
| Hypertension | 6 (18.2) | 14 (9.6) | 2 (2.7) | 4 (11.1) | 15 (16.1) |
| Other | 0 | 9 (6.2) | 2 (2.7) | 0 | 1 (1.1) |
| None Reported | 27 (81.8) | 108 (74.0) | 67 (90.5) | 27 (75.0) | 69 (74.2) |
| Recipient PRA at Transplant | | | | | |
| PRA Class I % | | | | | |
| n | 29 | 107 | 62 | 36 | 93 |
| Mean ± SD | 7.4 ± 20.59 | 7.9 ± 20.85 | 6.9 ± 20.48 | 20.3 ± 29.41 | 19.5 ± 31.13 |
| Range | 0-100 | 0-100 | 0-96 | 0-89 | 0-99 |
| PRA Class II % | | | | | |
| n | 29 | 107 | 61 | 36 | 93 |
| Mean ± SD | 11.3 ± 29.03 | 7.6 ± 21.29 | 6.1 ± 18.52 | 17.4 ± 31.36 | 12.9 ± 25.54 |
| Range | 0-100 | 0-100 | 0-80 | 0-100 | 0-100 |
| PRA Single Antigen cPRA % | | | | | |
| n | 26 | 86 | 46 | 36 | 93 |
| Mean ± SD | 32.8 ± 42.06 | 29.4 ± 35.82 | 25.9 ± 35.46 | 18.1 ± 28.51 | 11.9 ± 28.19 |
| Range | 0-100 | 0-99 | 0-100 | 0-91 | 0-98 |
| Donor and Recipient CMV Status | | | | | |
| D-,R+ | 3 (9.1) | 25 (17.1) | 16 (21.6) | 11 (30.6) | 18 (19.4) |
| D+,R- | 10 (30.3) | 23 (15.8) | 13 (17.6) | 7 (19.4) | 22 (23.7) |
| D-,R- | 7 (21.2) | 33 (22.6) | 21 (28.4) | 5 (13.9) | 16 (17.2) |
| D+,R+ | 11 (33.3) | 60 (41.1) | 20 (27.0) | 13 (36.1) | 36 (38.7) |
| Donor, Recipient, or Both not tested | 2 (6.1) | 5 (3.4) | 4 (5.4) | 0 | 1 (1.1) |
| Use of Induction Therapy | | | | | |
| Alemtuzumab | 19 (57.6) | 74 (50.7) | 42 (56.8) | 29 (80.6) | 80 (86.0) |
| Anti-Thymocyte Globulin | 12 (36.4) | 40 (27.4) | 14 (18.9) | 0 | 0 |
| Basiliximab | 3 (9.1) | 25 (17.1) | 18 (24.3) | 7 (19.4) | 11 (11.8) |
| Use of Desensitization Therapy | | | | | |
| Received Any Desensitization Therapy | 0 | 9 (6.2) | 7 (9.5) | 4 (11.1) | 6 (6.5) |
| Use of Maintenance Therapy | | | | | |
| Steroid | 24 (72.7) | 71 (48.6) | 50 (67.6) | 13 (36.1) | 27 (29.0) |
| Tacrolimus | 33 (100) | 145 (99.3) | 74 (100) | 30 (83.3) | 89 (95.7) |
| Cyclosporine | 3 (9.1) | 7 (4.8) | 4 (5.4) | 3 (8.3) | 2 (2.2) |
| Azathioprine | 1 (3.0) | 0 | 0 | 1 (2.8) | 0 |
| MMF | 33 (100) | 143 (97.9) | 74 (100) | 35 (97.2) | 92 (98.9) |
| mTOR Inhibitor | 1 (3.0) | 11 (7.5) | 5 (6.8) | 3 (8.3) | 2 (2.2) |
| Leflunomide | 0 | 2 (1.4) | 2 (2.7) | 0 | 0 |
| Belatacept | 0 | 1 (0.7) | 0 | 0 | 0 |

B. Development of a subAR Gene Expression Profile Classifier to Stratify Patients Using a Defined Probability Threshold A biomarker panel designed to correlate with either subAR vs no subAR (TX) on a surveillance biopsy on patients with stable renal function was developed using differential gene expression data from 530 CTOT-08 peripheral blood samples (subAR 130 [24.5%]: TX 400) paired with surveillance biopsies from 250 subjects.

Peripheral blood collected in PAXGene (BD BioSciences, San Jose CA) tubes was shipped to The Scripps Research Institute (TSRI) and processed in batches. RNA was extracted from Paxgene tubes using the Paxgene Blood RNA system (PreAnalytiX GmbH, Hombrechtikon, Switzerland) and Ambion GLOBINclear (Life Technologies, Carlsbad, CA). Biotinylated cRNA was prepared with Ambion MessageAmp Biotin II kit (Ambion) and hybridized using Affymetrix HT HG-U133+PM Array Plates and the Peg Arrays and the Gene Titan MC instrument (Thermo Fisher Scientific, Waltham MA) (GEO Accession #GSE107509). Correction and normalization parameters (Frozen RMA) were saved and applied to all samples.

Figure 8:
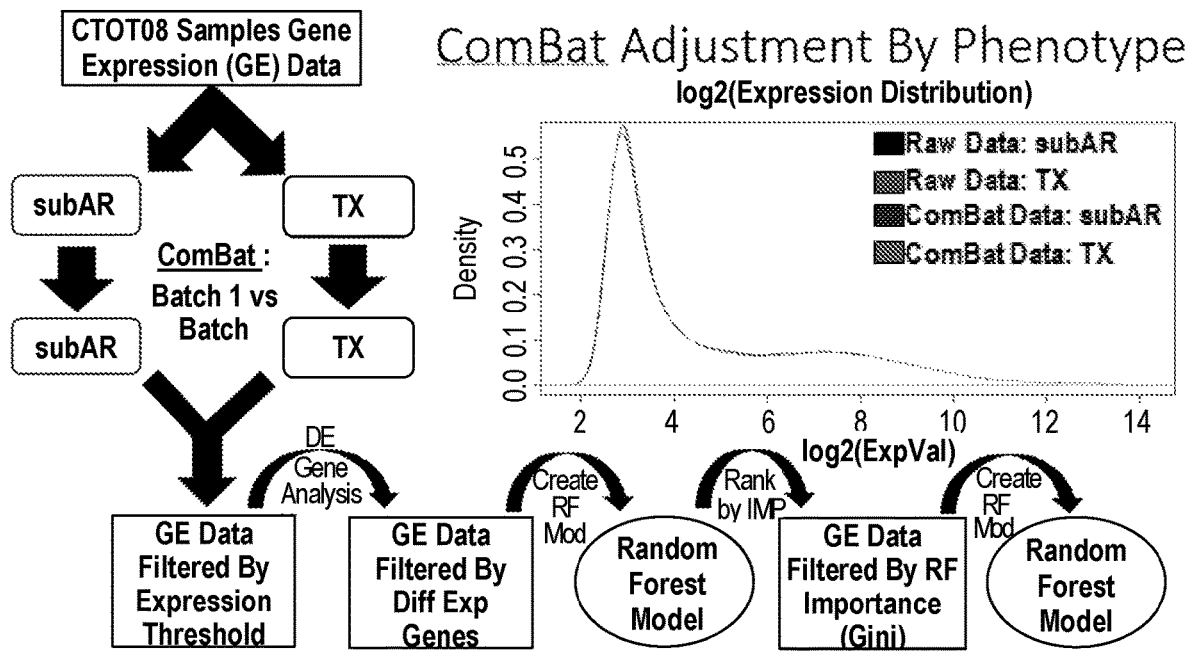
FIG. 8 is a diagram illustrating the workflow used for the discovery of the subAR gene expression profile classifier described in Example 1. Peripheral blood collected in PAXGene tubes was processed in batches using correction and normalization parameters. Following ComBat adjustment for batch effect using surrogate variable analysis, differential gene expression analysis was performed, and the data were then used to populate Random Forest models. Gini importance was used to select the top model optimized for AUC. Different probability thresholds were then assessed to optimize performance of the biomarker

FIG. 8 illustrates the workflow used for the discovery of the subAR gene expression profile classifier. Peripheral blood collected in PAXGene tubes was processed in batches using correction and normalization parameters. Following ComBat adjustment for batch effect using surrogate variable analysis, differential gene expression analysis was performed, and the data were then used to populate Random Forest models. Gini importance was used to select the top model optimized for AUC. Different probability thresholds were then assessed to optimize performance of the biomarker Following ComBat (Johnson et al. Biostatistics 8, 118-127 (2007)) adjustment for batch effect using surrogate variable analysis (Leek et al. Bioinformatics 28, 882-883 (2012)), differential gene expression analysis was performed (Linear Models for Microarray data—LIMMA) and a False Discovery Rate (FDR)<0.05 was selected. To test for and validate biologic relevance of differential gene expression data, we compared gene pathway mapping (LIMMA; FDR <0.05) between both cohorts using: 1) Ingenuity Pathway Analysis (Qiagen), 2) Database for Annotation, Visualization and Integrated Discovery (DAVID) (Huang et al. Genome Biol. 8, R183.1-R183.16 (2007)), and 3) Gene Set Enrichment Analysis (GSEA) (Subramanian et al. Genome Biol. 8, R183.1-R183.16 (2007)). Differential gene expression data were then used to populate Random Forests models. Gini importance were used to select the top model optimized for AUC. Bootstrap resampling (54) was used to test for overfitting of the final model. Threshold selection was based on model performance metrics in the discovery cohort. Based on their dichotomous outcome (either subAR or TX), these profiles were compared to the clinical phenotypes to determine the performance of the classifiers. We then validated the locked model/threshold of the subAR gene expression profile on the independent NU biorepository cohort, a second cohort (NU biorepository), independent of CTOT-08. The gene expression profiles were also used for sample- and patient-level classifications to determine associations with clinical endpoints and transplant outcomes.

A Random Forests model to was selected for the biomarker panel (AUC 0.85; 0.84 after internal validation with bootstrap resampling) using 100,000 trees, an expression threshold of 5, and false discovery rate (FDR 0.01). We then selected a predicted probability threshold of 0.375 based on best overall performance, favoring specificity and NPV (87% and 88%) over sensitivity and PPV (64% and 61%, respectively). A ROC curve-based analysis of this model selection procedure is presented in FIG. 6. The classifiers for this model selection consisted of 61 probe sets that mapped to 57 genes. Of interest, 38/57 genes were up-regulated for subAR vs. TX (19 down-regulated), only 7/57 mapped to alloinflammatory pathways (Ingenuity) and except for PKM and IFNAR1, they were significant at FDR<5%; of the 7 that mapped to alloinflammatory pathways, only 2/7 were up-regulated and the other 5 were down-regulated (Table 8 shows the gene classifiers for this locked model).

TABLE 8

Gene expression Profile Classifier Genes for SubAR in CTOT-08

| Gene Symbol | Gene Name |
|---|---|
| AARSD1 | alanyl-tRNA synthetase domain containing 1 |
| AP2M1 | adaptor related protein complex 2 mu 1 subunit |
| ARHGDIB | Rho GDP dissociation inhibitor beta |
| ASB6 | ankyrin repeat and SOCS box containing 6 |
| BTD | biotinidase |
| C20orf27 | chromosome 20 open reading frame 27 |
| C9orf16 | chromosome 9 open reading frame 16 |
| CFL1 | cofilin 1 (down-regulated in subAR) |
| CIAO1 | cytosolic iron-sulfur assembly component 1 |
| CNDP2 | carnosine dipeptidase 2 |
| CXorf56 | chromosome X open reading frame 56 |
| DDX39B | DExD-box helicase 39B |
| EMP3 | epithelial membrane protein 3 |
| EXOC4 | exocyst complex component 4 |
| FAM103A1 | family with sequence similarity 103 member A1 |
| FCGR2B | Fc fragment of IgG receptor IIb (upregulated in subAR) |
| GNAI2 | G protein subunit alpha i2 (down-regulated in subAR) |
| HLA-J | major histocompatibility complex, class I, J (pseudogene) |
| HMGXB3 | HMG-box containing 3 |
| HSPB1 | heat shock protein family B (small) member 1 (down-regulated in subAR) |

TABLE 8-continued

Gene expression Profile Classifier Genes for SubAR in CTOT-08

| Gene Symbol | Gene Name |
|---|---|
| IFNAR1 | interferon alpha and beta receptor subunit 1 (up-regulated in subAR) |
| ILK | integrin linked kinase |
| KCMF1 | potassium channel modulatory factor 1 |
| KIAA0141 | KIAA0141 |
| KLHDC4 | kelch domain containing 4 |
| LOC101928595 | uncharacterized LOC101928595 |
| LRWD1 | leucine rich repeats and WD repeat domain containing 1 |
| MIB2 | mindbomb E3 ubiquitin protein ligase 2 |
| MYO19 | myosin XIX |
| MYO1C | myosin IC |
| MYPOP | Myb related transcription factor, partner of profilin |
| OS9 | OS9, endoplasmic reticulum lectin |
| PFN1 | profilin 1 |
| PKM | pyruvate kinase M1/2 (down-regulated in subAR |
| PKNOX1 | PBX/knotted 1 homeobox 1 |
| PTK2B | protein tyrosine kinase 2 beta (down-regulated in subAR) |
| RBBP9 | RB binding protein 9, serine hydrolase |
| RBM3 | RNA binding motif protein 3 |
| RBM5 | RNA binding motif protein 5 |
| RLIM | ring finger protein, LIM domain interacting |
| RPUSD3 | RNA pseudouridylate synthase domain containing 3 |
| RUSC1 | RUN and SH3 domain containing 1 |
| SARNP | SAP domain containing ribonucleoprotein |
| SH3BGRL3 | SH3 domain binding glutamate rich protein like 3 |
| SLC25A19 | solute carrier family 25 member 19 |
| SLC35D2 | solute carrier family 35 member D2 |
| SNX19 | sorting nexin 19 |
| SNX20 | sorting nexin 20 |
| STN1 | STN1, CST complex subunit |
| TMEM62 | transmembrane protein 62 |
| TPMT | thiopurine S-methyltransferase |
| TRAPPC1 | trafficking protein particle complex 1 |
| TTC9C | tetratricopeptide repeat domain 9C |
| TWF2 | twinfilin actin binding protein 2 |
| UCP2 | uncoupling protein 2 |
| UQCR11 | ubiquinol-cytochrome c reductase, complex III subunit XI |
| USP31 | ubiquitin specific peptidase 31 |

C. Validation of the Classification Performance of the subAR Gene Expression Profile Classifier The locked model classifiers were then tested at the defined threshold (0.375) first on 138 subjects from the NU biorepository (validation set #1) who had undergone surveillance biopsies (subAR 42 [30.4%]: TX 96). Performance metrics consisted of NPV 78%, PPV 5100. The same locked model/threshold was then tested on a subset of 129/138 (subAR 36 [27.90%]: TX 93) who met the strict study CTOT-08 criteria for the clinical phenotype definitions of subAR and TX (validation set #2); performance metrics consisted of NPV 80%; PPV 47% (see FIG. 7 which depicts the results for validation set 1 in the left panel and validation 2 in the right panel). The biomarker test results were interpreted dichotomously as 'positive' (i.e. correlating with a clinical phenotype of subAR) if the probability exceeded the 0.375 threshold and 'negative' (i.e. correlating with TX) if <0.375.

To translate the performance of the biomarker into a narrative more relevant to clinical application, the ability to diagnose the presence or absence of subAR in any given sample using the biomarker was calculated, taking into consideration the prevalent incidence of both subAR and TX compared to the frequency of a correct positive vs. negative biomarker test result. Accordingly, a negative call was made (no subAR) in 72-75% of patients (NPV 78-88%) vs. a positive call (subAR) 25-28% of the time (PPV 47-61%). The performance metrics of this validation are presented in Table 9.

TABLE 9

Test Performance by Locked Probability Threshold following Random Forest Model Selection

| Dataset | Paired samples | TX:subAR (% subAR prevalence) | Prob. Thresh | % Neg (Spared biopsy) | NPV | True Neg | False Neg | % Pos (pick up subAR) | PPV | True Pos | False Pos |
|---|---|---|---|---|---|---|---|---|---|---|---|
| Discovery set | N = 530 | 400:130 (24.5%) | 0.375 | 74.7% | 88% | 349 | 47 | 25.3% | 61% | 83 | 51 |
| Validation set #1 | N = 138 | 96:42 (30.4%) | 0.375 | 71.7% | 78% | 77 | 22 | 28.3% | 51% | 20 | 19 |
| Validation set #2 | N = 129/138 | 93:36 (27.9%) | 0.375 | 72.1% | 80% | 74 | 19 | 27.9% | 47% | 17 | 19 | subAR is 'positive' test;
Prevalence = subAR/(subAR + TX);
% Pos = TP + FP/total;
% Neg = (TN + FN)/total Thus, if used for serial monitoring, the biomarker could be used to stratify patients with stable renal function into a low risk of harboring subAR with a relatively high degree of certainty, avoiding the routine use of indiscriminate surveillance biopsies in the majority (72-75%) of patients. In the remaining 25-28%, more informed management decisions, including the use of a biomarker-prompted biopsy could be considered depending on all other clinical and laboratory data.

Example 6. Evaluation of Biologic Relevance of Differentially Expressed Genes Used to Develop the subAR Gene Expression Profile The gene expression profile biomarker for SubAR developed in Example 5, was evaluated for the biological relevance of the differentially expressed genes that were used to develop it. Differentially expressed genes determined by LIMMA with a FDR of <0.05 (Smyth et al. Statistics for Biology and Health 23, 397-420. Springer, New York (2005)) from the 530 CTOT-08 discovery samples used to populate the Random Forests models underwent biologic pathway mapping using three well established software packages:
1) Ingenuity Pathway Analysis (IPA) (Qiagen)
   a) IPA identified 46 significant canonical pathways (Benjamini-Hochberg corrected p-value <0.05), several linked to T and B-cell immunity, including the T Cell Receptor, CD28, CTLA4 in Cytotoxic T Lymphocytes, Regulation of IL-2 Expression, PKCθ, iCOS-iCOSL, B Cell Receptor, Natural Killer Cell, and NFAT Regulation of the Immune Response signaling pathways. 3958 probe sets mapped to 3060 differentially expressed genes (FDR <0.1) from the 530 CTOT-08 samples (Table 10).

TABLE 10

Significant canonical pathways (Benjamini-Hochberg corrected p-value < 0.05) identified by Ingenuity Pathway Analysis from the CTOT-08 Discovery cohort.

| Ingenuity Canonical Pathways | -log(B-H p-value) | B-H p-value |
|---|---|---|
| EIF2 Signaling | 12 | 1.00E−12 |
| Mitochondrial Dysfunction | 5.83 | 1.48E−06 |
| Regulation of eIF4 and p70S6K Signaling | 5.78 | 1.66E−06 |
| Sirtuin Signaling Pathway | 4.96 | 1.10E−05 |
| Oxidative Phosphorylation | 4.87 | 1.35E−05 |
| Protein Ubiquitination Pathway | 4.68 | 2.09E−05 |
| T Cell Receptor Signaling | 4.54 | 2.88E−05 |
| CTLA4 Signaling in Cytotoxic T Lymphocytes | 4.28 | 5.25E−05 |
| CD28 Signaling in T Helper Cells | 4.04 | 9.12E−05 |
| ATM Signaling | 3.99 | 1.02E−04 |
| mTOR Signaling | 3.78 | 1.66E−04 |
| iCOS-iCOSL Signaling in T Helper Cells | 3.72 | 1.91E−04 |
| Assembly of RNA Polymerase II Complex | 3.26 | 5.50E−04 |
| Glucocorticoid Receptor Signaling | 3.24 | 5.75E−04 |
| Hereditary Breast Cancer Signaling | 3.04 | 9.12E−04 |
| PKCθ Signaling in T Lymphocytes | 2.99 | 1.02E−03 |
| Estrogen Receptor Signaling | 2.99 | 1.02E−03 |
| Natural Killer Cell Signaling | 2.89 | 1.29E−03 |
| Cleavage and Polyadenylation of Pre-mRNA | 2.72 | 1.91E−03 |
| Role of CHK Proteins in Cell Cycle Checkpoint Control | 2.5 | 3.16E−03 |
| Regulation of IL-2 Expression in Activated and Anergic T | 2.5 | 3.16E−03 |
| Small Cell Lung Cancer Signaling | 2.38 | 4.17E−03 |
| Role of NFAT in Regulation of the Immune Response | 2.22 | 6.03E−03 |
| Calcium-induced T Lymphocyte Apoptosis | 2.22 | 6.03E−03 |
| Dolichyl-diphosphooligosaccharide Biosynthesis | 2.18 | 6.61E−03 |
| B Cell Receptor Signaling | 2.16 | 6.92E−03 |
| p70S6K Signaling | 1.9 | 1.26E−02 |
| Nucleotide Excision Repair Pathway | 1.71 | 0.019 |
| Huntington's Disease Signaling | 1.7 | 0.020 |
| Th1 Pathway | 1.7 | 0.020 |
| VEGF Signaling | 1.7 | 0.020 |
| Non-Small Cell Lung Cancer Signaling | 1.61 | 0.025 |
| Th1 and Th2 Activation Pathway | 1.58 | 0.026 |
| tRNA Charging | 1.42 | 0.038 |
| Role of BRCA1 in DNA Damage Response | 1.42 | 0.038 |
| Purine Nucleotides De Novo Biosynthesis II | 1.41 | 0.039 |
| PI3K Signaling in B Lymphocytes | 1.41 | 0.039 |
| Sumoylation Pathway | 1.38 | 0.042 |
| April Mediated Signaling | 1.37 | 0.043 |
| Inosine-5'-phosphate Biosynthesis II | 1.35 | 0.045 |
| Acute Myeloid Leukemia Signaling | 1.35 | 0.045 |
| NF-KB Activation by Viruses | 1.35 | 0.045 |
| PI3K/AKT Signaling | 1.35 | 0.045 |
| Glioblastoma Multiforme Signaling | 1.32 | 0.048 |

TABLE 10-continued

Significant canonical pathways (Benjamini-Hochberg corrected p-value < 0.05) identified by Ingenuity Pathway Analysis from the CTOT-08 Discovery cohort.

| Ingenuity Canonical Pathways | -log(B-H p-value) | B-H p-value |
|---|---|---|
| CD40 Signaling | 1.31 | 0.049 |
| Unfolded protein response | 1.31 | 0.049 | b) Additionally, in the NU validation set, IPA identified 15 shared pathway genes with sets of shared genes directionally validated (Table 11). This analysis represented 871 probe sets mapped to 687 differentially expressed genes (FDR <0.1) from 129 NU biorepository samples. The list for each pathway below (Table 11) shows only shared genes that were present in both cohorts and were also directionally validated (up or down-regulated in both cohorts) with an average directional agreement of 48%; range 17-89%).

TABLE 11

15 shared pathways identified by Ingenuity Pathway Analysis between the CTOT-08 Discovery and the 129 NU validation cohorts

| Symbol | Entrez Gene Name | Affymetrix (A1#) | Affymetrix (A2#) | Expr Log Ratio (A1#) | Expr p-value (A1#) | Expr Log Ratio (A2) | Expr p-value (A2) | Agreement between Discovery and Validation |
|---|---|---|---|---|---|---|---|---|
| EIF 2 Signaling | | | | | | | | |
| CDK11A | cyclin dependent kinase 11A | 210474_PM_s_at | 211289_PM_x_at | 5.856 | 0.013 | 3.676 | 0.0674 | 89% |
| EIF3F | eukaryotic translation initiation factor 3 subunit F | 200023_PM_s_at | 226014_PM_at | 9.915 | 0.0479 | 2.858 | 0.00665 | |
| PIK3R5 | phosphoinositide-3-kinase regulatory subunit 5 | 227645_PM_at | 220566_PM_at | 15.229 | 0.0712 | 3.662 | 0.0925 | |
| PTBP1 | polypyrimidine tract binding protein 1 | 216306_PM_x_at | 212016_PM_s_at | 12.723 | 0.0617 | 3.462 | 0.0135 | |
| RPL14 | ribosomal protein L14 | 213588_PM_x_at | 219138_PM_at | 8.728 | 0.0195 | 1.961 | 0.000211 | |
| RPL27A | ribosomal protein L27a | 203034_PM_s_at | 212044_PM_s_at | 16.762 | 0.046 | 1.708 | 4.33E-09 | |
| RPL37A | ribosomal protein L37a | 201429_PM_s_at | 214041_PM_x_at | 21.873 | 0.0476 | 3.026 | 0.035 | |
| RPLP2 | ribosomal protein lateral stalk subunit P2 | 200909_PM_s_at | 200909_PM_s_at | 29.994 | 0.0791 | −11.781 | 0.0524 | |
| RPS19 | ribosomal protein S19 | 242451_PM_x_at | 202648_PM_at | 6.411 | 0.0377 | 2.337 | 0.0000137 | |
| T-cell Receptor Signaling | | | | | | | | |
| CBL | Cbl proto-oncogene | 225234_PM_at | 229010_PM_at | −7.307 | 0.086 | 2.59 | 0.0187 | 50% |
| LCP2 | lymphocyte cytosolic protein 2 | 205270_PM_s_at | 244578_PM_at | 13.175 | 0.0285 | 1.811 | 0.000182 | |
| NFATC3 | nuclear factor of activated T-cells 3 | 207416_PM_s_at | 225137_PPM_at | 6.702 | 0.0321 | −2.819 | 0.0128 | |
| PIK3R5 | phosphoinositide-3-kinase regulatory subunit 5 | 227645_PM_at | 220566_PM_at | 15.229 | 0.0712 | 3.662 | 0.0925 | |
| CD 28 Signaling | | | | | | | | |
| CDC42 | cell division cycle 42 | 208727_PM_s_at | 208727_PM_s_at | −5.037 | 0.00719 | 2.715 | 0.0127 | 40% |
| ITPR2 | inositol 1,4,5-trisphosphate receptor type 2 | 202661_PM_at | 211360_PM_s_at | 7.618 | 0.0821 | 1.726 | 0.000000987 | |
| LCP2 | lymphocyte cytosolic protein 2 | 205270_PM_s_at | 244578_PM_at | 13.175 | 0.0285 | 1.811 | 0.000182 | |

TABLE 11-continued 15 shared pathways identified by Ingenuity Pathway Analysis between the
CTOT-08 Discovery and the 129 NU validation cohorts

| Symbol | Entrez Gene Name | Affymetrix (A1#) | Affymetrix (A2#) | Expr Log Ratio (A1#) | Expr p-value (A1#) | Expr Log Ratio (A2) | Expr p-value (A2) | Agreement between Discovery and Validation |
|---|---|---|---|---|---|---|---|---|
| NFATC3 | nuclear factor of activated T-cells 3 | 207416_PM_s_at | 225137_PM_at | 6.702 | 0.0321 | −2.819 | 0.0128 | |
| PIK3R5 | phosphoinositide-3-kinase regulatory subunit 5 | 227645_PM_at | 220566_PM_at | 15.229 | 0.0712 | 3.662 | 0.0925 | |
| ATM Signalling | | | | | | | | |
| CREB1 | CAMP responsive element binding protein 1 | 225565_PM_at | 204312_PM_x_at | −6.724 | 0.0757 | 5.191 | 0.098 | 50% |
| GADD45B | growth arrest and DNA damage inducible beta | 209304_PM_x_at | 213560_PM_at | 7.698 | 0.0123 | 2.295 | 0.000121 | |
| HP1BP3 | heterochromatin protein 1 binding protein 3 | 224591_PM_at | 220633_PM_s_at | 10.751 | 0.0548 | 4.348 | 0.0244 | |
| PPM1D | protein phosphatase, Mg2+/Mn2+ dependent 1D | 230330_PM_at | 230330_PM_at | 8.768 | 0.0363 | 4.7 | 0.0427 | |
| PPP2R1A | protein phosphatase 2 scaffold subunit alpha | 200695_PM_at | 200695_PM_at | −6.035 | 0.0188 | 2.924 | 0.0225 | |
| TLK2 | tousled like kinase 2 | 212997_PM_s_at | 212997_PM_s_at | −15.917 | 0.0535 | 9.092 | 0.0836 | |
| iCOS-iCOSL Signaling in T Helper Cells | | | | | | | | |
| BAD | BCL2 associated agonist of cell death | 232660_PM_at | 232660_PM_at | 9.15 | 0.0494 | 4.762 | 0.00665 | 57% |
| IL2RG | interleukin 2 receptor subunit gamma | 204116_PM_at | 204116_PM_at | −5.818 | 0.0111 | 2.991 | 0.0255 | |
| ITPR2 | inositol 1,4,5-trisphosphate receptor type 2 | 202661_PM_at | 211360_PM_at | 7.618 | 0.0821 | 1.726 | 0.000000987 | |
| LCP2 | lymphocyte cytosolic protein 2 | 205270_PM_s_at | 244578_PM_at | 13.175 | 0.0285 | 1.811 | 0.000182 | |
| NFATC3 | nuclear factor of activated T-cells 3 | 207416_PM_s_at | 225137_PM_at | 6.702 | 0.0321 | −2.819 | 0.0128 | |
| PIK3R5 | phosphoinositide-3-kinase regulatory subunit 5 | 227645_PM_at | 220566_PM_at | 15.229 | 0.0712 | 3.662 | 0.0925 | |
| PTEN | phosphatase and tensin homolog | 242622_PM_x_at | 242622_PM_x_at | −4.642 | 0.0714 | 2.541 | 0.0613 | |
| Hereditary Breast Cancer Signaling | | | | | | | | |
| ARID1A | AT-rich interaction domain 1A | 210649_PM_s_at | 210649_PM_s_at | −5.203 | 0.00996 | 3.091 | 0.0296 | 40% |
| GADD45B | growth arrest and DNA damage inducible beta | 209304_PM_x_at | 213560_PM_at | 7.698 | 0.0123 | 2.295 | 0.000121 | |

TABLE 11-continued 15 shared pathways identified by Ingenuity Pathway Analysis between the
CTOT-08 Discovery and the 129 NU validation cohorts

| Symbol | Entrez Gene Name | Affymetrix (A1#) | Affymetrix (A2#) | Expr Log Ratio (A1#) | Expr p-value (A1#) | Expr Log Ratio (A2) | Expr p-value (A2) | Agreement between Discovery and Validation |
|---|---|---|---|---|---|---|---|---|
| PIK3R5 | phosphoinositide-3-kinase regulatory subunit 5 | 227645_PM_at | 220566_PM_at | 15.229 | 0.0712 | 3.662 | 0.0925 | |
| PTEN | phosphatase and tensin homolog | 242622_PM_x_at | 242622_PM_x_at | −4.642 | 0.0714 | 2.541 | 0.0613 | |
| SFN | stratifin | 33322_PM_i_at | 33322_PM_i_at | −8.156 | 0.0196 | 4.805 | 0.0561 | |
| NFAT Signaling | | | | | | | | |
| CD79A | CD79a molecule | 1555779_PM_a_at | 205049_PM_s_at | −3.32 | 0.0737 | 1.635 | 0.0701 | 57% |
| FCGR2A | Fc fragment of IgG receptor IIa | 203561_PM_at | 1565674_PM_at | 12.301 | 0.056 | 2.076 | 0.0208 | |
| GNAI2 | G protein subunit alpha i2 | 201040_PM_at | 215996_PM_at | −4.069 | 0.000286 | 2.104 | 0.00197 | |
| ITPR2 | inositol 1,4,5-trisphosphate receptor type | 202661_PM_at | 211360_PM_s_at | 7.618 | 0.0821 | 1.726 | 0.000000987 | |
| LCP2 | lymphocyte cytosolic protein 2 | 205270_PM_s_at | 244578_PM_at | 13.175 | 0.0285 | 1.811 | 0.000182 | |
| NFATC3 | nuclear factor of activated T-cells 3 | 207416_PM_s_at | 225137_PM_at | 6.702 | 0.0321 | −2.819 | 0.0128 | |
| PIK3R5 | phosphoinositide-3-kinase regulatory subunit 5 | 227645_PM_at | 220566_PM_at | 15.229 | 0.0712 | 3.662 | 0.0925 | |
| B-cell Receptor Signaling | | | | | | | | |
| BAD | BCL2 associated agonist of cell death | 232660_PM_at | 232660_PM_at | 9.15 | 0.0494 | 4.762 | 0.00665 | 30% |
| CD79A | CD79a molecule | 1555779_PM_a_at | 205049_PM_s_at | −3.32 | 0.0737 | 1.635 | 0.0701 | |
| CDC42 | cell division cycle 42 | 208727_PM_s_at | 208727_PM_s_at | −5.037 | 0.00719 | 2.715 | 0.0127 | |
| CREB1 | cAMP responsive element binding protein 1 | 225565_PM_at | 204312_PM_x_at | −6.724 | 0.0757 | 5.191 | 0.098 | |
| DAPP1 | dual adaptor of phosphotyrosine and 3-phosphoinositides 1 | 222858_PM_s_at | 236707_PM_at | −6.212 | 0.0832 | 2.661 | 0.00444 | |
| FCGR2A | Fc fragment of IgG receptor IIa | 203561_PM_at | 1565674_PM_at | 12.301 | 0.056 | 2.076 | 0.0208 | |
| NFATC3 | nuclear factor of activated T-cells 3 | 207416_PM_s_at | 225137_PM_at | 6.702 | 0.0321 | −2.819 | 0.0128 | |
| PIK3R5 | phosphoinositide-3-kinase regulatory subunit 5 | 227645_PM_at | 220566_PM_at | 15.229 | 0.0712 | 3.662 | 0.0925 | |
| PTEN | phosphatase and tensin homolog | 242622_PM_x_at | 242622_PM_x_at | −4.642 | 0.0714 | 2.541 | 0.0613 | |
| PTK2B | protein tyrosine kinase 2 beta | 203110_PM_at | 203110_PM_at | −4.637 | 0.0000941 | 3.945 | 0.0335 | |

TABLE 11-continued 15 shared pathways identified by Ingenuity Pathway Analysis between the
CTOT-08 Discovery and the 129 NU validation cohorts

| Symbol | Entrez Gene Name | Affymetrix (A1#) | Affymetrix (A2#) | Expr Log Ratio (A1#) | Expr p-value (A1#) | Expr Log Ratio (A2) | Expr p-value (A2) | Agreement between Discovery and Validation |
|---|---|---|---|---|---|---|---|---|
| | p70S6K Signaling | | | | | | | |
| BAD | BCL2 associated agonist of cell death | 232660_PM_at | 232660_PM_at | 9.15 | 0.0494 | 4.76 | 0.00632 | 29% |
| CD79A | CD79a molecule | 1555779_PM_a_at | 205049_PM_s_at | −3.32 | 0.0737 | 1.63 | 0.0641 | |
| GNAI2 | G protein subunit alpha i2 | 201040_PM_at | 215996_PM_at | −4.069 | 0.000286 | 2.1 | 0.00203 | |
| IL2RG | interleukin 2 receptor subunit gamma | 204116_PM_at | 204116_PM_at | −5.818 | 0.0111 | 2.99 | 0.024 | |
| PIK3R5 | phosphoinositide-3-kinase regulatory subunit 5 | 227645_PM_at | 227553_PM_at | 15.229 | 0.0712 | 3.82 | 0.0627 | |
| PPP2R1A | protein phosphatase 2 scaffold subunit alpha | 200695_PM_at | 200695_PM_at | −6.035 | 0.0188 | 2.92 | 0.021 | |
| SFN | stratifin | 33322_PM_i_at | 33322_PM_i_at | −8.156 | 0.0196 | 4.8 | 0.0513 | |
| | Huntington's Disease Signaling | | | | | | | |
| CLTA | clathrin light chain A | 200960_PM_x_at | 216296_PM_at | 13.863 | 0.0538 | 5.88 | 0.0577 | 71% |
| CREB1 | cAMP responsive element binding protein 1 | 225565_PM_at | 204312_PM_x_at | −6.724 | 0.0757 | 5.19 | 0.088 | |
| GLS | glutaminase | 203158_PM_s_at | 223079_PM_s_at | 9.006 | 0.0941 | 2.21 | 0.00504 | |
| PIK3R5 | phosphoinositide-3-kinase regulatory subunit 5 | 227645_PM_at | 227553_PM_at | 15.229 | 0.0712 | 3.82 | 0.0627 | |
| REST | RE1 silencing transcription factor | 212920_PM_at | 204535_PM_s_at | 9.753 | 0.0414 | 3.76 | 0.0529 | |
| SIN3A | SIN3 transcription regulator family member A | 238005_PM_s_at | 238006_PM_at | 3.902 | 0.000343 | 4.55 | 0.0283 | |
| STX16 | syntaxin 16 | 221499_PM_s_at | 221638_PM_s_at | −12.332 | 0.0942 | 2.57 | 0.0138 | |
| | VEGF Signaling | | | | | | | |
| BAD | BCL2 associated agonist of cell death | 232660_PM_at | 232660_PM_at | 9.15 | 0.0494 | 4.76 | 0.00632 | 50% |
| PIK3R5 | phosphoinositide-3-kinase regulatory subunit 5 | 227645_PM_at | 227553_PM_at | 15.229 | 0.0712 | 3.82 | 0.0627 | |
| PTK2B | protein tyrosine kinase 2 beta | 203110_PM_at | 203110_PM_at | −4.637 | 0.0000941 | 3.94 | 0.031 | |
| SFN | stratifin | 33322_PM_i_at | 33322_PM_i_at | −8.156 | 0.0196 | 4.8 | 0.0513 | |
| | PI3K Signaling in B Lymphocytes | | | | | | | |
| CBL | Cbl proto-oncogene | 225234_PM_at | 229010_PM_at | −7.307 | 0.086 | 2.59 | 0.0187 | 60% |
| CD79A | CD79a molecule | 1555779_PM_a_at | 205049_PM_s_at | −3.32 | 0.0737 | 1.635 | 0.0701 | |
| CREB1 | CAMP responsive element | 225565_PM_at | 204312_PM_x_at | −6.724 | 0.0757 | 5.191 | 0.098 | |

TABLE 11-continued 15 shared pathways identified by Ingenuity Pathway Analysis between the
CTOT-08 Discovery and the 129 NU validation cohorts

| Symbol | Entrez Gene Name | Affymetrix (A1#) | Affymetrix (A2#) | Expr Log Ratio (A1#) | Expr p-value (A1#) | Expr Log Ratio (A2) | Expr p-value (A2) | Agreement between Discovery and Validation |
|---|---|---|---|---|---|---|---|---|
| DAPP1 | binding protein 1 dual adaptor of phosphotyrosine and 3-phosphoinositides 1 | 222858_PM_s_at | 236707_PM_at | −6.212 | 0.0832 | 2.661 | 0.00444 | |
| ITPR2 | inositol 1,4,5-trisphosphate receptor type 2 | 202661_PM_at | 211360_PM_s_at | 7.618 | 0.0821 | 1.726 | 0.000000987 | |
| NFATC3 | nuclear factor of activated T-cells 3 | 207416_PM_s_at | 225137_PM_at | 6.702 | 0.0321 | −2.819 | 0.0128 | |
| PTEN | phosphatase and tensin homolog | 242622_PM_x_at | 242622_PM_x_at | −4.642 | 0.0714 | 2.541 | 0.0613 | |
| PI3K/AKT Signaling | | | | | | | | |
| BAD | BCL2 associated agonist of cell death | 232660_PM_at | 232660_PM_at | 9.15 | 0.0494 | 4.762 | 0.00665 | 17% |
| MCL1 | MCL1, BCL2 family apoptosis regulator | 200796_PM_s_at | 200796_PM_s_at | −5.247 | 0.0671 | 1.85 | 0.0132 | |
| PPP2R1A | protein phosphatase 2 scaffold subunit Aalpha | 200695_PM_at | 200695_PM_at | −6.035 | 0.0188 | 2.924 | 0.0225 | |
| PTEN | phosphatase and tensin homolog | 242622_PM_x_at | 242622_PM_x_at | −4.642 | 0.0714 | 2.541 | 0.0613 | |
| PTGS2 | prostaglandin endoperoxide synthase 2 | 1554997_PM_a_at | 1554997_PM_a_at | −4.745 | 0.0375 | 1.538 | 0.00018 | |
| SFN | stratifin | 33322_PM_i_at | 33322_PM_i_at | −8.156 | 0.0196 | 4.805 | 0.0561 | |
| CD40 Signaling | | | | | | | | |
| PIK3R5 | phosphoinositide-3-kinase regulatory subunit 5 | 227645_PM_at | 220566_PM_at | 15.229 | 0.0712 | 3.662 | 0.0925 | 50% |
| PTGS2 | prostaglandin endoperoxide synthase 2 | 1554997_PM_a_at | 1554997_PM_a_at | −4.745 | 0.0375 | 1.538 | 0.00018 | |
| Unfolded protein response | | | | | | | | |
| DNAJC3 | DnaJ heat shock protein family (Hsp40) member C3 | 208499_PM_s_at | 1558080_PM_s_at | −5.03 | 0.0333 | 2.973 | 0.0421 | 25% |
| MBTPS1 | membrane bound transcription factor peptidase, site 1 | 201620_PM_at | 201620_PM_at | 7.699 | 0.00952 | −4.059 | 0.0272 | |
| NFE2L2 | nuclear factor, erythroid 2 like 2 | 1567014_PM_s_at | 1567013_PM_at | 6.243 | 0.0121 | 3.584 | 0.0568 | |
| OS9 | OS9, endoplasmic reticulum lectin | 200714_PM_x_at | 215399_PM_s_at | −9.131 | 0.0202 | 3.922 | 0.0826 | |

A1 - CTOT-08 Discovery Samples
A2 - NU Validation Samples

2) In the CTOT-08 dataset, Database for Annotation, Visualization and Integrated Discovery (DAVID) (Huang et al. Genome Biol. 8, Ri83.1-Ri83.16 (2007)) also identified the T-cell receptor pathway as significant (p<0.0001) by Gene Ontology (GO) biological process as well as the canonical T-cell receptor (Kyoto Encyclopedia of Genes and Genomes) KEGG pathway (p<0.001) in the CTOT-08 dataset, and in validation set (129/138 NU samples), DAVID again identified the B-cell receptor, T-cell receptor and the IL-2 receptor beta chain pathways as significant by the canonical KEGG pathways (p=0.0002, 0.01 and 0.03 respectively).

3) Pre-Ranked Gene Set Enrichment Analysis (GSEA) (25) (Version 3.0 Built 0160)

a) GSEA, using Hallmark Gene Sets and fold-change based ranking, identified Allograft Rejection as the top positively enriched significant gene set (q value <0.019) in the CTOT-08 dataset (Table 12). In this analysis, differential gene expression data, ranked based on fold-change, were tested against the Hallmark gene sets (which represent specific well-defined biological states or processes and display most coherent expression) of GSEA. Among the positively enriched gene sets, the Allograft Rejection gene set is identified as the only significant candidate (q value <0.019), with 60 of its genes present in our list of CTOT differentially expressed genes.

TABLE 12

| Pre-ranked GSEA - CTOT-8 Differentially Expressed Genes | | | | | |
|---|---|---|---|---|---|
| NAME | SIZE | ES | NES | NOM p-val | FDR q-va |
| HALLMARK_ALLOGRAFT_REJECTION | 60 | 0.2383333 | 2.223595 | 0.00193424 | 0.0188325 |
| HALLMARK_MYC_TARGETS_V2 | 27 | 0.2770634 | 1.692253 | 0.02708333 | 0.1772495 |
| HALLMARK_E2F_TARGETS | 53 | 0.1884220 | 1.604267 | 0.04868154 | 0.1871493 |
| HALLMARK_COMPLEMENT | 42 | 0.2014579 | 1.566066 | 0.05068226 | 0.1681809 |
| HALLMARK_MYC_TARGETS_V1 | 90 | 0.1414142 | 1.535855 | 0.06759443 | 0.1547716 |
| HALLMARK_WNT_BETA_CATENIN_SIGN | 6 | 0.340537 | 1.044948 | 0.39285713 | 0.8247684 |
| HALLMARK_PANCREAS_BETA_CELLS | 5 | 0.3577741 | 0.985289 | 0.45418328 | 0.8446085 |
| HALLMARK_INTERFERON_GAMMA_RES | 35 | 0.1367178 | 0.963722 | 0.48643005 | 0.7880705 |
| HALLMARK_ESTROGEN_RESPONSE_LAT | 28 | 0.1454956 | 0.929582 | 0.5346154 | 0.7673989 |
| HALLMARK_CHOLESTEROL_HOMEOSTA | 9 | 0.2481153 | 0.916746 | 0.57938147 | 0.7158631 |
| HALLMARK_UNFOLDED_PROTEIN_RESP | 44 | 0.1048951 | 0.813056 | 0.71656686 | 0.8266552 |
| HALLMARK_SPERMATOGENESIS | 17 | 0.1633256 | 0.791926 | 0.72888017 | 0.7883571 |
| HALLMARK_UV_RESPONSE_DN | 16 | 0.1270532 | 0.618169 | 0.93801653 | 0.9293070 | b) Pre-ranked GSEA also identified TNFα-signaling/NFκB-signaling and 'allograft rejection' gene sets (Table 13) as the top two positively enriched candidates in the NU validation set. In this analysis, Differential gene expression data, ranked based on fold-change, were tested against the Hallmark gene sets of GSEA. It identified TNFα-signaling and Allograft Rejection gene sets as top two positively enriched candidates.

TABLE 13

| Pre-ranked GSEA - NU Biorepository Differentially Expressed Genes | | | | | |
|---|---|---|---|---|---|
| NAME | SIZE | ES | NES | NOM p-val | FDR q-val |
| HALLMARK_TNFA_SIGNALING_VIA_NFKB | 27 | 0.34630716 | 2.2195516 | 0 | 0.015379426 |
| HALLMARK_ALLOGRAFT_REJECTION | 15 | 0.41785946 | 1.9719326 | 0.004008016 | 0.052854557 |
| HALLMARK_INTERFERON_GAMMA_RESPONSE | 16 | 0.35805905 | 1.7035453 | 0.027290449 | 0.14941299 |
| HALLMARK_APOPTOSIS | 18 | 0.34367928 | 1.7028997 | 0.02414487 | 0.11271172 |
| HALLMARK_KRAS_SIGNALING_UP | 12 | 0.30834138 | 1.2789063 | 0.17450981 | 0.6062781 |
| HALLMARK_MITOTIC_SPINDLE | 26 | 0.20321079 | 1.2384405 | 0.203125 | 0.5871179 |
| HALLMARK_PI3K_AKT_MTOR_SIGNALING | 15 | 0.24887171 | 1.176204 | 0.26252505 | 0.62166286 |
| HALLMARK_IL2_STAT5_SIGNALING | 11 | 0.27990893 | 1.1312063 | 0.30452675 | 0.62793404 |
| HALLMARK_UV_RESPONSE_UP | 12 | 0.2691257 | 1.1170832 | 0.3187251 | 0.5840298 |
| HALLMARK_PROTEIN_SECRETION | 12 | 0.2540984 | 1.066703 | 0.3608871 | 0.6123108 |
| HALLMARK_INFLAMMATORY_RESPONSE | 13 | 0.23321952 | 1.0066841 | 0.41614908 | 0.66099924 |
| HALLMARK_HYPOXIA | 16 | 0.1681994 | 0.8123587 | 0.6673307 | 0.98092985 |
| HALLMARK_G2M_CHECKPOINT | 14 | 0.17888205 | 0.79593503 | 0.7261663 | 0.9370209 |
| HALLMARK_MTORC1_SIGNALING | 21 | 0.14429314 | 0.78031844 | 0.734127 | 0.89682156 |
| HALLMARK_APICAL_JUNCTION | 13 | 0.1732997 | 0.7377354 | 0.7777778 | 0.9026552 |
| HALLMARK_ESTROGEN_RESPONSE_EARLY | 12 | 0.17221154 | 0.7161518 | 0.81670064 | 0.8738094 |
| HALLMARK_EPITHELIAL_MESENCHYMAL_TRANSITION | 13 | 0.13951592 | 0.6032765 | 0.9160305 | 0.93667006 |

Example 7. Evaluation of Clinical Relevance of the subAR Gene Expression Profile Classifier The clinical outcomes that correlate with (a) the histological diagnosis of subAR, and (b) the gene expression profile biomarker developed in Example 5 were determined and compared; this data is presented in Table 14, wherein statistically significant differences are underlined.

To assess whether subjects who experienced subAR had worse transplant outcomes, a primary clinical composite endpoint (CCE) was devised based on the following criteria:
1) a 24-month biopsy (central read) showing evidence of chronic injury—Interstitial Fibrosis/Tubular Atrophy (IFTA) (Banff ≥Grade II IFTA [ci≥2 or ct≥2], OR
2) Biopsy-proven acute rejection (BPAR) on any 'for-cause biopsy' (central read), OR
3) a decrease in estimated glomerular filtration rate (ΔeGFR) by ≥10 ml/min/1.73 m2 (CKD-EPI) between 4-24 months post-transplant.

De novo Donor Specific Antibodies (dnDSA) were measured for both Class I and II by each participating site as per their practice and were recorded as either positive or negative according to each site's cut-off values. The study protocol required determinations at the time of the 12 and 24 month biopsies, but other values obtained and recorded at any time during the study were also used for our analyses.

To assess the impact of both clinical phenotype and gene expression profile in the first 12 months on transplant outcome (clinical composite or individual endpoints) at 24 months, we used odds ratios (OR) and Fisher's exact test. The two-sample t-test was used to assess the ability of gene expression profile predicted probabilities during intense monitoring to detect resolution of subAR based on the repeat biopsy. Analysis of covariance was used to adjust for differences in predicted probabilities at baseline Table 14 panels A and B show the prevalence of the clinical phenotype of subAR and the clinical impact. Panel 14A shows the prevalence of the subAR clinical phenotype and the impact on transplant outcome as determined by a pre-defined clinical composite endpoint (CCE): occurrence of 1) greater than Grade 2 IFTA (Banff criteria) on the 24-month biopsy, OR 2) biopsy-proven acute rejection (BPAR) at any time during the 24-month study period, OR 3) decrease in eGFR >10 ml/min between 4 and 24 months after transplant. Subjects were divided into 3 clinical phenotype groups (see Table 7): surveillance biopsies each showing only subAR, only TX, or >1 instance of subAR with at least 1 TX. Within the first year following KT, 243 subjects met criteria defining the clinical phenotype of either subAR or TX. 183/243 (75.3%), distributed equally between 3 groups, had sufficient data to meet the CCE; 73.9% with subAR only met the CCE compared to 35.5% with TX only (OR 5.1 [1.7, 16.9]; p<0.001); 53.2% with >1 instance of subAR met the CCE compared to 35.5% with TX only (OR 2.1 [1.1, 4.0]; p=0.027). When individual components of the clinical composite endpoint (IFTA, BPAR, or ΔeGFR) were examined, only BPAR demonstrated significant (p<0.001) when comparing the subAR only to TX only groups. Table 14 panel B shows that there was also a strong association between the development of de novo donor specific antibodies (dnDSA) within the 24-month period and the clinical phenotype of subAR only vs. TX only, when subAR was noted at any time point within the 24-month period (class I p=0.01; class II p=0.01); class II dnDSA was also significantly associated in subjects with ≥1 instance of subAR (p<0.01) when compared to TX only. In addition, the development of dnDSA was noted when the clinical phenotype occurred within the first 12 months following KT when comparing subAR only vs. TX (class I p<0.01; class II p=0.02) and in patients with ≥1 instance of subAR (class I p=0.02; class II p<0.01). Table 14 panels C and D show the prevalence of the gene expression profile (GEP) and the clinical impact. Panel 14C shows the prevalence of a positive GEP biomarker test (above the 0.375 threshold) and the impact on the same pre-defined CCE. Subjects were divided into 3 groups according to the results of the biomarker test(s): positive only, negative only, or >1 instance of a positive with at least 1 negative biomarker test. 116/250 (46.4%) had >1 instance of a positive gene expression profile. Within the first 12 months following KT, 239 subjects met criteria defining the GEP as either positive or negative at both 12 and 24 months; 182/239 (76.2%), distributed equally between the 3 groups, had sufficient clinical data to also define the clinical composite endpoint. 66.7% with only positive tests met the CCE compared to 37.3% with subjects with only negative tests (OR 3.4 [1.3, 9.3]; p=0.009); 48.6% with >1 positive tests met the CCE compared to 37.3% with negative tests only (OR 1.6 [0.8, 3.0]; p=0.17). An analysis of individual components of the clinical endpoint (IFTA, BPAR, or ΔeGFR) revealed that only BPAR showed a significant difference when comparing subjects with positive vs. negative tests only (p=0.003). Panel 14D shows that there was a strong association between the development of dnDSA within the 24-month study period and positive only vs. negative only GEP biomarker tests noted at any time point within the study period (class I p=0.01; class II p=0.04); class II dnDSA was also significantly associated with ≥1 instances of positive only vs. negative only (p=0.01). Finally, when the biomarker test was noted to be positive within the first 12 months following KT, dnDSA class I was significantly higher in subjects with positive vs. negative tests (p=0.03).

TABLE 14

Panel 14A. Association of Clinical Phenotypes with the Composite Clinical Endpoint (CCE)

| Outcome | TX only (no subAR) n/N | % | subAR only (No TX) n/N | % | subAR and TX n/N | % | ≥1 subAR (subAR and TX) n/N | % | subAR only vs. TX only OR (95% CI)* | p-value* | ≥1 subAR vs. TX only OR (95% CI)* | p-value* |
|---|---|---|---|---|---|---|---|---|---|---|---|---|
| CCE | 43/121 | 35.5 | 17/23 | 73.9 | 16/39 | 41.0 | 33/62 | 53.2 | 5.1 (1.7, 16.9) | <0.001 | 2.1 (1.1, 4.0) | 0.027 |
| ≥GR II IFTA | 10/121 | 8.3 | 5/23 | 21.7 | 5/39 | 12.8 | 10/62 | 16.1 | 3.1 (0.7, 11.3) | 0.07 | 2.1 (0.7, 6.1) | 0.13 |

TABLE 14-continued

| | | | | | | | | | | | |
|---|---|---|---|---|---|---|---|---|---|---|---|
| BPAR | 23/121 | 19.0 | 13/23 | 56.5 | 7/39 | 18.0 | 20/62 | 32.3 | 5.5 (1.9, 15.9) | <0.001 | 2.0 (0.9, 4.3) | 0.06 |
| AeGFR | 17/121 | 14.1 | 5/23 | 21.7 | 6/39 | 15.4 | 11/62 | 17.7 | 1.7 (0.4, 5.6) | 0.35 | 1.3 (0.5, 3.2) | 0.52 |

*95% exact confidence interval presented with p-value resulting from a Fisher's Exact Test.

Panel 14B. Association between de novo Anti-HLA Antibody and de novo DSA development and the Clinical Phenotype

| Clinical Phenotype at any time post-TX | subAR only (N = 33) | TX only (N = 146) | p-value[1] | ≥1 subAR (N = 107) | TX only (N = 146) | p-value[1] |
|---|---|---|---|---|---|---|
| Anti-HLA Class 1 | 5 (15.15%) | 27 (18.49%) | 0.6509 | 15 (14.02%) | 27 (18.49%) | 0.3447 |
| Anti-HLA Class 2 | 8 (24.24%) | 33 (22.60%) | 0.8396 | 26 (24.30%) | 33 (22.60%) | 0.7526 |
| DSA Class 1 | 6 (18.18%) | 6 (4.11%) | 0.0103+ | 9 (8.41%) | 6 (4.11%) | 0.1523 |
| DSA Class 2 | 7 (21.21%) | 8 (5.48%) | 0.0084+ | 21 (19.63%) | 8 (5.48%) | 0.0005 |

| | subAR only (N = 35) | TX only (N = 162) | p-value[1] | ≥1 subAR (N = 81) | TX only (N = 162) | p-value[1] |
|---|---|---|---|---|---|---|
| Anti-HLA Class 1 | 4 (11.43%) | 30 (18.52%) | 0.3142 | 9 (11.11%) | 30 (18.52%) | 0.1381 |
| Anti-HLA Class 2 | 7 (20.00%) | 38 (23.46%) | 0.6587 | 18 (22.22%) | 38 (23.46%) | 0.8294 |
| DSA Class 1 | 6 (17.14%) | 6 (3.70%) | 0.0086+ | 9 (11.11%) | 6 (3.70%) | 0.0237 |
| DSA Class 2 | 7 (20.00%) | 11 (6.79%) | 0.0225+ | 16 (19.75%) | 11 (6.79%) | 0.0024 |

[1]p-value from Chi-square test except where + indicates use of Fisher's Exact test.

Pancel 14 C. Association of Gene Expression Profile (GEP) with the Composite Clinical Endpoint (CCE)

| Outcome | TX only (no subAR) n/N | % | subAR only (No TX) n/N | % | subAR and TX n/N | % | ≥1 subAR (subAR and TX) n/N | % | subAR only vs. TX only OR (95% CI)* | p-value* | ≥1 subAR vs. TX only OR (95% CI)* | p-value* |
|---|---|---|---|---|---|---|---|---|---|---|---|---|
| CCE | 41/110 | 37.3 | 18/27 | 66.7 | 17/45 | 37.8 | 35/72 | 48.6 | 3.4 (1.3, 9.3) | 0.009 | 1.6 (0.8, 3.0) | 0.17 |
| ≥GR II IFTA | 10/110 | 9.1 | 3/27 | 11.1 | 7/45 | 15.6 | 10/72 | 13.9 | 1.3 (0.2, 5.4) | 0.72 | 1.6 (0.6, 4.6) | 0.34 |
| BPAR | 24/110 | 21.8 | 14/27 | 51.9 | 5/45 | 11.1 | 19/72 | 26.4 | 3.9 (1.4, 10.2) | 0.003 | 1.3 (0.6, 2.7) | 0.48 |
| AeGFR | 15/110 | 13.6 | 6/27 | 22.2 | 7/45 | 15.6 | 13/72 | 18.1 | 1.8 (0.5, 5.7) | 0.37 | 1.4 (0.6, 3.4) | 0.53 |

*95% exact confidence interval presented with p-value resulting from a Fisher's Exact Test.

Panel 14D. Association between de novo Anti-HLA Antibody and de novo DSA development and the GEP

| GEP at any time post-TX | subAR only (N = 32) | TX only (N = 134) | p-value[1] | ≥1 subAR (N = 116) | TX only (N = 134) | p-value[1] |
|---|---|---|---|---|---|---|
| Anti-HLA Class 1 | 5 (15.63%) | 27 (20.15%) | 0.5600 | 15 (12.93%) | 27 (20.15%) | 0.1279 |
| Anti-HLA Class 2 | 8 (25.00%) | 34 (25.37%) | 0.9652 | 25 (21.55%) | 34 (25.37%) | 0.4779 |
| DSA Class 1 | 6 (18.75%) | 6 (4.48%) | 0.0128+ | 9 (7.76%) | 6 (4.48%) | 0.2760 |
| DSA Class 2 | 6 (18.75%) | 9 (6.72%) | 0.0439+ | 20 (17.24%) | 9 (6.72%) | 0.0096 |

| GEP within Year 1 | subAR only (N = 34) | TX only (N = 148) | p-value[1] | ≥1 subAR (N = 91) | TX only (N = 148) | p-value[1] |
|---|---|---|---|---|---|---|
| Anti-HLA Class 1 | 3 (8.82%) | 29 (29.59%) | 0.1368 | 9 (9.89%) | 29 (29.59%) | 0.0463 |
| Anti-HLA Class 2 | 9 (26.47%) | 38 (25.68%) | 0.9239 | 17 (18.68%) | 38 (25.68%) | 0.2122 |
| DSA Class 1 | 5 (14.71%) | 6 (4.05%) | 0.0338+ | 8 (8.79%) | 6 (4.05%) | 0.1299 |
| DSA Class 2 | 6 (17.65%) | 14 (9.46%) | 0.2195+ | 12 (13.19%) | 14 (9.46%) | 0.3689 |

[1]p-value from Chi-square test except where + indicates use of Fisher's Exact test.

Example 8. Evaluation of subAR Gene Expression Profile Classifier in Clinical Response to Treatment As the subAR gene expression profile classifier defined in Example 5 was found to correlate with worse long-term outcomes, an analysis was performed to evaluate the biomarker set as a correlate of response to treatment.

Figure 9:
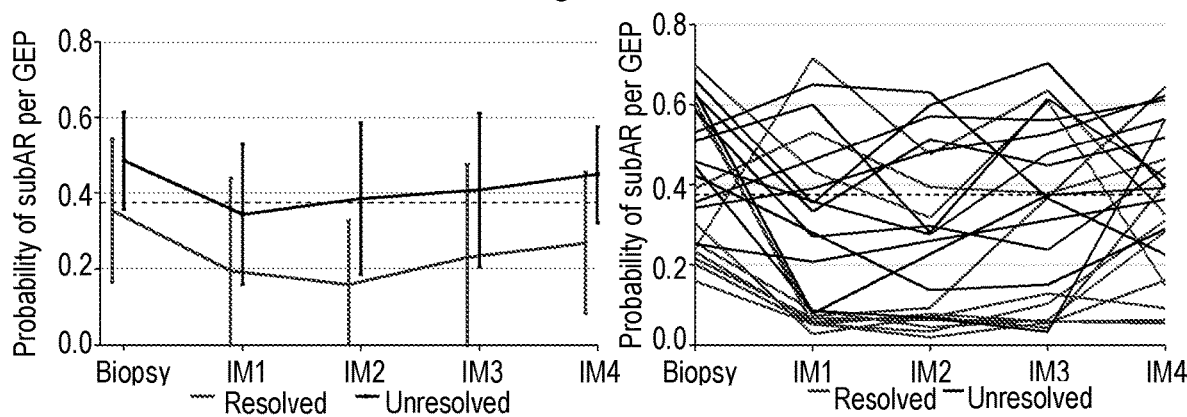
FIG. 9 is a chart (top) and table (bottom) showing resolution of subAR as determined by the subAR gene expression profile classifier developed in Example 5.

23 subjects underwent intense monitoring following a clinical diagnosis of subAR following a surveillance biopsy, using serial peripheral blood sampling every 2 weeks and a repeat 8-week biopsy. The results of this analysis are presented in FIG. 9. Central histology reads between the baseline and 8-week biopsies were compared: 11 (47.8%) (3 untreated) showed histologic resolution ('resolved'), and 12 (52.2%) (1 untreated) showed persistent or worsening rejection ('unresolved'); 12/23 demonstrated persistence or worsening of subAR, including 11/19 (58%) who underwent treatment. Significant differences in the predicted probability using the subAR classifier were observed at 4 (p=0.014) and 8 (p=0.015) weeks between the two groups. When values were adjusted for differences in baseline probabilities, these comparisons remained significant. Changes in the change in probability scores (slope) between baseline and 4 (p=0.045) and 8 weeks (p=0.023) also differed between the two groups. Based on graft histology at baseline in both groups, the 'unresolved' group demonstrated a lower proportion of Borderline (6/12) and higher number of >Borderline rejections (three grade 1A, two AMR, and one Borderline plus AMR) compared to 9/11 Borderline and two grade 1A rejections at baseline in the other group. Of note, while the differences in probability scores between the 2 groups did not reach statistical significance (p=0.073), 7/11 of patients with subAR at baseline were below the threshold (biomarker negative) in the 'resolved' group, whereas 8/12 were above the threshold (biomarker positive) in the 'unresolved' group Thus, the biomarker data show that serial probability scores correlated statistically with histological resolution. Moreover, in the majority of patients, the biomarker at baseline predicted resolution, although this data point did not reach statistical significance. While the sample size was relatively small, these data suggest the potential use of the biomarker to both predict and serially monitor response to treatment of subAR. These findings are especially important given that in the context of a stable creatinine, there is no currently available alternative method to monitor response other than the serial use of invasive biopsies.

These results have further implications for the interpretation of "borderline" changes in kidney biopsies and development of IFTA/antibody-mediated chronic rejection. First, results presented here clearly indicate while ~80% of histological subAR in both cohorts consisted of borderline changes, these were associated with both dnDSA and worse graft outcomes. Second, the correlation between subAR and development dnDSA and worse graft outcomes suggests that T-cell mediated acute rejection is part of a continuum in the development of IFTA and chronic rejection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of distinguishing a non-transplant excellent kidney from a transplant excellent kidney and treatment of the non-transplant excellent kidney or the transplant excellent kidney, in a kidney transplant recipient on an immunosuppressant treatment regimen and having a stable creatinine level, wherein the immunosuppressant treatment regimen comprises administration to the kidney transplant recipient of at least one immunosuppressant drug, the method comprising:

(a) obtaining mRNA derived from a blood sample from the kidney transplant recipient or cDNA complements of mRNA derived from a blood sample from the kidney transplant recipient;

(b) performing a microarray assay, sequencing assay, or qPCR assay on the mRNA derived from the blood sample from the kidney transplant recipient or the cDNA complements of mRNA derived from the blood sample from the kidney transplant recipient and detecting gene expression levels of CXXC5, BMP2K, IGKC, GNB1, SSBP3, and ALDH9A1 in the blood sample from the kidney transplant recipient;

(c) applying a trained algorithm of the gene expression levels determined in (b), wherein the trained algorithm calculates a probability score based on the gene expression levels determined in (b) wherein the probability score is positive when above a predicted probability threshold value and negative when below the predicted probability threshold value;

(d) distinguishing, by the probability score based on the gene expression levels determined in (c), the non-transplant excellent kidney from the transplant excellent kidney, wherein
the kidney transplant recipient has the non-transplant excellent kidney when the probability score is positive, and
the kidney transplant recipient has the transplant excellent kidney when the probability score is negative; and (e) treating the kidney transplant recipient having the non-transplant excellent kidney or the transplant excellent kidney,
wherein,
I) when the kidney transplant recipient has the non-transplant excellent kidney, the step of treating comprises:
performing a biopsy on the kidney transplant recipient;
detecting, from the biopsy, a non-transplant excellent condition in the non-transplant excellent kidney, the non-transplant excellent condition comprising acute rejection, subclinical acute rejection, acute dysfunction with no rejection, and kidney injury;
wherein when acute rejection or subclinical acute rejection is detected in the biopsy, increasing dosage of the immunosuppressant drug of the immunosuppressant treatment regimen or increasing a number of immunosuppressant drugs administered to the kidney transplant recipient in the immunosuppressant treatment regimen; and
wherein when acute dysfunction with no rejection or kidney injury is detected in the biopsy, decreasing dosage of the immunosuppressant drug of the immunosuppressant treatment regimen or decreasing a number of immunosuppressant drugs administered to the kidney transplant recipient in the immunosuppressant treatment regimen and/or performing a blood transfusion; or
II) when the kidney transplant recipient has the transplant excellent kidney, the step of treating comprises:
decreasing dosage of the immunosuppressant drug of the immunosuppressant treatment regimen or decreasing a number of immunosuppressant drugs administered to the kidney transplant recipient in the immunosuppressant treatment regimen.

2. The method of claim 1, wherein the trained algorithm performs a binary classification between a transplant excellent kidney and a non-transplant excellent kidney.

3. The method of claim 1, wherein step (b) further comprises measuring the gene expression levels of TCF4, CEACAM21, MICA, FAM43A, AGPS, TSPAN13, ZADH2, PKM, APOL2, PIK3CG, LIMS1, SP100, APOL6, and ARHGDIB.

4. The method of claim 1, further comprising repeating steps (a) through (d) prior to performing step (e).

5. The method of claim 4, wherein the repeating of steps (a) through (d) occurs at least four weeks after steps (a) through (d) are initially performed in the method.

6. The method of claim 1, wherein the immunosuppressant drug is a calcineurin inhibitor.

7. The method of claim 1, wherein the immunosuppressant drug is an mTOR inhibitor.

8. The method of claim 1, wherein the immunosuppressant drug is selected from the group consisting of: azathioprine, leflunomide, mycophenolic acid, mycophenolate mofetil, prednisolone, hydrocortisone, basiliximab, alemtuzumab, daclizumab, belatacept, orthoclone, anti-thymocyte globulin, anti-lymphocyte globulin, an anti-proliferative drug, and an anti-T cell antibody.

9. The method of claim 1, wherein the blood sample from the kidney transplant recipient comprises whole blood, peripheral blood, serum, plasma, PBLs, PBMCs, T cells, CD4 T cells, CD8 T cells, macrophages, or exosomes.

10. The method of claim 1, wherein step (c) is performed by a computer.

11. The method of claim 1, wherein the kidney transplant recipient is a human.

12. The method of claim 1, wherein the predicted probability threshold value is 0.375.

13. The method of claim 1, wherein the predicted probability threshold value is 0.5.

14. The method of claim 1, wherein step (e)I following detection of acute rejection or subclinical acute rejection in the kidney transplant recipient from the biopsy comprises increasing dosage of the immunosuppressant drug of the immunosuppressant treatment regimen.

15. The method of claim 1, wherein step (e)I following detection of acute rejection or subclinical acute rejection in the kidney transplant recipient from the biopsy comprises increasing a number of immunosuppressant drugs administered to the kidney transplant recipient in the immunosuppressant treatment regimen.

16. The method of claim 1, wherein step (e)II comprises decreasing dosage of the immunosuppressant drug of the immunosuppressant treatment regimen.

17. The method of claim 1, wherein step (e)II comprises decreasing a number of immunosuppressant drugs administered to the kidney transplant recipient in the immunosuppressant treatment regimen.

18. The method of claim 1, wherein step (e)I following detection of acute dysfunction with no rejection or kidney injury in the kidney transplant recipient from the biopsy comprises decreasing dosage of the immunosuppressant drug of the immunosuppressant treatment regimen.

19. The method of claim 1, wherein step (e)I following detection of acute dysfunction with no rejection or kidney injury in the kidney transplant recipient from the biopsy comprises decreasing a number of immunosuppressant drugs administered to the kidney transplant recipient in the immunosuppressant treatment regimen.

20. The method of claim 1, wherein step (e)I following detection of acute dysfunction with no rejection or kidney injury in the kidney transplant recipient from the biopsy comprises performing a blood transfusion.

* * * * *